United States Patent
Doh et al.

(10) Patent No.: US 11,840,574 B2
(45) Date of Patent: Dec. 12, 2023

(54) ANTI-DR5 ANTIBODY AND USE THEREOF

(71) Applicant: DONG-A ST CO., LTD., Seoul (KR)

(72) Inventors: Hyounmie Doh, Yongin-si (KR); Dongsop Lee, Yongin-si (KR); Hanyoung Lee, Suwon-si (KR); Yoojin Kim, Yongin-si (KR); Kyungmi Han, Suwon-si (KR); Eunee Jung, Suwon-si (KR); Donghyeon Kim, Daejeon (KR); Eongsup Song, Anyang-si (KR); Kum-Joo Shin, Anyang-si (KR); Soyon Woo, Seoul (KR)

(73) Assignee: DONG-A ST CO., LTD., Seoul (KR)

( * ) Notice: Subject to any disclaimer, the term of this patent is extended or adjusted under 35 U.S.C. 154(b) by 1101 days.

(21) Appl. No.: 16/492,780

(22) PCT Filed: Feb. 8, 2018

(86) PCT No.: PCT/KR2018/001711
§ 371 (c)(1),
(2) Date: Sep. 10, 2019

(87) PCT Pub. No.: WO2018/174408
PCT Pub. Date: Sep. 27, 2018

(65) Prior Publication Data
US 2023/0133381 A1    May 4, 2023

(30) Foreign Application Priority Data
Mar. 21, 2017   (KR) ........................ 10-2017-0035623

(51) Int. Cl.
*C07K 16/28* (2006.01)
*A61P 35/00* (2006.01)
*C12N 15/63* (2006.01)

(52) U.S. Cl.
CPC .......... *C07K 16/2878* (2013.01); *A61P 35/00* (2018.01); *C12N 15/63* (2013.01); *C07K 2317/565* (2013.01); *C07K 2317/73* (2013.01)

(58) Field of Classification Search
CPC .......... C07K 16/2878; C07K 2317/565; C07K 2317/73; A61P 35/00; C12N 15/63
See application file for complete search history.

(56) References Cited

U.S. PATENT DOCUMENTS

| 6,113,898 A | 9/2000 | Anderson et al. |
| 2008/0248037 A1 | 10/2008 | Li et al. |
| 2012/0070432 A1 | 3/2012 | Wiezorek et al. |
| 2015/0353638 A1 | 12/2015 | Zheng et al. |

FOREIGN PATENT DOCUMENTS

| CN | 1440424 | 9/2003 | |
| CN | 101247825 | 8/2008 | |
| CN | 102898524 | 1/2013 | |
| CN | 103282495 | 9/2013 | |
| CN | 104245736 | 12/2014 | |
| EP | 2636736 | 9/2013 | |
| EP | 2684896 | 1/2014 | |
| JP | 2009-542202 | 12/2009 | |
| WO | 2006-083971 | 8/2006 | |
| WO | 2006083971 | 8/2006 | |
| WO | 2010-047509 | 4/2010 | |
| WO | 2011098520 | 8/2011 | |
| WO | 2013148877 | 10/2013 | |
| WO | 2012-057288 | 5/2014 | |
| WO | WO-2015098112 A1 * | 7/2015 | .......... A61K 31/713 |
| WO | 2016122702 | 8/2016 | |
| WO | 2017028279 | 2/2017 | |

OTHER PUBLICATIONS

Elrod et al., Analysis of Death Receptor 5 and Caspase-8 Expression in Primary and Metastatic Head and Neck Squamous Cell Carcinoma and Their Prognostic Impact, 2010, PLos ONE, vol. 5, Issue 8, e12178 pp. 1-10 (Year: 2010).*
Daniels et al., Expression of TRAIL and TRAIL receptors in normal and malignant tissue, Cell Research, vol. 15, Issue 6, pp. 430-438 (Year: 2005).*
Graves et al., Apo2L/TRAIL and the Death Receptor 5 Agonist Antibody AMG 655 Cooperate to Promote Receptor Clustering and Antitumor Activity, 2014, Cancer Cell, vol. 26, pp. 177-189 (Year: 2014).*
Intellectual Property India, Office Action of the corresponding Indian Patent Application No. 201947038786. dated Mar. 15, 2022.
Kazuhiro Motoki et al., Enhanced Apoptosis and Tumor Regression Induced by a Direct Agonist Antibody to Tumor Necrosis Factor-Related Apoptosis-Inducing Ligand Receptor 2, Clinical Cancer Research, Apr. 2005.
Claire L Dobson et al., "Human monomeric antibody fragments to TRAIL-R1 and TRAIL-R2 that display potent in vitro agonism", MAbs. Nov. 2009-Dec; 1(6): 552-562.
C Adams et al., "Structural and functional analysis of the interaction between the agonistic monoclonal antibody Apomab and the proapoptotic receptor DR5", Cell Death Differ 15, 751-761 (2008). https://doi.org/10.1038/sj.cdd.4402306.

(Continued)

*Primary Examiner* — Daniel E Kolker
*Assistant Examiner* — Brittney E Donoghue
(74) *Attorney, Agent, or Firm* — LEX IP MEISTER, PLLC

(57) ABSTRACT

The present invention relates to an antibody that specifically binds to death receptor 5 (DR5) and has a function of killing cancer cells. Specifically, provided are an anti-DR5 antibody or antigen-binding fragment thereof, and a use of the antibody or antigen-binding fragment for preventing or treating cancer. The present invention is characterized in that the anti-DR5 antibody or antigen-binding fragment thereof is improved in terms of affinity to DR5, stability, and an effect of killing cancer cells.

21 Claims, 30 Drawing Sheets
Specification includes a Sequence Listing.

(56) References Cited

OTHER PUBLICATIONS

Andres Forero-Torres et al., "Phase 2, multicenter, open-label study of tigatuzumab (CS-1008), a humanized monoclonal antibody targeting death receptor 5, in combination with gemcitabine in chemotherapy-naive patients with unresectable or metastatic pancreatic cancer", Cancer Med. Dec. 2013;2(6):925-32. doi: 10.1002/cam4.137. Epub Oct. 25, 2013.
O Micheau et al., "Death receptors as targets in cancer", Br J Pharmacol. Aug. 2013;169(8):1723-44. doi: 10.1111/bph.12238.
EPO, European Search Report of EP 18772434.9 dated Dec. 14, 2020.
Avi Ashkenazi, Targeting Death and Decoy Receptors of the Tumournecrosis Factor Superfamilty, Nat Rev. Cancer 2: 420-430, Jun. 2002.
Minj Jo et al., Apoptosis induced in normal human Hepatocytes by tumor necrosis factor-related apoptosis-inducing ligand, Nature Medicine 6, 564-567, May 2000.
K Takeda et al., Targeting death-inducing recpetors in cancer therapy, Oncogene, 26, 3745-3757, 2007.
Toshiaki Ohtsuka et al., Synergistic induction of tumor cell apoptosis by death receptor antibody and chemotherapy agent through JNK/p38 and mitochondrial pathway, Oncogene, 22, 2034-2044, 2003.
Andres Forero-Torres et al., Phase 2, multicenter, open-label study of tigatuzumab (CS-1008), a humanized monoclonal antibody targeting death receptor 5, in combination with gemcitabine in chemotherapy-naive patients with unresectable or metastatic pancreatic cancer, Cancer Medicine, 2(6), 925-932, 2013.
Martin Reck et al., A randomized, double-blind, placebo-controlled phase 2 study oftigatuzumab (CS-1008) in combination with carboplatin/paclitaxel inpatients with chemotherapy-naive metastatic/unresectablenon-small cell lung cancer, Lung Cancer, 82, 441-448, 2013.
Andres Forer-Torres et al., Phase 2, multicenter, open-label study of tigatuzumab (CS-1008), a humanized monoclonal antibody targeting death receptor 5, in combination with gemcitabine in chemotherapy-naive patients with unresectable or metastatic pancreatic cancer, Cancer Medicine, 2(6), 925-932, 2013.
Hope M. Amm et al., Mechanisms of Drug Sensitization to TRA-8, an Agnostic Receptor 5 Antibody, Involve Modulation of the Intrinsic Apoptotic Pathway in Human Breast Cancer Cells, Mol Cancer Red Apr. 9, 403, 2011.
Anil Shanker et al., Treating Metastatic Solid Tumors With Bortezomiband a Tumor Necrosis Factor—Related Apoptosis-Inducing Ligand Receptor Agonist Antibody, J Natl Cancer Inst, May 7; 100(9): 649-662, 2008.
Nahoko Nishibori et al., Humanization of chicken monoclonal antibody using phage display system, Molecular Immunology, 43, 634-642, 2006.
Leo Christopher DeRosier et al., Treatment With Gemcitabine and TRA-8 Anti-Death Receptor-5 mAb Reduces Pancreatic Adenocarcinoma Cell Viability In Vitro and Growth In Vivo, J Gastrointest Surg.; 10(9):1291-300, Nov. 2006.
Hideo Yagita etl al., TRAIL and its receptors as targets for cancer therapy, Cancer Sci. 95(10); 777-783 Oct. 2004.
GenBank: AAF32227.1: scFV antibody V region, partial [synthetic construct] (Jul. 26, 2016).
GenBank: BAB71890.1: immunoglobulin lambda light chain, partial [Gallus gallus] (Jul. 26, 2016).
C Adams et al., Structural and functional analysis of the interaction between the agonistic monoclonal antibody Apomab and the proapoptotic receptor DR5, Cell Death and Differentiation, 15, 751-761, Jan. 2008.
Fengtao Liu et al., "The tetravalent anti-DR5 antibody without cross-linking direct induces apoptosis of cancer cells", Biomedicine & Pharmacotherapy 70 (2015) 41-45, http://dx.doi.org/10.1016/j.biopha.2014.12.024.

* cited by examiner

| No. | Sample |
|---|---|
| 1 | AP |
| 2 | D0 |
| 3 | DA1 |
| 4 | DA4 |
| 5 | DA16 |
| 6 | DA18 |
| 7 | DA20 |
| 8 | DA23 |
| 9 | DA26 |
| 10 | DA29 |

SEQUENCE LISTING

```
<160> NUMBER OF SEQ ID NOS: 69

<210> SEQ ID NO 1
<211> LENGTH: 10
<212> TYPE: PRT
<213> ORGANISM: Artificial Sequence
<220> FEATURE:
<223> OTHER INFORMATION: Synthetic_VH-CDR1

<400> SEQUENCE: 1

Gly Phe Thr Phe Ser Ser Phe Asn Met Leu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic_VH-CDR2
```

```
<400> SEQUENCE: 2

Gly Ile Gly Lys Ser Asp Arg Tyr Thr Gly Tyr Gly Ser Ala Val Lys
1               5                   10                  15

Gly

<210> SEQ ID NO 3
<211> LENGTH: 18
<212> TYPE: PRT
<213> ORGANISM: Artificial Sequence
<220> FEATURE:
<223> OTHER INFORMATION: Synthetic_VH-CDR3
<220> FEATURE:
<221> NAME/KEY: MOD_RES
<222> LOCATION: (5)
<223> OTHER INFORMATION: Xaa is Gly or Pro
<220> FEATURE:
<221> NAME/KEY: MOD_RES
<222> LOCATION: (8)
<223> OTHER INFORMATION: Xaa is Ser or Lys

<400> SEQUENCE: 3

Asp Ala Gly Ser Xaa Cys Gly Xaa Gly Gly Trp Thr Gly Ala Cys Ile
1               5                   10                  15

Asp Thr

<210> SEQ ID NO 4
<211> LENGTH: 13
<212> TYPE: PRT
<213> ORGANISM: Artificial Sequence
<220> FEATURE:
<223> OTHER INFORMATION: Synthetic_VL-CDR1

<400> SEQUENCE: 4

Ser Gly Gly Asp Ser Tyr Ala Gly Ser Tyr Tyr Tyr Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic_VL-CDR2
<220> FEATURE:
<221> NAME/KEY: MOD_RES
<222> LOCATION: (5)
<223> OTHER INFORMATION: Xaa is Arg, Leu, or Lys
<220> FEATURE:
<221> NAME/KEY: MOD_RES
<222> LOCATION: (6)
<223> OTHER INFORMATION: Xaa is Pro, Met, or Ala
<220> FEATURE:
<221> NAME/KEY: MOD_RES
<222> LOCATION: (7)
<223> OTHER INFORMATION: Xaa is Ser, Pro, or Lys

<400> SEQUENCE: 5

Asn Asn Asn Asn Xaa Xaa Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic_VL-CDR3
<220> FEATURE:
<221> NAME/KEY: MOD_RES
<222> LOCATION: (6)
<223> OTHER INFORMATION: Xaa is Ser, Ala, or Asp
```

```
<220> FEATURE:
<221> NAME/KEY: MOD_RES
<222> LOCATION: (7)
<223> OTHER INFORMATION: Xaa is Tyr or Gly
<220> FEATURE:
<221> NAME/KEY: MOD_RES
<222> LOCATION: (8)
<223> OTHER INFORMATION: Xaa is Val, Met, Gly, or Ala
<220> FEATURE:
<221> NAME/KEY: MOD_RES
<222> LOCATION: (10)
<223> OTHER INFORMATION: Xaa is Ile, Ala, Arg, or Gly

<400> SEQUENCE: 6

Gly Ser Arg Asp Ser Xaa Xaa Xaa Gly Xaa
1               5                   10

<210> SEQ ID NO 7
<211> LENGTH: 18
<212> TYPE: PRT
<213> ORGANISM: Artificial Sequence
<220> FEATURE:
<223> OTHER INFORMATION: Synthetic_VH-CDR3

<400> SEQUENCE: 7

Asp Ala Gly Ser Gly Cys Gly Ser Gly Gly Trp Thr Gly Ala Cys Ile
1               5                   10                  15

Asp Thr

<210> SEQ ID NO 8
<211> LENGTH: 18
<212> TYPE: PRT
<213> ORGANISM: Artificial Sequence
<220> FEATURE:
<223> OTHER INFORMATION: Synthetic_VH-CDR3

<400> SEQUENCE: 8

Asp Ala Gly Ser Pro Cys Gly Ser Gly Gly Trp Thr Gly Ala Cys Ile
1               5                   10                  15

Asp Thr

<210> SEQ ID NO 9
<211> LENGTH: 18
<212> TYPE: PRT
<213> ORGANISM: Artificial Sequence
<220> FEATURE:
<223> OTHER INFORMATION: Synthetic_VH-CDR3

<400> SEQUENCE: 9

Asp Ala Gly Ser Pro Cys Gly Lys Gly Gly Trp Thr Gly Ala Cys Ile
1               5                   10                  15

Asp Thr

<210> SEQ ID NO 10
<211> LENGTH: 7
<212> TYPE: PRT
<213> ORGANISM: Artificial Sequence
<220> FEATURE:
<223> OTHER INFORMATION: Synthetic_VL-CDR2

<400> SEQUENCE: 10

Asn Asn Asn Asn Arg Pro Ser
1               5

<210> SEQ ID NO 11
<211> LENGTH: 7
```

```
<212> TYPE: PRT
<213> ORGANISM: Artificial Sequence
<220> FEATURE:
<223> OTHER INFORMATION: Synthetic_VL-CDR2

<400> SEQUENCE: 11

Asn Asn Asn Asn Leu Met Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic_VL-CDR2

<400> SEQUENCE: 12

Asn Asn Asn Asn Lys Ala Lys
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic_VL-CDR3

<400> SEQUENCE: 13

Gly Ser Arg Asp Ser Ser Tyr Val Gly Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic_VL-CDR3

<400> SEQUENCE: 14

Gly Ser Arg Asp Ser Ala Gly Met Gly Ala
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic_VL-CDR3

<400> SEQUENCE: 15

Gly Ser Arg Asp Ser Asp Gly Gly Gly Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic_VL-CDR3

<400> SEQUENCE: 16

Gly Ser Arg Asp Ser Ser Gly Ala Gly Gly
1               5                   10

<210> SEQ ID NO 17
<211> LENGTH: 127
<212> TYPE: PRT
```

<213> ORGANISM: Artificial Sequence
<220> FEATURE:
<223> OTHER INFORMATION: Synthetic_Heavy chain variable region

<400> SEQUENCE: 17

```
Ala Val Thr Leu Asp Glu Ser Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 18
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Phe Thr Ile Ser Arg Asp Asp Ser Lys Ser Thr Val Tyr
65                  70                  75                  80

Leu Gln Met Asn Ser Leu Arg Ala Glu Asp Thr Ala Val Tyr Tyr Cys
                85                  90                  95

Val Arg Asp Ala Gly Ser Gly Cys Gly Ser Gly Gly Trp Thr Gly Ala
            100                 105                 110

Cys Ile Asp Thr Trp Gly Gln Gly Thr Leu Val Thr Val Ser Ser
        115                 120                 125
```

<210> SEQ ID NO 19
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

Asn Met Leu Trp Val Arg Gln Ala Pro Gly Lys Gly Leu Glu Trp Val
            35                  40                  45

Ala Gly Ile Gly Lys Ser Asp Arg Tyr Thr Gly Tyr Gly Ser Ala Val
        50                  55                  60

Lys Gly Arg Phe Thr Ile Ser Arg Asp Thr Ser Lys Ser Thr Val Tyr
65                  70                  75                  80

Leu Gln Met Asn Ser Leu Arg Ala Glu Asp Thr Ala Val Tyr Tyr Cys
            85                  90                  95

Val Arg Asp Ala Gly Ser Gly Cys Gly Ser Gly Gly Trp Thr Gly Ala
            100                 105                 110

Cys Ile Asp Thr Trp Gly Gln Gly Thr Leu Val Thr Val Ser Ser
            115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
            35                  40                  45

Ala Gly Ile Gly Lys Ser Asp Arg Tyr Thr Gly Tyr Gly Ser Ala Val
        50                  55                  60

Lys Gly Arg Phe Thr Ile Ser Arg Asp Ser Lys Asn Thr Val Tyr
65                  70                  75                  80

Leu Gln Met Asn Ser Leu Arg Ala Glu Asp Thr Ala Val Tyr Tyr Cys
            85                  90                  95

Val Arg Asp Ala Gly Ser Gly Cys Gly Ser Gly Gly Trp Thr Gly Ala
            100                 105                 110

Cys Ile Asp Thr Trp Gly Gln Gly Thr Leu Val Thr Val Ser Ser
            115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
            35                  40                  45

Ala Gly Ile Gly Lys Ser Asp Arg Tyr Thr Gly Tyr Gly Ser Ala Val
        50                  55                  60

Lys Gly Arg Phe Thr Ile Ser Arg Asp Asp Ser Lys Ser Thr Ala Tyr
65                  70                  75                  80

Leu Gln Met Asn Ser Leu Arg Ala Glu Asp Thr Ala Val Tyr Tyr Cys

```
                    85                  90                  95

Val Arg Asp Ala Gly Ser Gly Cys Gly Ser Gly Gly Trp Thr Gly Ala
                100                 105                 110

Cys Ile Asp Thr Trp Gly Gln Gly Thr Leu Val Thr Val Ser Ser
            115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 22

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Phe
                20                  25                  30

Asn Met Leu Trp Val Arg Gln Ala Pro Gly Lys Gly Leu Glu Trp Val
            35                  40                  45

Ala Gly Ile Gly Lys Ser Asp Arg Tyr Thr Gly Tyr Gly Ser Ala Val
        50                  55                  60

Lys Gly Arg Phe Thr Ile Ser Arg Asp Asp Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Ser Gly Cys Gly Ser Gly Gly Trp Thr Gly Ala
                100                 105                 110

Cys Ile Asp Thr Trp Gly Gln Gly Thr Leu Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 23

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Phe
                20                  25                  30

Asn Met Leu Trp Val Arg Gln Ala Pro Gly Lys Gly Leu Glu Trp Val
            35                  40                  45

Ala Gly Ile Gly Lys Ser Asp Arg Tyr Thr Gly Tyr Gly Ser Ala Val
        50                  55                  60

Lys Gly Arg Phe Thr Ile Ser Arg Asp Asp Ser Lys Ser Thr Val Tyr
65                  70                  75                  80

Leu Gln Met Asn Ser Leu Arg Ala Glu Asp Thr Ala Val Tyr Tyr Cys
                85                  90                  95

Ser Arg Asp Ala Gly Ser Gly Cys Gly Ser Gly Gly Trp Thr Gly Ala
                100                 105                 110

Cys Ile Asp Thr Trp Gly Gln Gly Thr Leu Val Thr Val Ser Ser
            115                 120                 125

<210> SEQ ID NO 24
<211> LENGTH: 127
```

<212> TYPE: PRT
<213> ORGANISM: Artificial Sequence
<220> FEATURE:
<223> OTHER INFORMATION: Synthetic_Heavy chain variable region

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Phe Thr Ile Ser Arg Asp Asp Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ala Gly Ser Gly Cys Gly Ser Gly Gly Trp Thr Gly Ala
                100                 105                 110

Cys Ile Asp Thr Trp Gly Gln Gly Thr Leu Val Thr Val Ser Ser
            115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Phe Thr Ile Ser Arg Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Ala Gly Ser Gly Cys Gly Ser Gly Gly Trp Thr Gly Ala
                100                 105                 110

Cys Ile Asp Thr Trp Gly Gln Gly Thr Leu Val Thr Val Ser Ser
            115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe

-continued

```
                20                  25                  30
Asn Met Leu Trp Val Arg Gln Ala Pro Gly Lys Gly Leu Glu Trp Val
            35                  40                  45
Ala Gly Ile Gly Lys Ser Asp Arg Tyr Thr Gly Tyr Gly Ser Ala Val
        50                  55                  60
Lys Gly Arg Phe Thr Ile Ser Arg Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Asp Ala Gly Ser Gly Cys Ser Gly Gly Trp Thr Gly Ala
            100                 105                 110
Cys Ile Asp Thr Trp Gly Gln Gly Thr Leu Val Thr Val Ser Ser
        115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 27

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Asn Met Leu Trp Val Arg Gln Ala Pro Gly Lys Gly Leu Glu Trp Val
        35                  40                  45
Ala Gly Ile Gly Lys Ser Asp Arg Tyr Thr Gly Tyr Gly Ser Ala Val
    50                  55                  60
Lys Gly Arg Phe Thr Ile Ser Arg Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Asp Ala Gly Ser Gly Cys Ser Gly Gly Trp Thr Gly Ala
            100                 105                 110
Cys Ile Asp Thr Trp Gly Gln Gly Thr Leu Val Thr Val Ser Ser
        115                 120                 125

<210> SEQ ID NO 28
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 28

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Asn Met Leu Trp Val Arg Gln Ala Pro Gly Lys Gly Leu Glu Trp Val
        35                  40                  45
Ala Gly Ile Gly Lys Ser Asp Arg Tyr Thr Gly Tyr Gly Ser Ala Val
    50                  55                  60
Lys Gly Arg Phe Thr Ile Ser Arg Asp Asp Ser Lys Ser Thr Val Tyr
65                  70                  75                  80
```

```
Leu Gln Met Asn Ser Leu Arg Ala Glu Asp Thr Ala Val Tyr Tyr Cys
                85                  90                  95

Val Arg Asp Ala Gly Ser Pro Cys Gly Ser Gly Gly Trp Thr Gly Ala
            100                 105                 110

Cys Ile Asp Thr Trp Gly Gln Gly Thr Leu Val Thr Val Ser Ser
        115                 120                 125
```

<210> SEQ ID NO 29
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Phe Thr Ile Ser Arg Asp Ser Lys Ser Thr Val Tyr
65                  70                  75                  80

Leu Gln Met Asn Ser Leu Arg Ala Glu Asp Thr Ala Val Tyr Tyr Cys
                85                  90                  95

Val Arg Asp Ala Gly Ser Pro Cys Gly Lys Gly Gly Trp Thr Gly Ala
            100                 105                 110

Cys Ile Asp Thr Trp Gly Gln Gly Thr Leu Val Thr Val Ser Ser
        115                 120                 125
```

<210> SEQ ID NO 30
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 30

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Gly Gln Ser Thr Val Tyr
65                  70                  75                  80

Leu Gln Met Asn Ser Leu Arg Ala Glu Asp Thr Gly Thr Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 31

```
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 31

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Arg
65                  70                  75                  80

Leu Gln Leu Asn Asn Leu Arg Ala Glu Asp Thr Gly Thr Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125

<210> SEQ ID NO 32
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 32

Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Tyr
65                  70                  75                  80

Leu Gln Met Asn Ser Leu Arg Ala Glu Asp Thr Gly Thr Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125

<210> SEQ ID NO 33
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 33

Ala Val Thr Leu Asp Glu Ser Gly Gly Gly Leu Gln Thr Pro Gly Gly
1               5                   10                  15
```

```
Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Arg
65                  70                  75                  80

Leu Gln Met Asn Ser Leu Arg Ala Glu Asp Thr Gly Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 34
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 34

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Val Arg
65                  70                  75                  80

Leu Gln Leu Asn Asn Leu Arg Ala Glu Asp Thr Ala Val Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 35
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 35

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Arg
65                  70                  75                  80
```

```
Leu Gln Leu Asn Asn Leu Arg Ala Glu Asp Thr Ala Val Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 36
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 36

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Tyr
65                  70                  75                  80

Leu Gln Met Asn Ser Leu Arg Ala Glu Asp Thr Ala Val Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

<210> SEQ ID NO 37
<211> LENGTH: 127
<212> TYPE: PRT
<213> ORGANISM: Artificial Sequence
<220> FEATURE:
<223> OTHER INFORMATION: Synthetic_Heavy chain variable region

<400> SEQUENCE: 37

```
Ala Val Thr Leu Asp Glu Ser Gly Gly Gly Leu Gln Thr Pro Gly Gly
1               5                   10                  15

Gly Leu Ser Leu Val Cys Lys Gly Ser Gly Phe Thr Phe Ser Ser Phe
            20                  25                  30

Asn Met Leu Trp Val Arg Gln Ala Pro Gly Lys Gly Leu Glu Trp Val
        35                  40                  45

Ala Gly Ile Gly Lys Ser Asp Arg Tyr Thr Gly Tyr Gly Ser Ala Val
    50                  55                  60

Lys Gly Arg Ala Thr Ile Ser Arg Asp Asp Gly Gln Ser Thr Ala Arg
65                  70                  75                  80

Leu Gln Met Asn Ser Leu Arg Ala Glu Asp Thr Ala Val Tyr Tyr Cys
                85                  90                  95

Val Lys Asp Ala Gly Ser Gly Cys Gly Ser Gly Gly Trp Thr Gly Ala
            100                 105                 110

Cys Ile Asp Thr Trp Gly His Gly Thr Glu Val Ile Val Ser Ser
        115                 120                 125
```

```
<210> SEQ ID NO 38
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 38

Leu Thr Gln Pro Ser Ser Val Ser Ala Asn Leu Gly Gly Thr Val Glu
1               5                   10                  15

Ile Thr Cys Ser Gly Gly Asp Ser Tyr Ala Gly Ser Tyr Tyr Tyr Gly
            20                  25                  30

Trp Tyr Gln Gln Lys Ala Pro Gly Ser Ala Pro Val Thr Val Ile Tyr
        35                  40                  45

Asn Asn Asn Asn Arg Pro Ser Asn Ile Pro Ser Arg Phe Ser Gly Ser
    50                  55                  60

Thr Ser Gly Ser Thr Ala Thr Leu Thr Ile Thr Gly Val Gln Ala Glu
65                  70                  75                  80

Asp Glu Ala Val Tyr Phe Cys Gly Ser Arg Asp Ser Ser Tyr Val Gly
                85                  90                  95

Ile Phe Gly Ala Gly Thr Thr Leu Thr Val Leu
            100                 105

<210> SEQ ID NO 39
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Arg Pro Ser Gly Val Pro Ser Arg Phe
    50                  55                  60

Ser Gly Ser Thr Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Ser
                85                  90                  95

Tyr Val Gly Ile Phe Gly Gln Gly Thr Lys Val Glu Ile Lys
            100                 105                 110

<210> SEQ ID NO 40
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45
```

```
Leu Ile Tyr Asn Asn Asn Arg Pro Ser Gly Val Pro Ser Arg Phe
        50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Gly Ser Arg Asp Ser Ser
                 85                  90                  95

Tyr Val Gly Ile Phe Gly Gln Gly Thr Lys Val Glu Ile Lys
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Ser Gly Gly Asp Ser Tyr Ala Gly Ser
                20                  25                  30

Tyr Tyr Tyr Gly Trp Tyr Gln Gln Lys Pro Gly Lys Ala Pro Lys Thr
            35                  40                  45

Leu Ile Tyr Asn Asn Asn Arg Pro Ser Gly Val Pro Ser Arg Phe
        50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gly Ser Arg Asp Ser Ser
                 85                  90                  95

Tyr Val Gly Ile Phe Gly Gln Gly Thr Lys Val Glu Ile Lys
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys Ser Gly Gly Asp Ser Tyr Ala Gly Ser
                20                  25                  30

Tyr Tyr Tyr Gly Trp Tyr Gln Gln Lys Pro Gly Lys Ala Pro Lys Thr
            35                  40                  45

Leu Ile Tyr Asn Asn Asn Leu Met Pro Gly Val Pro Ser Arg Phe
        50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Gly Ser Arg Asp Ser Ser
                 85                  90                  95

Tyr Val Gly Ile Phe Gly Gln Gly Thr Lys Val Glu Ile Lys
            100                 105                 110

<210> SEQ ID NO 43
<211> LENGTH: 110
<212> TYPE: PRT
```

-continued

```
<213> ORGANISM: Artificial Sequence
<220> FEATURE:
<223> OTHER INFORMATION: Synthetic_Light chain variable region

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Arg Pro Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Ala
                85                  90                  95

Gly Met Gly Ala Phe Gly Gln Gly Thr Lys Val Glu Ile Lys
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Lys Ala Lys Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Ser
                85                  90                  95

Tyr Val Gly Ile Phe Gly Gln Gly Thr Lys Val Glu Ile Lys
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Arg Pro Ser Gly Val Pro Ser Arg Phe
    50                  55                  60
```

-continued

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Asp
                85                  90                  95

Gly Gly Gly Arg Phe Gly Gln Gly Thr Lys Val Glu Ile Lys
            100                 105                 110

<210> SEQ ID NO 46
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Asn Arg Pro Ser Gly Val Pro Ser Arg Phe
50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Ser
                85                  90                  95

Gly Ala Gly Gly Phe Gly Gln Gly Thr Lys Val Glu Ile Lys
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Synthetic_Light chain variable region

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Ser Gly Gly Asp Ser Tyr Ala Gly Ser
            20                  25                  30

Tyr Tyr Tyr Gly Trp Tyr Gln Gln Lys Pro Gly Lys Ala Pro Lys Thr
        35                  40                  45

Leu Ile Tyr Asn Asn Asn Asn Arg Pro Ser Gly Val Pro Ser Arg Phe
50                  55                  60

Ser Gly Ser Thr Ser Gly Thr Asp Phe Thr Leu Thr Ile Ser Ser Leu
65                  70                  75                  80

Gln Pro Glu Asp Phe Ala Thr Tyr Tyr Cys Gly Ser Arg Asp Ser Ser
                85                  90                  95

Tyr Val Gly Ile Phe Gly Gln Gly Thr Lys Val Glu Ile Lys
            100                 105                 110

<210> SEQ ID NO 48
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 48

Leu Thr Gln Pro Ser Ser Val Ser Ala Asn Leu Gly Gly Thr Val Glu
1               5                   10                  15

Ile Thr Cys Ser Gly Gly Asp Ser Tyr Ala Gly Ser Tyr Tyr Tyr Gly
            20                  25                  30

Trp Tyr Gln Gln Lys Ala Pro Gly Ser Ala Pro Val Thr Val Ile Tyr
        35                  40                  45

Asn Asn Asn Asn Arg Pro Ser Asn Ile Pro Ser Arg Phe Ser Gly Ser
    50                  55                  60

Thr Ser Gly Ser Thr Ala Thr Leu Thr Ile Thr Gly Val Gln Ala Glu
65                  70                  75                  80

Asp Glu Ala Thr Tyr Tyr Cys Gly Ser Arg Asp Ser Ser Tyr Val Gly
                85                  90                  95

Ile Phe Gly Ala Gly Thr Thr Leu Thr Val Leu
            100                 105

<210> SEQ ID NO 49
<211> LENGTH: 107
<212> TYPE: PRT
<213> ORGANISM: Artificial Sequence
<220> FEATURE:
<223> OTHER INFORMATION: Synthetic_Light chain variable region

<400> SEQUENCE: 49

Leu Thr Gln Pro Ser Ser Val Ser Ala Asn Leu Gly Gly Thr Val Glu
1               5                   10                  15

Ile Thr Cys Ser Gly Gly Asp Ser Tyr Ala Gly Ser Tyr Tyr Tyr Gly
            20                  25                  30

Trp Tyr Gln Gln Lys Ala Pro Gly Ser Ala Pro Val Thr Val Ile Tyr
        35                  40                  45

Asn Asn Asn Asn Arg Pro Ser Asn Ile Pro Ser Arg Phe Ser Gly Ser
    50                  55                  60

Thr Ser Gly Ser Thr Ala Thr Leu Thr Ile Thr Gly Val Gln Ala Glu
65                  70                  75                  80

Asp Glu Ala Thr Tyr Phe Cys Gly Ser Arg Asp Ser Ser Tyr Val Gly
                85                  90                  95

Ile Phe Gly Ala Gly Thr Thr Leu Thr Val Leu
            100                 105

<210> SEQ ID NO 50
<211> LENGTH: 72
<212> TYPE: DNA
<213> ORGANISM: Artificial Sequence
<220> FEATURE:
<223> OTHER INFORMATION: Synthetic_forward primer for heavy chain
      variable region

<400> SEQUENCE: 50
ggtcagtcct ctagatcttc cggcggtggt ggcagctccg gtggtggcgg ttccgccgtg    60
acgttggacg ag                                                       72

<210> SEQ ID NO 51
<211> LENGTH: 44
<212> TYPE: DNA
<213> ORGANISM: Artificial Sequence
<220> FEATURE:
<223> OTHER INFORMATION: Synthetic_reverse primer for heavy chain
      variable region

<400> SEQUENCE: 51
ctggccggcc tggccactag tggaggagac gatgacttcg gtcc       44

<210> SEQ ID NO 52
<211> LENGTH: 38
<212> TYPE: DNA
<213> ORGANISM: Artificial Sequence
<220> FEATURE:
<223> OTHER INFORMATION: Synthetic_forward primer for light chain
      variable region

<400> SEQUENCE: 52
gtggcccagg cggccctgac tcagccgtcc tcggtgtc       38

<210> SEQ ID NO 53
<211> LENGTH: 34
<212> TYPE: DNA
<213> ORGANISM: Artificial Sequence
<220> FEATURE:
<223> OTHER INFORMATION: Synthetic_reverse primer for light chain
      variable region

<400> SEQUENCE: 53
ggaagatcta gaggactgac ctaggacggt cagg       34

<210> SEQ ID NO 54
<211> LENGTH: 42
<212> TYPE: DNA
<213> ORGANISM: Artificial Sequence
<220> FEATURE:
<223> OTHER INFORMATION: Synthetic_forward primer for scFv

<400> SEQUENCE: 54
gaggaggagg aggaggaggt ggcccaggcg gccctgactc ag       42

<210> SEQ ID NO 55
<211> LENGTH: 47
<212> TYPE: DNA
<213> ORGANISM: Artificial Sequence
<220> FEATURE:
<223> OTHER INFORMATION: Synthetic_reverse primer for scFv

<400> SEQUENCE: 55
gaggaggagg aggaggagga gctggccggc ctggccacta gtggagg       47

<210> SEQ ID NO 56
<211> LENGTH: 20
<212> TYPE: DNA
<213> ORGANISM: Artificial Sequence
<220> FEATURE:
<223> OTHER INFORMATION: Synthetic_sequencing primer (forward)

<400> SEQUENCE: 56
acactttatg cttccggctc       20

<210> SEQ ID NO 57
<211> LENGTH: 20
<212> TYPE: DNA
<213> ORGANISM: Artificial Sequence
<220> FEATURE:
<223> OTHER INFORMATION: Synthetic_sequencing primer (reverse)

<400> SEQUENCE: 57
caaaatcacc ggaaccagag       20

<210> SEQ ID NO 58
<211> LENGTH: 19
<212> TYPE: DNA
<213> ORGANISM: Artificial Sequence
<220> FEATURE:
<223> OTHER INFORMATION: Synthetic_forward primer for heavy chain variable region

<400> SEQUENCE: 58
gctagccgcc accatgggc                                                    19

<210> SEQ ID NO 59
<211> LENGTH: 37
<212> TYPE: DNA
<213> ORGANISM: Artificial Sequence
<220> FEATURE:
<223> OTHER INFORMATION: Synthetic_reverse primer for heavy chain variable region

<400> SEQUENCE: 59
aggggccctt ggtggaggcc tggccggcct ggccact                                37

<210> SEQ ID NO 60
<211> LENGTH: 20
<212> TYPE: DNA
<213> ORGANISM: Artificial Sequence
<220> FEATURE:
<223> OTHER INFORMATION: Synthetic_forward primer for heavy chain constant region

<400> SEQUENCE: 60
gcctccacca agggcccctc                                                   20

<210> SEQ ID NO 61
<211> LENGTH: 20
<212> TYPE: DNA
<213> ORGANISM: Artificial Sequence
<220> FEATURE:
<223> OTHER INFORMATION: Synthetic_reverse primer for heavy chain constant region

<400> SEQUENCE: 61
cgggatccct tgccggccgt                                                   20

<210> SEQ ID NO 62
<211> LENGTH: 19
<212> TYPE: DNA
<213> ORGANISM: Artificial Sequence
<220> FEATURE:
<223> OTHER INFORMATION: Synthetic_forward primer for heavy chain

<400> SEQUENCE: 62
gctagccgcc accatgggc                                                    19

<210> SEQ ID NO 63
<211> LENGTH: 20
<212> TYPE: DNA
<213> ORGANISM: Artificial Sequence
<220> FEATURE:
<223> OTHER INFORMATION: Synthetic_reverse primer for heavy chain

<400> SEQUENCE: 63
cgggatccct tgccggccgt                                                   20

<210> SEQ ID NO 64
<211> LENGTH: 18
<212> TYPE: DNA

```
<213> ORGANISM: Artificial Sequence
<220> FEATURE:
<223> OTHER INFORMATION: Synthetic_forward primer for light chain
      variable region

<400> SEQUENCE: 64
aagcttgccg ccaccatg                                                    18

<210> SEQ ID NO 65
<211> LENGTH: 37
<212> TYPE: DNA
<213> ORGANISM: Artificial Sequence
<220> FEATURE:
<223> OTHER INFORMATION: Synthetic_reverse primer for light chain
      variable region

<400> SEQUENCE: 65 aggggcggc cacggtccgg gaagatctag aggactg                                37

<210> SEQ ID NO 66
<211> LENGTH: 20
<212> TYPE: DNA
<213> ORGANISM: Artificial Sequence
<220> FEATURE:
<223> OTHER INFORMATION: Synthetic_forward primer for light chain
      constant region (kappa)

<400> SEQUENCE: 66
cggaccgtgg ccgcccctc                                                   20

<210> SEQ ID NO 67
<211> LENGTH: 19
<212> TYPE: DNA
<213> ORGANISM: Artificial Sequence
<220> FEATURE:
<223> OTHER INFORMATION: Synthetic_reverse primer for light chain
      constant region (kappa)

<400> SEQUENCE: 67
gctctagact agcactcgc                                                   19

<210> SEQ ID NO 68
<211> LENGTH: 18
<212> TYPE: DNA
<213> ORGANISM: Artificial Sequence
<220> FEATURE:
<223> OTHER INFORMATION: Synthetic_forward primer for light chain

<400> SEQUENCE: 68
aagcttgccg ccaccatg                                                    18

<210> SEQ ID NO 69
<211> LENGTH: 19
<212> TYPE: DNA
<213> ORGANISM: Artificial Sequence
<220> FEATURE:
<223> OTHER INFORMATION: Synthetic_reverse primer for light chain

<400> SEQUENCE: 69
gctctagact agcactcgc                                                   19
```

ANTI-DR5 ANTIBODY AND USE THEREOF

Incorporated by reference in its entirety herein is a computer-readable nucleotide/amino acid sequence listing submitted herewith and identified as follows: –44,888 bytes ASCII (Text) the named "LPP20192427US_sequence_listing.txt," created Sep. 10, 2019.

TECHNICAL FIELD

The present disclosure pertains to an antibody binding specifically to death receptor 5 (DR5) and having the function of killing cancer cells and, more particularly, to an anti-DR5 antibody or an antigen-binding fragment thereof, and use of the antibody or the antigen-binding fragment in preventing or treating cancer.

BACKGROUND ART

The cell apoptosis pathway through TNF-related apoptosis inducing ligand (TRAIL or Apo2L) and death receptor 5 (DR5), which is one of the receptors thereof, induces cancer cell-selective apoptosis without affecting normal cells and is regarded as an important target for the development of cancer therapeutic agents (Ashkenazi et al., Nat Rev Cancer 2: 420, 2002).

Currently, recombinant TRAIL and death receptor-specific antibodies, which both target DR5, are developed as therapeutic agents against cancer cells.

As for TRAIL, the problem therewith is the low selectivity for DR5 because the ligand binds not only to DR4 (Death receptor 4, TRAIL-Receptor 1) and DR5 (Death receptor 5, TRAIL-Receptor 2), which transduce apoptotic signals, but also to DcR1 (Decoy Receptor 1, TRAIL-Receptor 3) and DcR2 (Decoy Receptor 1, TRAIL-Receptor 4), which cannot transduce apoptotic signals. In addition, recombinant TRAIL is poor in stability and has the adverse effect of inducing apoptosis in normal cells including astrocytes, hepatocytes, keratinocytes etc. (Jo et al., Nature Medicine 6, 564-567, 2000). Hence, active research has been made into the development of anti-DR5 and anti-DR4 antibodies that induces the selective apoptosis of cancer cells, with little adverse effects In relation to death receptor-specific antibodies, clinical trials have been conducted to evaluate cytotoxic activity of the anti-DR5 antibody developed by Genentech Incorporated (U.S.A.) and Amgen (U.S.A.). Human Genome Sciences (U.S.A.) conducted phase II clinical trials for the anti-DR5 antibody HGS-ETR2 and the anti-DR4 antibody HGS-ETR1, but has since stopped development. In addition, development was terminated for anti-DR5 antibodies such as Apomab, Conatumumab, tigatuzumab, etc.

Cell apoptosis occurs largely through two major mechanisms, the extrinsic apoptosis pathway and the intrinsic apoptosis pathway. Most chemotherapeutic agents and radiotherapy induce cancer cell death via p53-mediated intrinsic apoptosis, while DR5-mediated apoptosis is induced through p53-non-dependent extrinsic apoptosis pathway and intrinsic apoptosis pathway (Takeda et al., Oncogene, 26, 3745-3757, 2007). In the extrinsic apoptosis pathway, TRAIL or antibodies bind to DR5 to form a Death-Inducing Signaling Complex (DISC), which through the adaptor protein (FADD) activates the apoptosis-initiating proteases caspase-8 and caspase-10. Then, caspase-8 activates the downstream proteases caspase-3 and caspase-7 while inducing the intrinsic apoptosis through the mitochondria (Ohtsuka et al., Oncogene, 22, 2034-2044, 2003).

With the growing importance of TRAIL as a target for use in cancer therapy, development of more effective and potent TRAIL-targeted agents is required.

DETAILED DESCRIPTION OF THE INVENTION

Technical Problem

The present disclosure aims to provide an anti-DR5 antibody that binds specifically to death receptor 5 (DR5) to effectively kill various cancer cells, and a use thereof.

One aspect provides an anti-DR5 antibody or an antigen-binding fragment thereof.

Another aspect provides a pharmaceutical composition for prevention or treatment of cancer, the composition comprising the anti-DR5 antibody and/or the antigen-binding fragment.

Another aspect provides a method for preventing or treating cancer, the method comprising a step of administering the anti-DR5 antibody and/or the antigen-binding fragment to a subject in need thereof.

Another aspect provides a use of the anti-DR5 antibody and/or the antigen-binding fragment in preventing or treating cancer or in preparing an anticancer agent.

Another aspect provides a polynucleotide molecule encoding the anti-DR5 antibody or the antigen-binding fragment, a recombinant vector carrying the polynucleotide, and a recombinant cell harboring the recombinant vector.

Another aspect provides a method for preparing an anti-DR5 antibody or an antigen-binding fragment thereof, the method comprising a step of expressing the polynucleotide molecule.

Technical Solution

Provided are an anti-DR5 antibody that binds specifically to death receptor 5 (DR5) to effectively induce the death of various cancer cells, and a pharmaceutical composition comprising the same for prevention or treatment of cancer.

The antibody provided herein is a TRAIL-uncompetitive antibody that retains a constant level of antigen binding activity irrespective of TRAIL (TNF-related apoptosis inducing ligand) concentrations. Hence, the antibody can be effectively developed into innovative novel antibody drugs or diagnostic agents exhibiting superior efficacy compared to previously developed antibody drugs.

Death receptor 5 (DR5), also known as TRAIL receptor 2 (TRAILR2) or tumor necrosis factor receptor superfamily member 10B (TNFRSF10B), is a cell surface receptor of the TNF-receptor superfamily that binds TRAIL and mediates apoptosis by transducing an apoptosic signal. DR5 is shown to interact with Caspase 8, Caspase 10, FADD (Fas-Associated protein with Death Domain), and TRAIL. The DR5 may be derived from mammals and may be, for example, a human DR5 (e.g., NCBI accession no. UniProtKB/Swiss-Prot: Q6FH58).

An aspect provides a polypeptide that specifically recognizes and/or binds to DR5. The polypeptide may be one selected from the group consisting of the amino acid sequences of SEQ ID NOS: 1 to 16. More specifically, the polypeptide may have the amino acid sequence of one selected from the group consisting of SEQ ID NOS: 1, 2, 4, and 7 to 16.

As used herein, the expression "a protein, polypeptide, or polynucleotide having an amino acid sequence or a nucleotide sequence" is intended to encompass all the cases in which a protein, polypeptide, or polynucleotide includes, consists essentially of, or consists of the sequence.

Those polypeptides may be used as complementarity determining regions (CDRs) of the anti-DR5 antibody.

The polypeptides and their applicable complementarity determining regions are summarized in Table 1, below:

TABLE 1

| | Sequence | SEQ ID NO |
|---|---|---|
| $V_H$-CDR1 | GFTFSSFNML | 1 |
| $V_H$-CDR2 | GIGKSDRYTGYGSAVKG | 2 |
| $V_H$-CDR3 | DAGSX1CGX2GGWTGACIDT (X1 = G or P; X2 = S or K) | 3 |
| | DAGSGCGSGGWTGACIDT | 7 |
| | DAGSPCGSGGWTGACIDT | 8 |
| | DAGSPCGKGGWTGACIDT | 9 |
| $V_L$-CDR1 | SGGDSYAGSYYYG | 4 |
| $V_L$-CDR2 | NNNNX3X4X5 (X3 = R, L, or K; X4 = P, M, or A; X5 = S, P, or K) | 5 |
| | NNNNRPS | 10 |
| | NNNNLMP | 11 |
| | NNNNKAK | 12 |
| $V_L$-CDR3 | GSRDSX6X7X8GX9 (X6= S, A, or D; X7= Y or G; X8 = V, M, G, or A; X9 = I, A, R, or G) | 6 |
| | GSRDSSYVGI | 13 |
| | GSRDSAGMGA | 14 |
| | GSRDSDGGGR | 15 |
| | GSRDSSGAGG | 16 |

(In Table 1, $V_H$-CDR1, $V_H$-CDR2, and $V_H$-CDR3 represent heavy-chain complementarity determining regions and $V_L$-CDR1, $V_L$-CDR2, and $V_L$-CDR3 represent light-chain complementarity determining regions)

Another aspect provides a DR5-targeting polypeptide molecule comprising at least one selected from the group consisting of the polypeptides described above. The DR5-targeting polypeptide molecule has the characteristic of acting to trigger cancer cell death (e.g., apoptosis of cancer cells) without competing with the DR5 ligand TRAIL.

The DR5-targeting polypeptide molecule may comprise the aforementioned heavy-chain complementarity determining regions or light-chain complementarity determining regions of the anti-DR5 antibody, or a combination thereof; or a heavy-chain variable region including the heavy-chain complementarity determining region, a light-chain variable region including the light-chain complementarity determining region, or a combination thereof.

The DR5-targeting polypeptide molecule may function as, but is not limited to, an anti-DR5 antibody, an antigen-binding fragment of the antibody, or an anti-DR5 antibody analog (a structure having a similar scaffold and function to an antibody; e.g., peptibody, nanobody, and the like), or as a precursor or component (e.g., CDR) of a multi-specific antibody.

The term "peptibody", as used herein, refers to a fusion protein (peptide+antibody) mimicking an antibody in terms of framework and function in which a peptide is fused to a partial or entire constant region, e.g., Fc, of an antibody. In this context, one or more peptides as described above may serve as an antigen-binging fragment (heavy chain and/or light chain CDR or variable region).

The term "nanobody," also called a single-domain antibody, as used herein, refers to an antibody fragment which possesses a monomeric single variable domain of an antibody and shows selectivity for certain antigens, similar to a full length antibody. Its molecular weights generally ranges from about 12 kDa to about 15 kDa, which is much smaller than that (about 150 kDa to about 160 kDa) of a full length antibody (inclusive of two heavy chains and two light chains) and, in some cases, even than that of an Fab or scFv fragment.

As used herein, the term "multi-specific antibody" (inclusive of bispecific antibody) refers to an antibody recognizing and/or binding to two or more different antigens, or recognizing and/or binding to different sites of the same antigen, and one of the antigen binding sites of the multi-specific antibody may include the polypeptide described above.

One aspect provides an anti-DR5 antibody comprising as a complementarity determining region at least one polypeptide selected from the group of the polypeptides described above, or an antigen-binding fragment thereof. The anti-DR5 antibody provided herein, which has the efficacy of a DR5 agonist, acts to cluster DR5 molecules that exist separately on the cell surface, to generate and transduce an apoptotic signal within the cell, thereby inducing cell death.

The anti-DR5 antibody or the antigen-binding fragment thereof may comprise as a heavy-chain complementarity determining region at least one selected from the group consisting of:

a polypeptide having the amino acid sequence of SEQ ID NO: 1 ($V_H$-CDR1), a polypeptide having the amino acid sequence of SEQ ID NO: 2 ($V_H$-CDR2), and a polypeptide having the amino acid sequence of SEQ ID NO: 3 ($V_H$-CDR3).

The amino acid sequence of SEQ ID NO: 3 is the same as that of the following General Formula 1:

[General Formula 1]

(SEQ ID NO: 3)

D-A-G-S-X1-C-G-X2-G-G-W-T-G-A-C-I-D-T wherein,

X1 is G or P, and

X2 is S or K.

In one embodiment, the polypeptide of SEQ ID NO: 3 usable as the heavy-chain CDR3 of the anti-DR5 antibody or the antigen-binding fragment thereof may have at least one selected from the group consisting of the amino acid sequences of, for example, SEQ ID NOS: 7, 8, and 9 (in the following amino acid sequences, the bold and underlined letters represent amino acid residues modified from the amino acid sequence of SEQ ID NO: 7):

SEQ ID NO: 7:
DAGSGCGSGGWTGACIDT

SEQ ID NO: 8:
DAGSPCGSGGWTGACIDT

SEQ ID NO: 9:
DAGSPCGKGGWTGACIDT

In another embodiment, the anti-DR5 antibody or the antigen-binding fragment thereof may comprise as a light-chain complementarity determining region at least one selected from the group consisting of:

a polypeptide having the amino acid sequence of SEQ ID NO: 4 ($V_L$-CDR1), a polypeptide having the amino acid sequence of SEQ ID NO: 5 ($V_L$-CDR2), and a polypeptide having the amino acid sequence of SEQ ID NO: 6 polypeptide ($V_L$-CDR3).

The amino acid sequences of SEQ ID NOS: 5 and 6 are the same as those of the following General Formulas 2 and 3, respectively.

[General Formula 2]   (SEQ ID NO: 5)

N-N-N-N-X3-X4-X5 wherein,
X3 is R, L, or K,
X4 is P, M, or A, and
X5 is S, P, or K;

[General Formula 3]   (SEQ ID NO: 6)

G-S-R-D-S-X6-X7-X8-G-X9 wherein,
X6 is S, A, or D,
X7 is Y or G,
X8 is V, M, G, or A, and
X9 is I, A, R, or G.

In one embodiment, the polypeptide of SEQ ID NO: 5 available as the light-chain CDR2 of the anti-DR5 antibody or the antigen-binding fragment thereof may have at least one selected from the group consisting of the amino acid sequences of SEQ ID NOS: 10, 11, and 12 (in the following amino acid sequences, the bold and underlined letters represent amino acid residues modified from the amino acid sequence of SEQ ID NO: 10):

SEQ ID NO: 10:
NNNNRPS

SEQ ID NO: 11:
NNNNLMP

SEQ ID NO: 12:
NNNNKAK

In one embodiment, the polypeptide of SEQ ID NO: 6 available as the light-chain CDR3 of the anti-DR5 antibody or the antigen-binding fragment thereof may have at least one selected from the group consisting of the amino acid sequences of SEQ ID NOS: 13, 14, 15, and 16 (in the following amino acid sequences, the bold and underlined letters represent amino acid residues modified from the amino acid sequence of SEQ ID NO: 13):

SEQ ID NO: 13:
GSRDSSYVGI

SEQ ID NO: 14:
GSRDSAGMGA

SEQ ID NO: 15:
GSRDSDGGGR

SEQ ID NO: 16:
GSRDSSGAGG

In one embodiment, the anti-DR5 antibody or the antigen-binding fragment thereof may comprise:

at least one heavy-chain complementarity determining region selected from the group consisting of a polypeptide having the amino acid sequence of SEQ ID NO: 1 ($V_H$-CDR1), a polypeptide having the amino acid sequence of SEQ ID NO: 2 ($V_H$-CDR2), and a polypeptide having the amino acid sequence of SEQ ID NO: 3 ($V_H$-CDR3), or a heavy-chain variable region including the at least one heavy-chain complementarity determining region described above;

at least one light-chain complementarity determining region selected from the group consisting of a polypeptide having the amino acid sequence of SEQ ID NO: 4 ($V_L$-CDR1), a polypeptide having the amino acid sequence of SEQ ID NO: 5 ($V_L$-CDR2), and a polypeptide having the amino acid sequence of SEQ ID NO: 6 ($V_L$-CDR3), or a light-chain variable region including the at least one light-chain complementarity determining region described above;

a combination of the heavy-chain complementarity determining region and the light-chain complementarity determining region described above; or a combination of the heavy-chain variable region and the light-chain variable region described above.

More specifically, the anti-DR5 antibody or the antigen-binding fragment thereof may comprise:

at least one heavy-chain complementarity determining region selected from the group consisting of a polypeptide having the amino acid sequence of SEQ ID NO: 1 ($V_H$-CDR1), a polypeptide having the amino acid sequence of SEQ ID NO: 2 ($V_H$-CDR2), and a polypeptide having the amino acid sequence selected from the group consisting of SEQ ID NO: 7 to SEQ ID NO: 9 ($V_H$-CDR3), or a heavy-chain variable region including the at least one heavy-chain complementarity determining region described above;

at least one light-chain complementarity determining region selected from the group consisting of a polypeptide having the amino acid sequence of SEQ ID NO: 4 ($V_L$-CDR1), a polypeptide having the amino acid sequence selected from the group consisting of SEQ ID NO: 10 to SEQ ID NO: 12 ($V_L$-CDR2), and a polypeptide having the amino acid sequence selected from the group consisting of SEQ ID NO: 13 to SEQ ID NO: 16 ($V_L$-CDR3), or a light-chain variable region including the at least one light-chain complementarity determining region described above;

a combination of the heavy-chain complementarity determining region and the light-chain complementarity determining region described above; or a combination of the heavy-chain variable region and the light-chain variable region described above.

In one embodiment, the anti-DR5 antibody or the antigen-binding fragment may comprise:

a heavy-chain variable region comprising a polypeptide having the amino acid sequence of SEQ ID NO: 1 ($V_H$-CDR1), a polypeptide having the amino acid sequence of SEQ ID NO: 2 ($V_H$-CDR2), and a polypeptide having the amino acid sequence selected from the group consisting of SEQ ID NO: 7 to SEQ ID NO: 9 ($V_H$-CDR3); and a light-chain variable region comprising a polypeptide having the amino acid sequence of SEQ ID NO: 4 ($V_L$-CDR1), a polypeptide having the amino acid sequence selected from the group consisting of SEQ ID NO: 10 to SEQ ID NO: 12 ($V_L$-CDR2), and a polypeptide having the amino acid sequence selected from the group consisting of SEQ ID NO: 13 to SEQ ID NO: 16 ($V_L$-CDR3).

In one embodiment, the anti-DR5 antibody or the antigen-binding fragment thereof may comprise a combination of the heavy-chain variable regions and light-chain variable regions given in Tables 2 and 3 below.

TABLE 2

Sequences of Heavy Chain Complementarity-Determining Region (CDR)

| SEQ ID NO | $V_H$-CDR1 | SEQ ID NO | $V_H$-CDR2 | SEQ ID NO | $V_H$-CDR3 |
|---|---|---|---|---|---|
| 1 | GFTFSSFNML | 2 | GIGKSDRYTGYGSAVKG | 7 | DAGSGCGSGGWTGACIDT |
| 1 | GFTFSSFNML | 2 | GIGKSDRYTGYGSAVKG | 8 | DAGSPCGSGGWTGACIDT |
| 1 | GFTFSSFNML | 2 | GIGKSDRYTGYGSAVKG | 9 | DAGSPCGKGGWTGACIDT |

TABLE 3

Sequences of Light Chain CDR

| SEQ ID NO | $V_L$-CDR1 | SEQ ID NO | $V_L$-CDR2 | SEQ ID NO | $V_L$-CDR3 |
|---|---|---|---|---|---|
| 4 | SGGDSYAGSYYYG | 10 | NNNNRPS | 13 | GSRDSSYVGI |
| 4 | SGGDSYAGSYYYG | 11 | NNNNLMP | 13 | GSRDSSYVGI |
| 4 | SGGDSYAGSYYYG | 10 | NNNNRPS | 14 | GSRDSAGMGA |
| 4 | SGGDSYAGSYYYG | 12 | NNNNKAK | 13 | GSRDSSYVGI |
| 4 | SGGDSYAGSYYYG | 10 | NNNNRPS | 15 | GSRDSDGGGR |
| 4 | SGGDSYAGSYYYG | 10 | NNNNRPS | 16 | GSRDSSGAGG |

Provided in another aspect is a heavy-chain variable region comprising the heavy-chain complementarity determining region, a light-chain variable region comprising the light-chain complementarity determining region, or a combination thereof. For example, the heavy-chain variable region may comprise the amino acid sequence selected from the group consisting of SEQ ID NO: 17 to SEQ ID NO: 37 and the light-chain variable region may comprise the amino acid sequence selected from the group consisting of SEQ ID NO: 38 to SEQ ID NO: 49.

Therefore, the anti-DR5 antibody or the antigen-binding fragment thereof may comprise:

a heavy-chain variable region having the amino acid sequence selected from the group consisting of SEQ ID NO: 17 to SEQ ID NO: 37;

a light-chain variable region having the amino acid sequence selected from the group consisting of SEQ ID NO: 38 to SEQ ID NO: 49; or a combination thereof.

In an embodiment, the anti-DR5 antibody may be an animal-derived antibody (e.g., mouse-derived antibody), a chimeric antibody (e.g., mouse-human chimeric antibody), or a humanized antibody. The antibody or antigen-binding fragment may be isolated from a living body or non-naturally occurring. The antibody or antigen-binding fragment may be recombinant or synthetic.

In another embodiment, the antibody may be derived (isolated) from any animal, such as mammals including humans, birds, etc. For example, the antibody may be a human antibody, a mouse antibody, a donkey antibody, a sheep antibody, a rabbit antibody, a goat antibody, a guinea pig antibody, a camel antibody, a horse antibody, or a chicken antibody. Herein, a human antibody is an antibody having an amino acid sequence of human immunoglobulin and includes an antibody isolated from a library of human immunoglobulins or from an animal that has been transgenic for at least one human immunoglobulin and does not include endogenous immunoglobulins.

The anti-DR5 antibody may be monoclonal or polyclonal and may be, for example, a monoclonal antibody. A monoclonal antibody can be prepared using a method widely known in the art, for example, using a phage display technique. Alternatively, the anti-DR5 antibody may be constructed in the form of a mouse-derived monoclonal antibody.

Except for the heavy-chain CDR and light-chain CDR portions or the heavy-chain variable and light-chain variable regions as defined above, the anti-DR5 antibody or the antigen-binding fragment thereof may be derived from any subtype of immunoglobulin (e.g., IgA, IgD, IgE, IgG (IgG1, IgG2, IgG3, IgG4), IgM, and the like), for example, from the framework portion, and/or light-chain constant region and/or heavy-chain constant region.

A full length antibody (e.g., IgG type) has a structure with two full-length light chains and two full-length heavy chains, in which each light chain is linked to a corresponding heavy chain via a disulfide bond. The constant region of an antibody is divided into a heavy-chain constant region and a light-chain constant region, and the heavy-chain constant region is of a gamma (γ), mu (μ), alpha (α), delta (δ) and epsilon (ε) type and has gamma1 (γ1), gamma2 (γ2), gamma3 (γ3), gamma4 (γ4), alpha1 (α1) and alpha2 (α2) as its subclass. The light chain constant region is of either a kappa (κ) or lambda (λ) type.

As used herein, the term "heavy chain" is intended to encompass a full-length heavy chains and fragments thereof, the full-length heavy chain comprising a variable region $V_H$ inclusive of amino acid sequences sufficient to provide specificity to antigens, three constant regions, $C_{H1}$, $C_{H2}$, and $C_{H3}$, and a hinge. The term "light chain" is intended to encompass full-length light chains and fragments thereof, the full-length light chain comprising a variable region $V_L$ inclusive of amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. As used herein, the terms "specifically binding" and "specifically recognizing" have the same general meaning as known to one of ordinary skill in the art, and indicate that an antibody and an antigen specifically interact with each other to lead to an immunological reaction.

The term "antigen-binding fragment" used herein refers to fragments of an intact immunoglobulin including a portion of a polypeptide accounting for an antigen-binding site. The antigen-binding fragment may be scFv, (scFv)$_2$, scFvFc, Fab, Fab', or F(ab')$_2$, but is not limited thereto.

Among the antigen-binding fragments, Fab, which includes light chain and heavy chain variable regions, a light chain constant region, and a first heavy chain constant region $C_{H1}$, has one antigen-binding site.

Fab' is different from Fab in that Fab' includes a hinge region with at least one cysteine residue at the C-terminal of $C_{H1}$.

An F(ab')$_2$ antibody is formed through disulfide bridging of the cysteine residues in the hinge region of Fab'. Fv is a minimal antibody fragment composed of only a heavy chain variable region and a light chain variable region. Recombination techniques of generating an Fv fragment are widely known in the art.

Two-chain Fv includes a heavy chain variable region and a light chain region which are linked to each other by a non-covalent bond. Single-chain Fv generally includes a heavy-chain variable region and a light-chain variable region which are linked to each other by a covalent bond via a peptide linker or linked at the C-terminals to have a dimer structure like the two-chain Fv.

The antigen-binding fragments may be obtained using protease (for example, Fab may be obtained by restrictively cleaving a whole antibody with papain, and an F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody, which functions to provide flexibility for the antigen-binding site.

Another aspect provides a pharmaceutical composition comprising the anti-DR5 antibody or the antigen-binding fragment thereof as an effective ingredient for prevention and/or treatment of cancer.

Another aspect provides a method for prevention and/or treatment of cancer, the method comprising a step of administering a pharmaceutically effective amount of the anti-DR5 antibody or the antigen-binding fragment thereof to a subject in need thereof. The method for prevention and/or treatment of cancer may further comprise a step of identifying a patient in need of prevention and/or treatment of cancer (for example, diagnosing or selecting a subject to be treated) prior to the administering step.

The anti-DR5 antibody can be usefully applied to the prevention or treatment of cancer. Because, as described above, the anti-DR5 antibody provided herein functions as a DR5 agonist, it may be advantageous that the cancer cells express DR5 in order for the anti-DR5 antibody to exert sufficient efficacy (e.g., anticancer efficacy such as cancer cell death) when applied thereto. In addition, the cancer may be a TRAIL-sensitive cancer or a TRAIL-resistant cancer. In one embodiment, concrete examples of the cancer include blood cancer, lung cancer, stomach cancer, liver cancer, bone cancer, pancreatic cancer, skin cancer, head and neck cancer, skin melanoma, uterine cancer, ovarian cancer, rectal cancer, colorectal cancer, colon cancer, breast cancer, uterine sarcoma, fallopian tube carcinoma, endometrial carcinoma, uterine cervical carcinoma, vaginal carcinoma, vulva carcinoma, esophageal cancer, laryngeal cancer, small-intestine cancer, thyroid cancer, parathyroid cancer, soft-tissue sarcoma, urethral cancer, penile cancer, prostate cancer, chronic or acute leukemia, solid tumors in juvenile stage, differentiated lymphoma, bladder cancer, renal cancer, renal cell carcinoma, renal pelvic carcinoma, primary central nervous system lymphoma, spinal axis tumors, brain stem glioma, and pituitary adenoma, but are not limited thereto.

In one embodiment, the use of the anti-DR5 antibody or the antigen-binding fragment thereof in combination of TRAIL brings about a synergistic effect, compared to the use of the anti-DR5 antibody or the antigen-binding fragment thereof alone, and elicits an anticancer effect on TRAIL-resistant cancer as well as TRAIL-sensitive cancer (see Example 13).

Therefore, the pharmaceutical composition may comprise TRAIL (TNF-related apoptosis inducing ligand) in addition to the anti-DR5 antibody or the antigen-binding fragment thereof.

That is, the pharmaceutical composition may comprise, as effective ingredients,
(1) the anti-DR5 antibody or the antigen-binding fragment thereof; and
(2) TRAIL.

The pharmaceutical composition may comprise (1) the anti-DR5 antibody or the antigen-binding fragment thereof and (2) TRAIL in one consolidated formulation or in respective formulations.

In addition, the method for prevention and/or treatment of cancer may comprise a step of administering a pharmaceutically effective amount of TRAIL in addition to the step of administering the anti-DR5 antibody or the antigen-binding fragment thereof.

That is, the method for prevention and/or treatment of cancer may comprise a step of administering (1) a pharmaceutically effective amount of the anti-DR5 antibody or the antigen-binding fragment thereof and (2) a pharmaceutically effective amount of TRAIL, in combination, to a patient in need of prevention and/or treatment of cancer.

The combined-administration step may be conducted by administering (1) a pharmaceutically effective amount of the anti-DR5 antibody or the antigen-binding fragment thereof and (2) a pharmaceutically effective amount of TRAIL, as formulated into one dosage form, simultaneously, or (1) a pharmaceutically effective amount of the anti-DR5 antibody or the antigen-binding fragment thereof and (2) a pharmaceutically effective amount of TRAIL, as formulated into respective dosage forms, simultaneously or sequentially without regard for the order thereof.

TRAIL (TNF-related apoptosis-inducing ligand), also designated CD253 (cluster of differentiation 253) or TNFSF10 (tumor necrosis factor (ligand) superfamily, member 10), is a protein functioning as a ligand that induces the process of cell death (apoptosis). TRAIL is a cytokine that is widely produced and secreted by normal tissue cells. In one embodiment, the TRAIL may be human-derived and may be represented by, for example, NCBI Accession number NP_001177871.1, NP_003801.1, etc., but is not limited thereto.

The anti-DR5 antibody or the antigen-binding fragment thereof (or in combination with TRAIL), which takes advantage of the apoptosis pathway, may be used in combination with at least one chemotherapy agent, such as carboplatin or paclitaxel (Recka et al., Lung Cancer, 82, 441-448, 2013), gemcitabine (Torres et al., Cancer Medicine, 2(6), 925-932, 2013), etc., thereby enhancing an anticancer/anti-tumor effect (see Example 15).

In order to exert prophylactic and/or therapeutic effects on cancer, the anti-DR5 antibody or the antigen-binding fragment thereof, or a pharmaceutical composition comprising the same may be administered alone or in combination with surgery, hormone therapy, pharmacotherapy, and/or a biological response modifier.

In one embodiment, the pharmaceutical composition may comprise at least one well-known effective ingredient having an anticancer effect (chemotherapy medication) in addition to the anti-DR5 antibody or the antigen-binding fragment thereof (or in combination with TRAIL). Furthermore, the method for prevention and/or treatment of cancer may comprise a step of administering at least one well-known effective ingredient having an anticancer effect (chemotherapy medication) in addition to the anti-DR5 antibody or the antigen-binding fragment thereof (or in combination with TRAIL).

The chemotherapy medication that may be used with the anti-DR5 antibody or the antigen-binding fragment thereof may be at least one selected from the group consisting of: alkylating anticancer agents, such as carboplatin, paclitaxel (Recka et al., Lung Cancer, 82, 441-448, 2013), etc.; metabolism antagonist-based anticancer agents, such as gemcitabine (Torres et al., Cancer Medicine, 2(6), 925-932, 2013), etc.; anthracycline-based anticancer agents, such as doxorubicin (H M Amm et al., Mol Cancer Res April, 9; 403, 2011), etc.; and proteasome inhibitor-based anticancer agents, such as bortezomib (Shanker A et al., J Natl Cancer Inst, May 7; 100(9): 649-62, 2008), etc., but is not limited thereto.

For proper administration of the effective ingredients such as the anti-DR5 antibody, the antigen-binding agent, and the like, at least one pharmaceutically acceptable carrier may be included in the pharmaceutical composition or may be administered along with the effective ingredients. Examples of pharmaceutically acceptable carriers may include saline, sterilized water, Ringer's solution, buffered saline, a dextrose solution, a maltodextrin solution, glycerol, ethanol and a mixture of one or more components thereof. Other conventional additive such as antioxidants, buffers, or bacteriostats may be further added, as necessary. In addition, the pharmaceutical composition may be formulated into injectable dosage forms, such as an aqueous solution, suspension or emulsion, or into a pill, a capsule, a granule, or a tablet by adding a diluent, a dispersant, a surfactant, a binder, or a lubricant. Furthermore, the pharmaceutical composition may be properly formulated according to diseases or components, using a method pertinent to the art or disclosed in Remington's Pharmaceutical Science (latest edition), Mack Publishing Company, Easton, PA The effective ingredient such as the anti-DR5 antibody, the antigen-binding fragment, etc. or the pharmaceutical composition may be administered orally or parenterally. For parenteral administration, intravenous injection, subcutaneous injection, intramuscular injection, intraperitoneal injection, endothelial administration, topical administration, intranasal administration, intrapulmonary administration, and intrarectal administration may be conducted. Since oral administration leads to digestion of proteins or peptides, an active ingredient in the compositions for oral administration may be coated or formulated to prevent digestion in the stomach. In addition, the composition may be administered using an optional device that enables an active ingredient to be delivered to target cells.

The pharmaceutically effective amount of the anti-DR5 antibody or the antigen-binding fragment thereof may be prescribed in various amounts, depending on factors such as preparation (formulation) methods, method of administration, the patient's age, body weight, gender, pathologic conditions and diet, administration time, administration interval, administration route, excretion speed, and reaction sensitivity. For example, a daily dosage of the anti-DR5 antibody or the antigen-binding fragment thereof may be within the range of 0.001 to 1000 mg/kg, particularly 0.01 to 100 mg/kg, more particularly 0.1 to 50 mg/kg, and even more particularly 0.1 to 20 mg/kg, but is not limited thereto. The daily dosage may be formulated into a single formulation in a unit dosage form or formulated in suitably divided dosage forms, or it may be manufactured to be contained in a multiple dosage container. The pharmaceutical composition may be administered in combination with other medications, and proper prescriptions may be made on the dose, the administration method, and kinds of the other medications, depending on patients' states.

The pharmaceutical composition may be formulated into a form of a solution in oil or an aqueous medium, a suspension, syrup, an emulsion, an extract, powder, granules, a tablet, or a capsule, and may further include a dispersing or a stabilizing agent for formulation.

Particularly, the pharmaceutical composition comprising the anti-DR5 antibody or the antigen-binding fragment thereof may be formulated into an immunoliposome since it contains an antibody or an antigen-binding fragment. An antibody-containing liposome may be prepared using any of the methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the anti-DR5 antibody or the antigen-binding fragment thereof specifically binds to DR5, the antibody or fragment can be used to detect DR5 (i.e., the presence and/or level (concentration)) and/or to diagnose DR5-related diseases (i.e., the presence or changes in DR5 levels (for diseases that show increased or diseased levels relative to normal state)).

Accordingly, one embodiment envisages a DR5 detection composition comprising the anti-DR5 antibody or the antigen-binding fragment thereof. Another aspect provides a DR5 detection method comprising the steps of: treating a biological sample with the anti-DR5 antibody or the antigen-binding fragment thereof; and identifying the presence of an antigen-antibody reaction. If an antigen-antibody reaction is identified, the biological sample can be determined to contain DR5, and the level (concentration) of DR5 may be measured by measuring the extent of the antigen-antibody reaction in the biological sample.

The biological sample may be selected from the group consisting of cells, tissues, and body fluids obtained from patients (e.g., mammals such as humans), and cultures thereof. A normal sample may be selected from the group consisting of cells, tissues, and body fluids obtained from normal subjects (e.g., mammals such as humans) not suffering from a DR5-related disease, and cultures thereof.

The step of identifying the presence of an antigen-antibody reaction or the step of measuring an antigen-antibody reaction can be carried out using various methods known in the art. By way of example, an antigen-antibody reaction may be detected through an ordinary enzyme reaction, fluorescence, luminescence, and/or radioactivity detection, and particularly may be measured by a method selected from the group consisting of immunochromatography, immunohistochemistry, enzyme-linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

Another aspect provides:

a polynucleotide coding for the heavy-chain complementarity determining region, a polynucleotide coding for the light-chain complementarity determining region, or a combination thereof; a polynucleotide coding for the heavy-chain variable region, a polynucleotide coding for the light-chain variable region, or a combination thereof; or a polynucleotide coding for the heavy chain, a polynucleotide coding for the light chain, or a combination thereof, wherein the complementarity determining regions, the heavy- and light-chain variable regions, and the heavy and light chains are as described for the anti-DR5 antibody above;

a recombinant vector carrying the polynucleotides or a combination thereof; and a recombinant cell harboring the recombinant vector.

In one embodiment, the recombinant vector described above may contain polynucleotides coding respectively for a heavy-chain complementarity determining region and a light-chain complementarity determining region; for a heavy-chain variable region and a light-chain variable region; or for a heavy chain and a light chain in the anti-DR5 antibody, in a single vector or in separate vectors carrying each of the polynucleotides.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-associated virus vector. The recombinant vector may be constructed from plasmids frequently used in the art (for example, pSC101, pGV1106, pACYC177, ColE1, pKT230, µME290, pBR322, pUC8/9, pUC6, pBD9, pHC79, pIJ61, pLAFR1, pHV14, pGEX series, pET series, and pUC19), phages (for example, λgt4λB, λ-Charon, λΔz1, and M13) or by manipulating viruses (for example, SV40, etc.).

In the recombinant vector, the polynucleotide may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of the nucleotide of interest.

The recombinant vector may be constructed typically as a cloning vector or an expression vector. For recombinant expression vectors, a vector generally available in the art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pLκλ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a µMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure include *E. coli*, *Bacillus* spp. such as *Bacillus subtilis* and *Bacillus thuringiensis*, and enterobacteriaceae strains such as *Salmonella typhimurium*, *Serratia marcescens* and various *Pseudomonas* species. Eukaryotic host cells that may be used for transformation may include, but are not limited to, *Saccharomyce cerevisiae*, insect cells, and animal cells, such as Sp2/0, CHO (Chinese hamster ovary) K1, CHO DG44, PER.C6, W138, BHK, COS-7, 293, HepG2, Huh7, 3T3, RIN, and MDCK.

The nucleic acid molecule or a recombinant vector carrying the same may be introduced (transfected) into a host cell using a method well known in the art. This transfection may be carried out using a CaCl2 or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another aspect provides a method for production of an anti-DR5 antibody or an antigen-binding fragment thereof, the method comprising a step of expressing the polynucleotide or the recombinant vector in a pertinent host cell. In one embodiment, the production method may comprise culturing a recombinant cell harboring the polynucleotide or the recombinant vector thereat, and optionally isolating and/or purifying the antibody from the culture medium.

Advantageous Effects

The present disclosure provides an anti-DR5 antibody for the targeted therapy of DR5-expressing diseases. The antibody of the present disclosure is a TRAIL-uncompetitive antibody that retains a constant level of antigen binding affinity irrespective of TRAIL concentrations. Hence, the antibody can be effectively developed into innovative novel antibody drugs or diagnostic agents exhibiting superior efficacy compared to previously developed antibody drugs.

MODE FOR CARRYING OUT THE INVENTION

Figure 1:
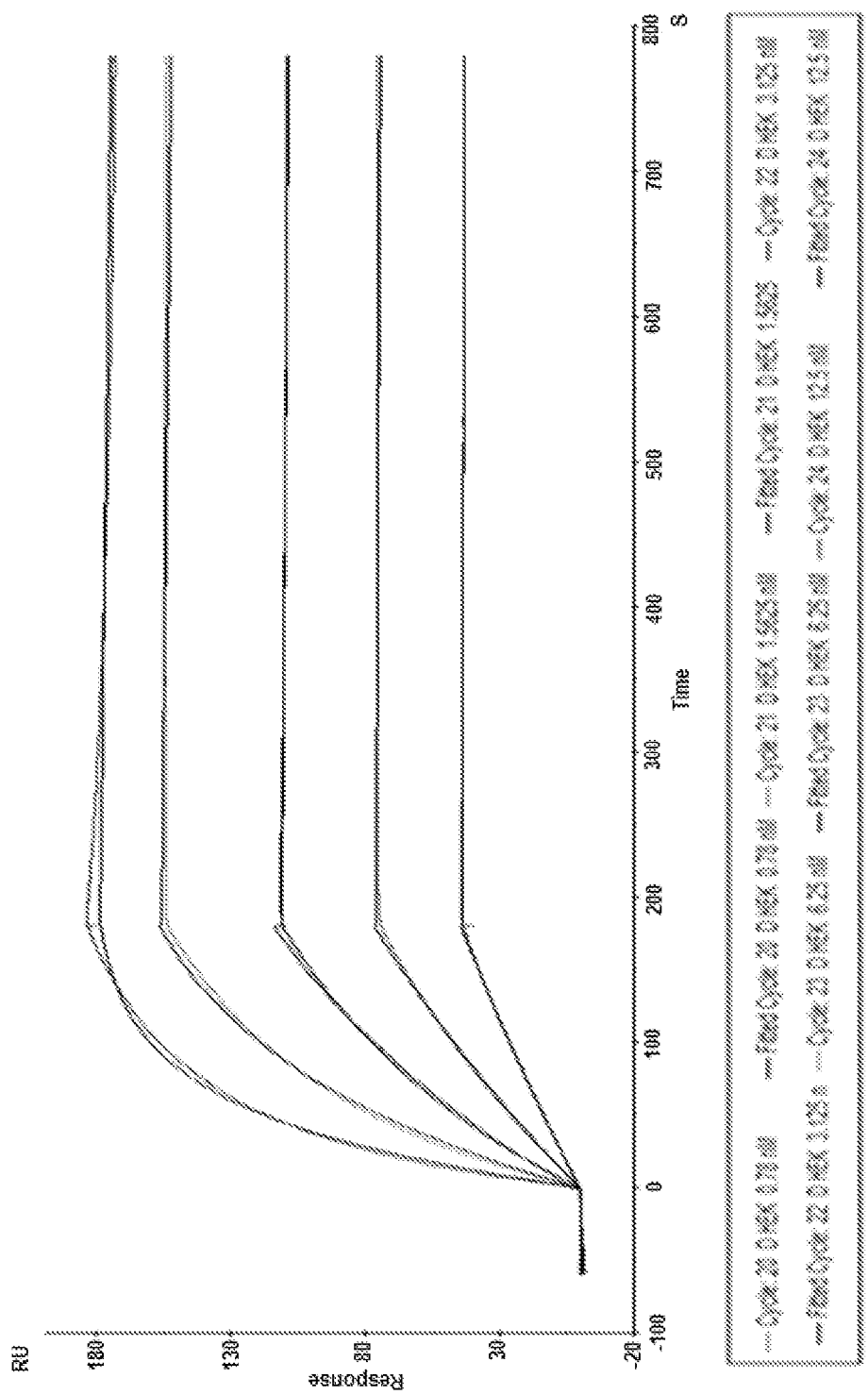
FIG. 1 is an association and dissociation sensorgram depicting association and dissociation rates of the antibody D0.
Figure 2A:
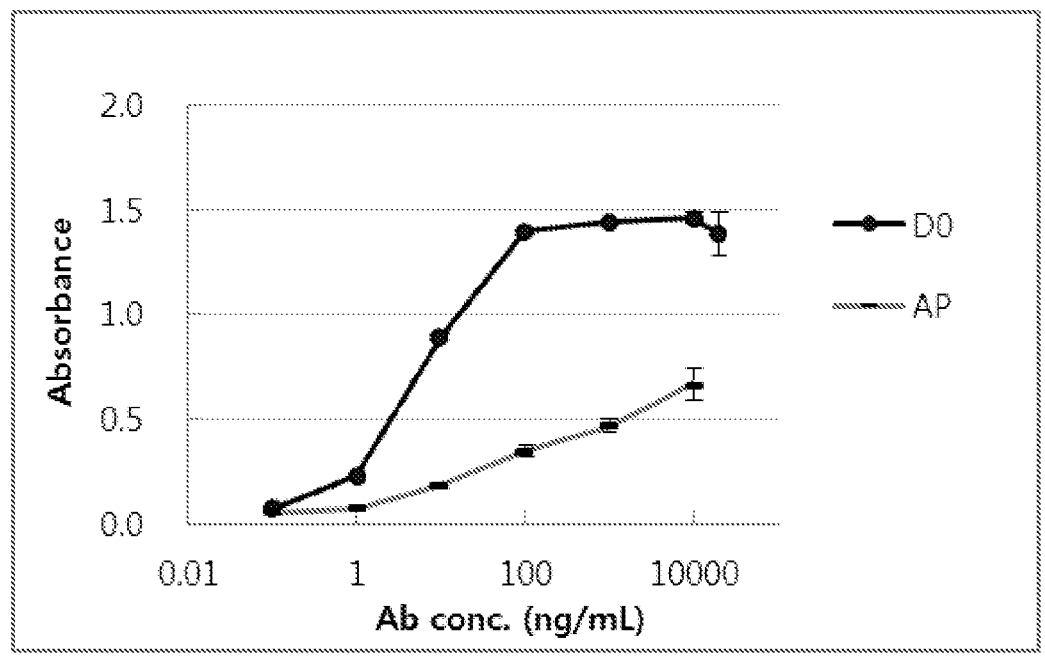
FIGS. 2a to 2f are graphs comparing antibodies D0 and DA1 to DA35 with the control antibody AP with regard to binding activity for DR5.
Figure 2B:
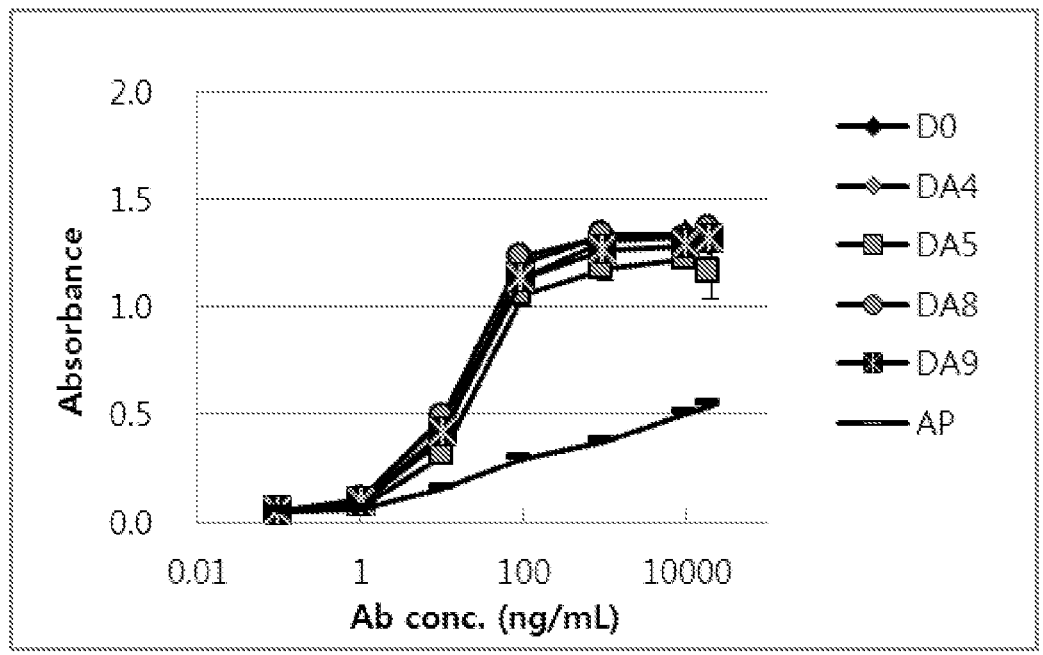
Figure 2C:
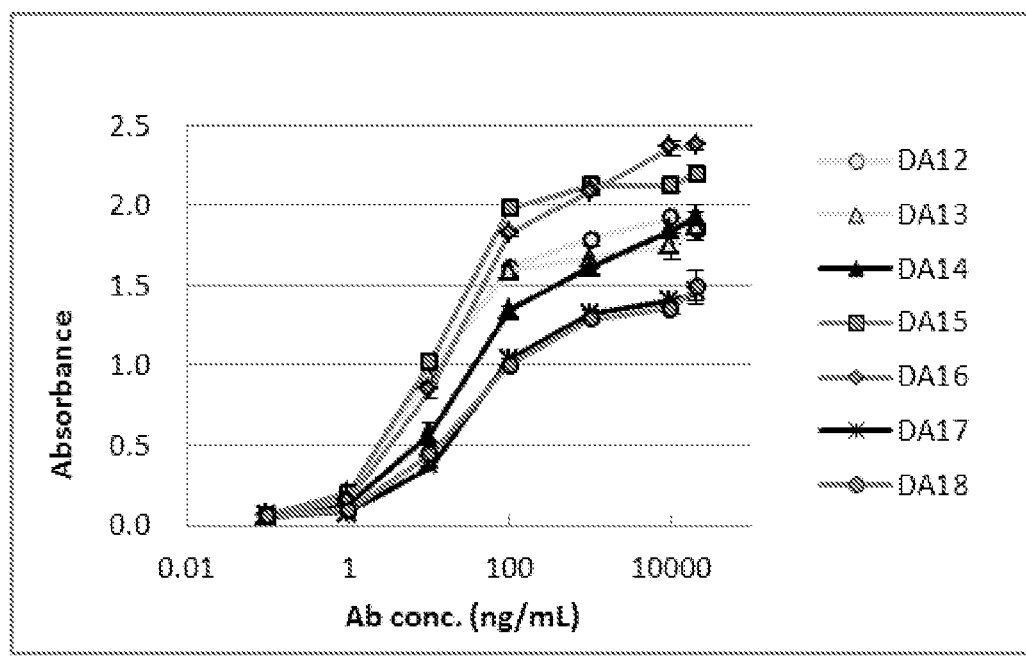
Figure 2D:
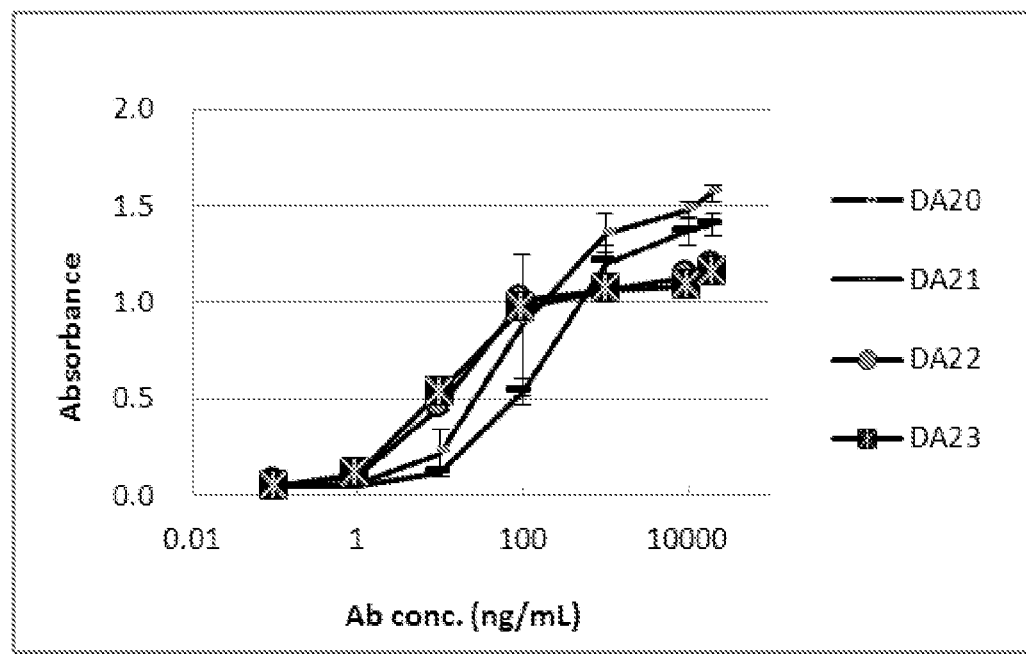
Figure 2E:
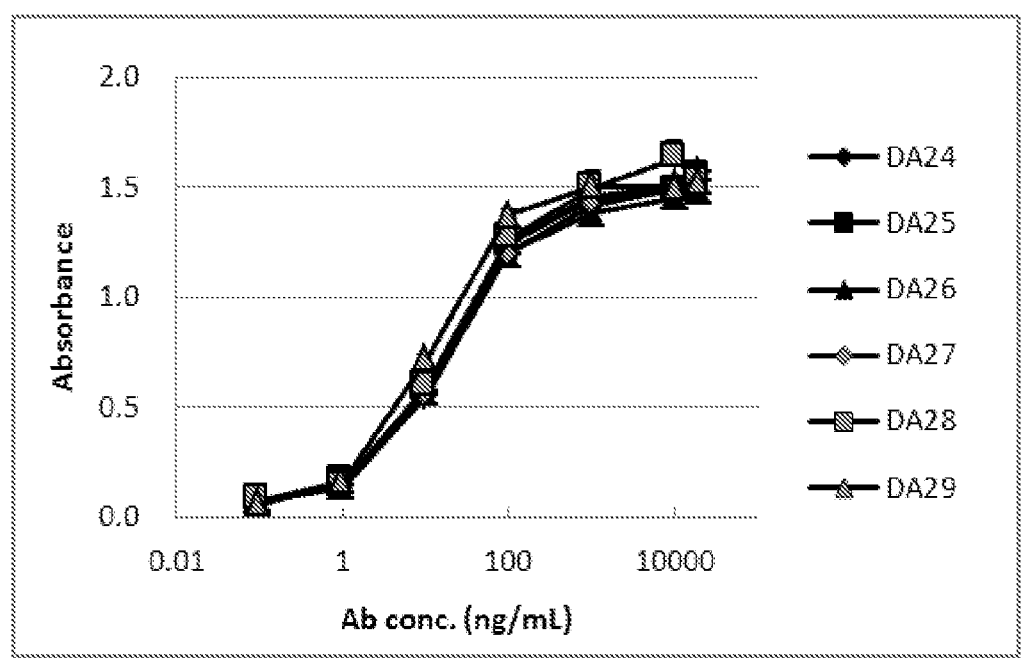
Figure 2F:
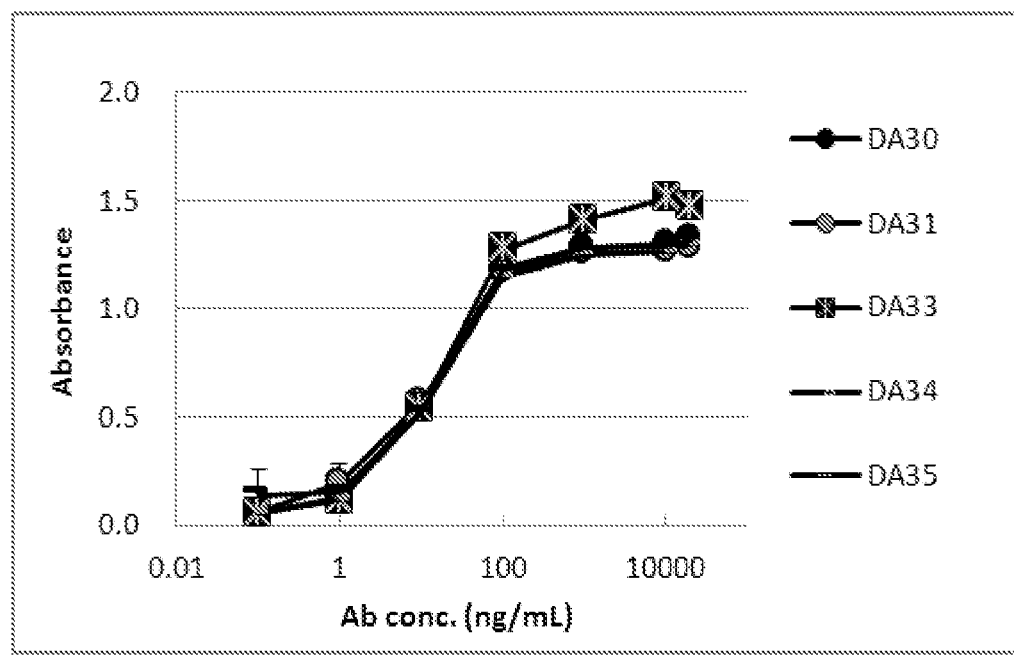

Hereinafter, the present invention will be described in detail with reference to examples. These examples are only for illustrating the present invention more specifically, and it will be apparent to those skilled in the art that the scope of the present invention is not limited by these examples.

Example 1

DR5 Immunization and cDNA Library Construction

In order to select antibodies binding specifically to DR5, animal-immunized antibody libraries were constructed. The libraries were constructed by obtaining mRNA from the immune cells of animals immunized with an antigen, amplifying an antibody gene through PCR using a combination of primers for the antibody gene, and cloning the antibody gene into phage display vectors.

Briefly, human DR5 (R&D systems, U.S.A.) in mixture with complete Freund's adjuvant and incomplete Freund's adjuvant (Sigma, U.S.A.) was subcutaneously injected to three White Leghorn chickens five times at regular intervals of three weeks. Sera from the immunized animals were diluted at a concentration of 1:100, 1:500, 1:2500, and 1:12500 in PBSB (3% bovine serum albumin in phosphate buffered saline) before being stored. Enzyme-linked immunosorbent assay was conducted to examine whether the sera bound human DR5. ELISA plates were coated overnight with 1 μg/ml human DR5 (R&D systems, U.S.A.) at 4° C., followed by reaction with the diluted sera for 2 hours. The plates were washed three times with PB ST (0.1% Tween-20 in PBS) and then incubated with anti-chicken immunoglobulin-HRP (horse radish peroxidase) (1:3000) for one hour. After three rounds of washing with PBST, color development was made for 20 min with ABTS (Thermo, U.S.A.). Absorbance at 405 nm was read on a microplate reader. Sera before immunization did not bind to DR5. Animals that produced sera with strong binding to human DR5 were selected.

Five days after the last injection, the bone marrow, spleens, and bursa of Fabricius were collected from the selected chicken. The tissues were mixed with 10 ml of TRI reagent (Molecular research center, U.S.A.) and homogenized with a homogenizer. Addition of 20 ml of TRI reagent was followed by centrifugation. The supernatant thus obtained was mixed with 3 ml of 1-bromo-3-chloropropane (BCP) and centrifuged to obtain supernatant. Total RNA was precipitated by addition of 15 ml of isopropanol. Reverse transcription was conducted using the SuperScript Transcription System (Invitrogen, U.S.A.) with random hexamers as primers (5 min at 65° C.; 5 min at 4° C.; 50 min at 50° C.; 5 min aft 85° C.; and 4° C.). 5 ul (microliters) of the reverse transcription reaction mixture containing the resulting cDNA was loaded onto 1% agarose gel and electrophoresed to detect bands of cDNA of various lengths.

Example 2

Construction of Antibody Library (2-1) Amplification of Immune Antibody Gene

In order to amplify the heavy- and light-chain variable regions $V_H$ and $V_L$ of the chicken antibody, PCR was performed as follows. For PCR, the cDNA prepared in Example 1 served as a template and combinations of primers designed for heavy-chain variable regions, light-chain variable regions, and scFv (single chain Fv) linking the heavy- and light-chain variable regions were used as shown in Table 4 below. 0.5 μl of each of the $V_H$ and $V_L$ cDNA libraries, 30 pmoles of the forward primer, 30 pmoles of the reverse primer, 10×PCR buffer, 200 μM dNTPs, and 0.5 μl Taq DNA polymerase was mixed and adjusted to a final volume of 50 μl and subjected to PCR starting with denaturation at 94° C. for 5 min, followed by 30 cycles of 94° C. for 15 sec, 56° C. for 30 sec, and 72° C. for 90 sec. PCR-amplified antibody DNA was separated according to size by 1% agarose gel electrophoresis and purified using a gel extraction kit (Qiagen, U.S.A.).

For obtaining scFv DNA, 50 ng of each of the purified $V_H$ and $V_L$ DNAs was used as a template and mixed with 30 pmoles of the forward primer, 30 pmoles of the reverse primers, 10×PCR buffer, 200 μM dNTPs, and 0.5 μl Taq DNA polymerase to a final volume of 50 μl. PCR was conducted by denaturation at 94° C. for 5 min, followed by 20 cycles of 94° C. for 30 sec, 56° C. for 30, and 72° C. for 2 min. The PCR-amplified DNA was separated according to size on a 1% agarose gel electrophoresis and purified using a gel extraction kit (Qiagen, U.S.A.).

The primers used in the PCR are summarized in Table 4 below.

TABLE 4

Primers used in PCR

| Primer | | Sequence | SEQ ID NO |
|---|---|---|---|
| $V_H$ | Forward | GGT CAG TCC TCT AGA TCT TCC GGC GGT GGTcGGC AGC TCC GGT GGT GGC GGT TCC GCC GTGcACG TTG GAC GAG | 50 |
| | Reverse | CTG GCC GGC CTG GCC ACT AGT GGA GGA GACcGAT GAC TTC GGT CC | 51 |

TABLE 4-continued

Primers used in PCR

| Primer | | Sequence | SEQ ID NO |
|---|---|---|---|
| $V_L$ | Forward | GTG GCC CAG GCG GCC CTG ACT CAG CCG TCCcTCG GTG TC | 52 |
| | Reverse | GGA AGA TCT AGA GGA CTG ACC TAG GAC GGTcCAGG | 53 |
| scFV | Forward | GAG GAG GAG GAG GAG GAG GTG GCC CAG GCG GCC CTG ACT CAG | 54 |
| | Reverse | GAG GAG GAG GAG GAG GAG GAG CTG GCC GGC CTG GCC ACT AGT GGA GG | 55 |

(2-2) Restriction Enzyme Digestion of Antibody DNA

The scFV prepared above and the phagemid vector pComb3x (the Scripps Research Institute, CA, U.S.A.) were digested with the restriction enzyme SfiI (Roche, U.S.A.). A mixture of 10 µg of the scFv-encoding PCR fragment, 360 units SfiI (Roche, U.S.A.), and 20 µl of 10× buffer was volumetrically adjusted to have a final volume of 200 µl and allowed to react overnight at 50° C. In addition, a mixture of 20 µg of the pComb3x vector, 120 units SfiI, and 20 µl of 10× buffer was volumetrically adjusted to 200 µl and reacted overnight at 50° C. Each of the resulting digests was electrophoresed on agarose gel and purified using a gel extraction kit (Qiagen, U.S.A.).

(2-3) Ligation of Antibody DNA and Library Construction

In order to insert scFv fragments into pComb3x, a mixture of 700 ng of the scFV-encoding PCR fragments digested with restriction enzyme SfiI in (2-2) and 1.4 µg of pComb3x was reacted overnight at 16° C. in the presence of T4 DNA ligase (Invitrogen, U.S.A.). The ligation mixture thus obtained was purified by ethanol precipitation and transformed into E. coli ER2738 (New England Biolab, U.S.A.) by electroporation. The E. coli were cultured in the presence of 46 µg/ml carbenicillin and 70 ug/ml kanamycin to construct a library having a complexity of $5 \times 10^9$.

Example 3

Selection of Phage Clone Carrying Anti-DR5 scFv

From the library obtained in Example 2, having randomized heavy and light chains in the form of scFV, antibodies binding to human DR5 were selected using solid phase immobilized DR5.

(3-1) Selection of Antibody Binding to DR5

First, 10 µg of human DR5 (R&D systems, U.S.A.) was conjugated to magnetic beads. An antibody DNA library was constructed by fusing the scFv-type antibodies obtained in Example 2 to phage coat protein PIII to enable expression of the antibodies on the phage surface. After being transformed with the antibody library DNA by electroporation, E. coli ER2738 (New England Biolab) was cultured at 37° C. and then incubated overnight with VCSM13 helper phage (Stratagene, U.S.A.) in the presence of 46 µg/ml carbenicillin and 70 µg/ml kanamycin in SB medium (30 g/L Tryptone, 20 g/L yeast extract, and 10 g/L MOPS, pH 7.0). The resulting culture broth containing E. coli and phages was centrifuged to precipitate and remove E. coli. The supernatant was recovered and centrifuged after addition of 40 mg/ml polyethylene glycol 8000 and 30 mg/ml NaCl. The PEG precipitated phages were collected and resuspended in PBS. The phages were reacted with human DR5 conjugated to magnetic beads at room temperature for 2 hours to capture phages having affinity for DR5. Thereafter, the beads were washed with 0.5% Tween 20 in PBS and the bound phages were eluted with 0.1M glycine (pH 2.2) and neutralized with 2M Tris. The eluted phages were allowed to infect E. coli ER2738 and cultured overnight for the next round of panning. This panning procedure was repeated four times. The repeated rounds of panning resulted in the accumulation of phages with high binding affinity. Individual clones selected from the plates of the fourth panning were incubated overnight with VCSM13 helper phage (1:1000) at 37° C. in the presence of 100 µg/ml carbenicillin and 70 µg/ml kanamycin in 96-deep well plates to induce the amplification of phages which express the antibody. After centrifugation of the resulting culture broth, the phages in the supernatant were pre-bound with TRAIL and then plated into DR5-coated ELISA plates. Incubation at 37° C. for 2 hours was followed by ELISA using an HRP-conjugated anti-M13 antibody to identify DR5-binding antibodies.

(3-2) Sequencing of Selected Antibody

E. coli ER2738 that were shown to harbor DR5-reactive clones under the selection conditions of Example (3-1) were cultured overnight in SB medium and harvested by centrifugation. Plasmid DNA was prepared using a DNA min-prep kit (GeneAll, Korea) and sequenced. For sequencing, the sequencing primers given in Table 5 below were used.

TABLE 5

Primers used in PCR

| Primer | Sequence | SEQ ID NO |
|---|---|---|
| Forward | ACA CTT TAT GCT TCC GGC TC | 56 |
| Reverse | CAA AAT CAC CGG AAC CAG AG | 57 |

Example 4

Antibody Optimization—Humanization and Affinity Improvement

Among the antibody clones obtained from the animal immunized antibody libraries, a parental clone D0 (chimeric antibody) with high affinity and activity was selected. The framework of the antibody was switched to a human antibody framework (Nishibori et al., *Molecular Immunology*, 43 (2006)). For affinity improvement, a new phage library was constructed with random mutations in the CDR sequences of the heavy and light chain regions. The phage library was obtained in the same manner as in Example 2, reacted for 2 hours at room temperature with 10 µg of human DR5 immobilized onto magnetic beads, and washed five times with 0.5% Tween 20 in PBS. Thereafter, the bound phages were eluted with 0.1 M glycine (pH 2.2) and then neutralized with 2M Tris solution. To increase the selection pressure, 1 µg of the human DR5 was immobilized to magnetic beads and washed 10 times with Tween 20 in PBS in the second round of panning, while 0.1 µg of human DR5 was immobilized and washed 20 times with Tween 20 in PBS in the third round of panning. In addition to the above humanization and affinity improvement methods, deimmunized variants were also constructed by substituting amino acids in the variable region framework sequences of the parental clone s that were predicted to have a high immunogenicity in immune cells. The humanized or deimmunized variants of the parental clone obtained as described above were designated "DA1 to DA35".

Sequences of the complementarity determining regions and variable regions obtained from D0 and DA1 to DA35 clones are summarized in Tables 6 to 9 below:

TABLE 6

Sequences of Heavy Chain CDRs

| Clone no. | SEQ ID NO | V$_H$-CDR1 | SEQ ID NO | V$_H$-CDR2 | SEQ ID NO | V$_H$-CDR3 |
|---|---|---|---|---|---|---|
| D0 | 1 | GFTFSSFNML | 2 | GIGKSDRYTGYGSAVKG | 7 | DAGSGCGSGGWTGACIDT |
| DA1 | 1 | GFTFSSFNML | 2 | GIGKSDRYTGYGSAVKG | 7 | DAGSGCGSGGWTGACIDT |
| DA2 | 1 | GFTFSSFNML | 2 | GIGKSDRYTGYGSAVKG | 7 | DAGSGCGSGGWTGACIDT |
| DA3 | 1 | GFTFSSFNML | 2 | GIGKSDRYTGYGSAVKG | 7 | DAGSGCGSGGWTGACIDT |
| DA4 | 1 | GFTFSSFNML | 2 | GIGKSDRYTGYGSAVKG | 7 | DAGSGCGSGGWTGACIDT |
| DA5 | 1 | GFTFSSFNML | 2 | GIGKSDRYTGYGSAVKG | 7 | DAGSGCGSGGWTGACIDT |
| DA6 | 1 | GFTFSSFNML | 2 | GIGKSDRYTGYGSAVKG | 7 | DAGSGCGSGGWTGACIDT |
| DA7 | 1 | GFTFSSFNML | 2 | GIGKSDRYTGYGSAVKG | 7 | DAGSGCGSGGWTGACIDT |
| DA8 | 1 | GFTFSSFNML | 2 | GIGKSDRYTGYGSAVKG | 7 | DAGSGCGSGGWTGACIDT |
| DA9 | 1 | GFTFSSFNML | 2 | GIGKSDRYTGYGSAVKG | 7 | DAGSGCGSGGWTGACIDT |
| DA10 | 1 | GFTFSSFNML | 2 | GIGKSDRYTGYGSAVKG | 7 | DAGSGCGSGGWTGACIDT |
| DA11 | 1 | GFTFSSFNML | 2 | GIGKSDRYTGYGSAVKG | 7 | DAGSGCGSGGWTGACIDT |
| DA12 | 1 | GFTFSSFNML | 2 | GIGKSDRYTGYGSAVKG | 7 | DAGSGCGSGGWTGACIDT |
| DA13 | 1 | GFTFSSFNML | 2 | GIGKSDRYTGYGSAVKG | 7 | DAGSGCGSGGWTGACIDT |
| DA14 | 1 | GFTFSSFNML | 2 | GIGKSDRYTGYGSAVKG | 7 | DAGSGCGSGGWTGACIDT |
| DA15 | 1 | GFTFSSFNML | 2 | GIGKSDRYTGYGSAVKG | 7 | DAGSGCGSGGWTGACIDT |
| DA16 | 1 | GFTFSSFNML | 2 | GIGKSDRYTGYGSAVKG | 7 | DAGSGCGSGGWTGACIDT |
| DA17 | 1 | GFTFSSFNML | 2 | GIGKSDRYTGYGSAVKG | 7 | DAGSGCGSGGWTGACIDT |
| DA18 | 1 | GFTFSSFNML | 2 | GIGKSDRYTGYGSAVKG | 7 | DAGSGCGSGGWTGACIDT |
| DA19 | 1 | GFTFSSFNML | 2 | GIGKSDRYTGYGSAVKG | 7 | DAGSGCGSGGWTGACIDT |
| DA20 | 1 | GFTFSSFNML | 2 | GIGKSDRYTGYGSAVKG | 7 | DAGSGCGSGGWTGACIDT |
| DA21 | 1 | GFTFSSFNML | 2 | GIGKSDRYTGYGSAVKG | 7 | DAGSGCGSGGWTGACIDT |

TABLE 6-continued

Sequences of Heavy Chain CDRs

| Clone no. | SEQ ID NO | V$_H$-CDR1 | SEQ ID NO | V$_H$-CDR2 | SEQ ID NO | V$_H$-CDR3 |
|---|---|---|---|---|---|---|
| DA22 | 1 | GFTFSSFNML | 2 | GIGKSDRYTGYGSAVKG | 8 | DAGSPCGSGGWTGACIDT |
| DA23 | 1 | GFTFSSFNML | 2 | GIGKSDRYTGYGSAVKG | 9 | DAGSPCGKGGWTGACIDT |
| DA24 | 1 | GFTFSSFNML | 2 | GIGKSDRYTGYGSAVKG | 7 | DAGSGCGSGGWTGACIDT |
| DA25 | 1 | GFTFSSFNML | 2 | GIGKSDRYTGYGSAVKG | 7 | DAGSGCGSGGWTGACIDT |
| DA26 | 1 | GFTFSSFNML | 2 | GIGKSDRYTGYGSAVKG | 7 | DAGSGCGSGGWTGACIDT |
| DA27 | 1 | GFTFSSFNML | 2 | GIGKSDRYTGYGSAVKG | 7 | DAGSGCGSGGWTGACIDT |
| DA28 | 1 | GFTFSSFNML | 2 | GIGKSDRYTGYGSAVKG | 7 | DAGSGCGSGGWTGACIDT |
| DA29 | 1 | GFTFSSFNML | 2 | GIGKSDRYTGYGSAVKG | 7 | DAGSGCGSGGWTGACIDT |
| DA30 | 1 | GFTFSSFNML | 2 | GIGKSDRYTGYGSAVKG | 7 | DAGSGCGSGGWTGACIDT |
| DA31 | 1 | GFTFSSFNML | 2 | GIGKSDRYTGYGSAVKG | 7 | DAGSGCGSGGWTGACIDT |
| DA32 | 1 | GFTFSSFNML | 2 | GIGKSDRYTGYGSAVKG | 7 | DAGSGCGSGGWTGACIDT |
| DA33 | 1 | GFTFSSFNML | 2 | GIGKSDRYTGYGSAVKG | 7 | DAGSGCGSGGWTGACIDT |
| DA34 | 1 | GFTFSSFNML | 2 | GIGKSDRYTGYGSAVKG | 7 | DAGSGCGSGGWTGACIDT |
| DA35 | 1 | GFTFSSFNML | 2 | GIGKSDRYTGYGSAVKG | 7 | DAGSGCGSGGWTGACIDT |

TABLE 7

Sequences of Light Chain CDRs

| Clone no. | SEQ ID NO | V$_L$-CDR1 | SEQ ID NO | V$_L$-CDR2 | SEQ ID NO | V$_L$-CDR3 |
|---|---|---|---|---|---|---|
| D0 | 4 | SGGDSYAGSYYYG | 10 | NNNNRPS | 13 | GSRDSSYVGI |
| DA1 | 4 | SGGDSYAGSYYYG | 10 | NNNNRPS | 13 | GSRDSSYVGI |
| DA2 | 4 | SGGDSYAGSYYYG | 10 | NNNNRPS | 13 | GSRDSSYVGI |
| DA3 | 4 | SGGDSYAGSYYYG | 10 | NNNNRPS | 13 | GSRDSSYVGI |
| DA4 | 4 | SGGDSYAGSYYYG | 10 | NNNNRPS | 13 | GSRDSSYVGI |
| DA5 | 4 | SGGDSYAGSYYYG | 10 | NNNNRPS | 13 | GSRDSSYVGI |
| DA6 | 4 | SGGDSYAGSYYYG | 10 | NNNNRPS | 13 | GSRDSSYVGI |

TABLE 7-continued

Sequences of Light Chain CDRs

| Clone no. | SEQ ID NO | V_L-CDR1 | SEQ ID NO | V_L-CDR2 | SEQ ID NO | V_L-CDR3 |
|---|---|---|---|---|---|---|
| DA7 | 4 | SGGDSYAGSYYYG | 10 | NNNNRPS | 13 | GSRDSSYVGI |
| DA8 | 4 | SGGDSYAGSYYYG | 10 | NNNNRPS | 13 | GSRDSSYVGI |
| DA9 | 4 | SGGDSYAGSYYYG | 10 | NNNNRPS | 13 | GSRDSSYVGI |
| DA10 | 4 | SGGDSYAGSYYYG | 10 | NNNNRPS | 13 | GSRDSSYVGI |
| DA11 | 4 | SGGDSYAGSYYYG | 10 | NNNNRPS | 13 | GSRDSSYVGI |
| DA12 | 4 | SGGDSYAGSYYYG | 11 | NNNNLMP | 13 | GSRDSSYVGI |
| DA13 | 4 | SGGDSYAGSYYYG | 10 | NNNNRPS | 14 | GSRDSAGMGA |
| DA14 | 4 | SGGDSYAGSYYYG | 12 | NNNNKAK | 13 | GSRDSSYVGI |
| DA15 | 4 | SGGDSYAGSYYYG | 10 | NNNNRPS | 15 | GSRDSDGGGR |
| DA16 | 4 | SGGDSYAGSYYYG | 10 | NNNNRPS | 16 | GSRDSSGAGG |
| DA17 | 4 | SGGDSYAGSYYYG | 12 | NNNNKAK | 13 | GSRDSSYVGI |
| DA18 | 4 | SGGDSYAGSYYYG | 10 | NNNNRPS | 15 | GSRDSDGGGR |
| DA19 | 4 | SGGDSYAGSYYYG | 11 | NNNNLMP | 13 | GSRDSSYVGI |
| DA20 | 4 | SGGDSYAGSYYYG | 10 | NNNNRPS | 14 | GSRDSAGMGA |
| DA21 | 4 | SGGDSYAGSYYYG | 10 | NNNNRPS | 16 | GSRDSSGAGG |
| DA22 | 4 | SGGDSYAGSYYYG | 10 | NNNNRPS | 13 | GSRDSSYVGI |
| DA23 | 4 | SGGDSYAGSYYYG | 10 | NNNNRPS | 13 | GSRDSSYVGI |
| DA24 | 4 | SGGDSYAGSYYYG | 10 | NNNNRPS | 13 | GSRDSSYVGI |
| DA25 | 4 | SGGDSYAGSYYYG | 10 | NNNNRPS | 13 | GSRDSSYVGI |
| DA26 | 4 | SGGDSYAGSYYYG | 10 | NNNNRPS | 13 | GSRDSSYVGI |
| DA27 | 4 | SGGDSYAGSYYYG | 10 | NNNNRPS | 13 | GSRDSSYVGI |
| DA28 | 4 | SGGDSYAGSYYYG | 10 | NNNNRPS | 13 | GSRDSSYVGI |
| DA29 | 4 | SGGDSYAGSYYYG | 10 | NNNNRPS | 13 | GSRDSSYVGI |
| DA30 | 4 | SGGDSYAGSYYYG | 10 | NNNNRPS | 13 | GSRDSSYVGI |
| DA31 | 4 | SGGDSYAGSYYYG | 10 | NNNNRPS | 13 | GSRDSSYVGI |
| DA32 | 4 | SGGDSYAGSYYYG | 10 | NNNNRPS | 13 | GSRDSSYVGI |
| DA33 | 4 | SGGDSYAGSYYYG | 10 | NNNNRPS | 13 | GSRDSSYVGI |
| DA34 | 4 | SGGDSYAGSYYYG | 10 | NNNNRPS | 13 | GSRDSSYVGI |
| DA35 | 4 | SGGDSYAGSYYYG | 10 | NNNNRPS | 13 | GSRDSSYVGI |

TABLE 8

Sequences of Heavy Chain Variable Regions

| Clone | VH-FW1 | VH-CDR1 | VH-FW2 | VH-CDR2 | VH-FW3 | VH-CDR3 | VH-FW4 | SEQ ID NO |
|---|---|---|---|---|---|---|---|---|
| D0 | AVTLDESGGGLQTPGGGLSLVCKGS | GFTFSSML | WVRQASDRYPGKTGYGLEGSAWVVKGA | GIGKGQSTVRL | RATISRDDQLNNLRAEDTGTYYCVK | DAGSGGWTGACIDT | WGHGTEVIVSS | 17 |
| DA1 | EVQLVESGGGLVQPGGSLRLSCAAS | GFTFSSML | WVRQASDRYPGKTGYGLEGSAWVVKGA | GIGKSKSTVYL | RFTISRDDQMNSLRAEDTAVYYCVR | DAGSGGWTGACIDT | WGQGTLVTVSS | 18 |
| DA2 | EVQLVESGGGLVQPGGSLRLSCAAS | GFTFSSML | WVRQASDRYPGKTGYGLEGSAWVVKGA | GIGKSKSTVYL | RFTISRDDQMNSLRAEDTAVYYCVR | DAGSGGWTGACIDT | WGQGTLVTVSS | 18 |
| DA3 | EVQLVESGGGLVQPGGSLRLSCAAS | GFTFSSML | WVRQASDRYPGKTGYGLEGSAWVVKGA | GIGKSKSTVYL | RFTISRDTQMNSLRAEDTAVYYCVR | DAGSGGWTGACIDT | WGQGTLVTVSS | 19 |
| DA4 | EVQLVESGGGLVQPGGSLRLSCAAS | GFTFSSML | WVRQASDRYPGKTGYGLEGSAWVVKGA | GIGKSKNTVYL | RFTISRDDQMNSLRAEDTAVYYCVR | DAGSGGWTGACIDT | WGQGTLVTVSS | 20 |
| DA5 | EVQLVESGGGLVQPGGSLRLSCAAS | GFTFSSML | WVRQASDRYPGKTGYGLEGSAWVVKGA | GIGKSKSTAYL | RFTISRDDQMNSLRAEDTAVYYCVR | DAGSGGWTGACIDT | WGQGTLVTVSS | 21 |
| DA6 | EVQLVESGGGLVQPGGSLRLSCAAS | GFTFSSML | WVRQASDRYPGKTGYGLEGSAWVVKGA | GIGKSKSTVYL | RFTISRDDQMNSLRAEDTAVYYCAR | DAGSGGWTGACIDT | WGQGTLVTVSS | 22 |

TABLE 8-continued

Sequences of Heavy Chain Variable Regions

| Clone | VH-FW1 | VH-CDR1 | VH-FW2 | VH-CDR2 | VH-FW3 | VH-CDR3 | VH-FW4 | SEQ ID NO |
|---|---|---|---|---|---|---|---|---|
| DA7 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCSR | WGQGTLVTVSSACIDT | 23 |
| DA8 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA9 | EVQLVESGGGLVQPGGSLRLSCAAS | GFTFSSFNML | WVRQAPGKGLEWV | GIGKSDRYTGYGSAVKG | RFTISRDDSKSTLYLQMNSLRAEDTAVYY | DAGSGCGSCVR | WGQGTLVTVSSACIDT | 24 |
| DA10 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 25 |
| DA11 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCAR | WGQGTLVTVSSACIDT | 26 |
| DA12 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 27 |
| DA13 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 27 |
| DA14 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 27 |
| DA15 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 27 |
| DA16 | EVQLVESGGGLVQPGGSLRLSCAAS | GFTFSSFNML | WVRQAPGKGLEWV | GIGKSDRYTGYGSAVKG | RFTISRDTSKNTAYLQMNSLRAEDTAVYY | DAGSGCGSCSR | WGQGTLVTVSSACIDT | 27 |
| DA17 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA18 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA19 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA20 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA21 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSGCGSCVR | WGQGTLVTVSSACIDT | 18 |
| DA22 | EVQLVESGGGLVQPGGSLRLSCAAS | GFTFSSFNML | WVRQAPGKGLEWV | GIGKSDRYTGYGSAVKG | RFTISRDDSKSTVYLQMNSLRAEDTAVYY | DAGSPCGSGCVR | WGQGTLVTVSSACIDT | 28 |
| DA23 | EVQLVESGGGLVQPGGSLRLSCAAS | GFTFSSFNML | WVRQAPGKGLEWV | GIGKSDRYTGYGSAVKG | RFTISRDDSKSTVYLCGKGWTGEDTAVYY | DAGSPCVR | WGQGTLVTVSSACIDT | 29 |
| DA24 | AVTLDESGGGLQTPGGGLSLVCKGS | GFTFSSFNML | WVRQAPGKGLEWV | GIGKGQSTVRLTGYGSAVKG | RATISRDDQLNNLRAEDTGTYY | DAGSGCGSCVK | WGHGTEVIVSSACIDT | 17 |
| DA25 | AVTLDESGGGLQTPGGGLSLVCKGS | GFTFSSFNML | WVRQAPGKGLEWV | GIGKGQSTVYLTGYGSAVKG | RATISRDDQMNSLRAEDTGTYY | DAGSGCGSCVK | WGHGTEVIVSSACIDT | 30 |
| DA26 | AVTLDESGGGLQTPGGGLSLVCKGS | GFTFSSFNML | WVRQAPGKGLEWV | GIGKGQSTVYLTGYGSAVKG | RATISRDDQMNSLRAEDTGTYY | DAGSGCGSCVK | WGHGTEVIVSSACIDT | 30 |

TABLE 8-continued

Sequences of Heavy Chain Variable Regions

| Clone | VH-FW1 | VH-CDR1 | VH-FW2 | VH-CDR2 | VH-FW3 | VH-CDR3 | VH-FW4 | SEQ ID NO |
|---|---|---|---|---|---|---|---|---|
| DA27 | AVTLD ESGGG LQTPG GGLSL VCKGS | GFT FSS FN ML | WV RQA PGK GLE WV A | GIGK SDRY TGY GSA VKG | RATISRDD GQSTVRL QLNNLRA EDTGTYY CVK | DAGS GCGS GGWT GACID T | WGH GTEV IVSS | 17 |
| DA28 | AVTLD ESGGG LQTPG GGLSL VCKGS | GFT FSS FN ML | WV RQA PGK GLE WV A | GIGK SDRY TGY GSA VKG | RATISRDD GQSTARL QLNNLRA EDTGTYY CVK | DAGS GCGS GGWT GACID T | WGH GTEV IVSS | 31 |
| DA29 | AVTLD ESGGG LQTPG GGLSL VCKGS | GFT FSS FN ML | WV RQA PGK GLE WV A | GIGK SDRY TGY GSA VKG | RATISRDD GQSTARL QLNNLRA EDTGTYY CVK | DAGS GCGS GGWT GACID T | WGH GTEV IVSS | 31 |
| DA30 | AVTLD ESGGG LQTPG GGLSL VCKGS | GFT FSS FN ML | WV RQA PGK GLE WV A | GIGK SDRY TGY GSA VKG | RATISRDD GQSTAYL QMNSLRA EDTGTYY CVK | DAGS GCGS GGWT GACID T | WGH GTEV IVSS | 32 |
| DA31 | AVTLD ESGGG LQTPG GGLSL VCKGS | GFT FSS FN ML | WV RQA PGK GLE WV A | GIGK SDRY TGY GSA VKG | RATISRDD GQSTARL QMNSLRA EDTGTYY CVK | DAGS GCGS GGWT GACID T | WGH GTEV IVSS | 33 |
| DA32 | AVTLD ESGGG LQTPG GGLSL VCKGS | GFT FSS FN ML | WV RQA PGK GLE WV A | GIGK SDRY TGY GSA VKG | RATISRDD GQSTVRL QLNNLRA EDTAVYY CVK | DAGS GCGS GGWT GACID T | WGH GTEV IVSS | 34 |
| DA33 | AVTLD ESGGG LQTPG GGLSL VCKGS | GFT FSS FN ML | WV RQA PGK GLE WV A | GIGK SDRY TGY GSA VKG | RATISRDD GQSTARL QLNNLRA EDTAVYY CVK | DAGS GCGS GGWT GACID T | WGH GTEV IVSS | 35 |
| DA34 | AVTLD ESGGG LQTPG GGLSL VCKGS | GFT FSS FN ML | WV RQA PGK GLE WV A | GIGK SDRY TGY GSA VKG | RATISRDD GQSTAYL QMNSLRA EDTAVYY CVK | DAGS GCGS GGWT GACID T | WGH GTEV IVSS | 36 |
| DA35 | AVTLD ESGGG LQTPG GGLSL VCKGS | GFT FSS FN ML | WV RQA PGK GLE WV A | GIGK SDRY TGY GSA VKG | RATISRDD GQSTARL QMNSLRA EDTAVYY CVK | DAGS GCGS GGWT GACID T | WGH GTEV IVSS | 37 |

(In Table 8 above, VH-FW1, VH-FW2, and VH-FW3 represent frameworks of the heavy-chain variable region)

TABLE 9

Sequences of Light Chain Variable Regions

| Clone | VL-FW1 | VL-CDR1 | VL-FW2 | VL-CDR2 | VL-FW3 | VL-CDR3 | VL-FW4 | SEQ ID NO |
|---|---|---|---|---|---|---|---|---|
| D0 | LTQPSS VSANL GGTVEI TC | SGG DSY AGS YY YG | WYQ QKA PGSA PVTV IY | NN NNR PS | NIPSRFSG GSR STSGSTAT DSS LTITGVQA EDEAVYF C | FGA GTT LTV GI L | | 38 |
| DA1 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA2 | DIQMT QSPSSL SASVG DRVTIT C | SGG DSY AGS YY YG | WYQ QKP GKA PKTL IY | NN NNR PS | GVPSRFSG GSR SRSGTDFT DSS LTISSLQP EDFATYY C | FGQ GTK YV VEI GI K | | 40 |
| DA3 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA4 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA5 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA6 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA7 | DIQMT QSPSSL SASVG DRVTIT C | SGG DSY AGS YY YG | WYQ QKP GKA PKTL IY | NN NNR PS | GVPSRFSG GSR STSGTDFT DSS LTISSLQP EDFATYY C | FGQ GTK YV VEI GI K | | 39 |
| DA8 | DIQMT QSPSSL SASVG DRVTIT C | SGG DSY AGS YY YG | WYQ QKP GKA PKTL IY | NN NNR PS | GVPSRFSG GSR SGSGTDFT DSS LTISSLQP EDFATYY C | FGQ GTK YV VEI GI K | | 41 |
| DA9 | DIQMT QSPSSL SASVG DRVTIT C | SGG DSY AGS YY YG | WYQ QKP GKA PKTL IY | NN NNR PS | GVPSRFSG GSR SRSGTDFT DSS LTISSLQP EDFATYY C | FGQ GTK YV VEI GI K | | 40 |
| DA10 | DIQMT QSPSSL SASVG DRVTIT C | SGG DSY AGS YY YG | WYQ QKP GKA PKTL IY | NN NNR PS | GVPSRFSG GSR SRSGTDFT DSS LTISSLQP EDFATYY C | FGQ GTK YV VEI GI K | | 40 |
| DA11 | DIQMT QSPSSL SASVG DRVTIT C | SGG DSY AGS YY YG | WYQ QKP GKA PKTL IY | NN NNR PS | GVPSRFSG GSR SRSGTDFT DSS LTISSLQP EDFATYY C | FGQ GTK YV VEI GI K | | 40 |

TABLE 9-continued

Sequences of Light Chain Variable Regions

| Clone | VL-FW1 | VL-CDR1 | VL-FW2 | VL-CDR2 | VL-FW3 | VL-CDR3 | VL-FW4 | SEQ ID NO |
|---|---|---|---|---|---|---|---|---|
| DA12 | DIQMTQSPSSLSASVGDRVTITC | SGGDSYAGSYYYG | WYQQKPGKAPKTLIY | NNNLMP | GVPSRFSGGSRSRSGTDFTLTISSLQPEDFATYYC | DSSYV | FGQGTKVEIK | 42 |
| DA13 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSAGM | FGQGTKVEIK | 43 |
| DA14 | DIQMTQSPSSLSASVGDRVTITC | SGGDSYAGSYYYG | WYQQKPGKAPKTLIY | NNKAK | GVPSRFSGGSRSRSGTDFTLTISSLQPEDFATYYC | DSSYV | FGQGTKVEIK | 44 |
| DA15 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSDGR | FGQGTKVEIK | 45 |
| DA16 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSSGA | FGQGTKVEIK | 46 |
| DA17 | DIQMTQSPSSLSASVGDRVTITC | SGGDSYAGSYYYG | WYQQKPGKAPKTLIY | NNKAK | GVPSRFSGGSRSRSGTDFTLTISSLQPEDFATYYC | DSSYV | FGQGTKVEIK | 44 |
| DA18 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSDGR | FGQGTKVEIK | 45 |
| DA19 | DIQMTQSPSSLSASVGDRVTITC | SGGDSYAGSYYYG | WYQQKPGKAPKTLIY | NNLMP | GVPSRFSGGSRSRSGTDFTLTISSLQPEDFATYYC | DSSYV | FGQGTKVEIK | 42 |
| DA20 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSAGM | FGQGTKVEIK | 43 |
| DA21 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSSGA | FGQGTKVEIK | 46 |
| DA22 | DIQMTQSPSSLSASVGDRVTITC | SGGDSYAGSYYYG | WYQQKPGKAPKTLIY | NNRPS | STSGTDFTLTISSLQPEDFATYYC | DSSYV | FGQGTKVEIK | 47 |
| DA23 | DIQMTQSPSSLSASVGDRVTITC | SGGDSYAGSYYYG | WYQQKPGKAPKTLIY | NNRPS | GVPSRFSGGSRSRSGTDFTLTISSLQPEDFATYYC | DSSYV | FGQGTKVEIK | 47 |
| DA24 | LTQPSSVSANLGGTVEITC | SGGDSYAGSYYYG | WYQQKAPGSAPVTVIY | NNRPS | NIPSRFSGGSRSTSGSTATLTITGVQAEDEATYYC | DSSYV | FGAGTTLTVL | 48 |
| DA25 | LTQPSSVSANLGGTVEITC | SGGDSYAGSYYYG | WYQQKAPGSAPVTVIY | NNRPS | NIPSRFSGGSRSTSGSTATLTITGVQAEDEAVYFC | DSSYV | FGAGTTLTVL | 38 |
| DA26 | LTQPSSVSANLGGTVEITC | SGGDSYAGSYYYG | WYQQKAPGSAPVTVIY | NNRPS | NIPSRFSGGSRSTSGSTATLTITGVQAEDEATYYC | DSSYV | FGAGTTLTVL | 48 |
| DA27 | LTQPSSVSANLGGTVEITC | SGGDSYAGSYYYG | WYQQKAPGSAPVTVIY | NNRPS | NIPSRFSGGSRSTSGSTATLTITGVQAEDEATYFC | DSSYV | FGAGTTLTVL | 49 |
| DA28 | LTQPSSVSANLGGTVEITC | SGGDSYAGSYYYG | WYQQKAPGSAPVTVIY | NNRPS | NIPSRFSGGSRSTSGSTATLTITGVQAEDEAVYFC | DSSYV | FGAGTTLTVL | 38 |
| DA29 | LTQPSSVSANLGGTVEITC | SGGDSYAGSYYYG | WYQQKAPGSAPVTVIY | NNRPS | NIPSRFSGGSRSTSGSTATLTITGVQAEDEATYFC | DSSYV | FGAGTTLTVL | 49 |
| DA30 | LTQPSSVSANLGGTVEITC | SGGDSYAGSYYYG | WYQQKAPGSAPVTVIY | NNRPS | NIPSRFSGGSRSTSGSTATLTITGVQAEDEATYYC | DSSYV | FGAGTTLTVL | 48 |
| DA31 | LTQPSSVSANLGGTVEITC | SGGDSYAGSYYYG | WYQQKAPGSAPVTVIY | NNRPS | NIPSRFSGGSRSTSGSTATLTITGVQAEDEATYFC | DSSYV | FGAGTTLTVL | 49 |
| DA32 | LTQPSSVSANLGGTVEITC | SGGDSYAGSYYYG | WYQQKAPGSAPVTVIY | NNRPS | NIPSRFSGGSRSTSGSTATLTITGVQAEDEAVYFC | DSSYV | FGAGTTLTVL | 38 |
| DA33 | LTQPSSVSANLGGTVEITC | SGGDSYAGSYYYG | WYQQKAPGSAPVTVIY | NNRPS | NIPSRFSGGSRSTSGSTATLTITGVQAEDEATYFC | DSSYV | FGAGTTLTVL | 49 |
| DA34 | LTQPSSVSANLGGTVEITC | SGGDSYAGSYYYG | WYQQKAPGSAPVTVIY | NNRPS | NIPSRFSGGSRSTSGSTATLTITGVQAEDEATYYC | DSSYV | FGAGTTLTVL | 48 |

TABLE 9-continued

Sequences of Light Chain Variable Regions

| Clone | VL-FW1 | VL-CDR1 | VL-FW2 | VL-CDR2 | VL-FW3 | VL-CDR3 | VL-FW4 | SEQ ID NO |
|---|---|---|---|---|---|---|---|---|
| DA35 | LTQPSS VSANL GGTVEI TC | SGG DSY AGS YY YG | WYQ QKA PGSA PVTV IY | NN NNR PS | NIPSRFSG STSGSTAT LTITGVQA EDEATYF C | GSR DSS YV GI | FGA GTT LTV L | 49 |

(In Table 9, VL-FW1, VL-FW2, and VL-FW3 represent frameworks of the light-chain variable region)

Example 5

Production of Antibody

Immunoglobulin (IgG) proteins were produced for use in assaying the affinity and activity of the antibodies obtained above. From pComb3x carrying the scFv nucleotide, variable and constant region fragments of the heavy and light chains were obtained by PCR using the primer combinations shown in Table 10 and the condition used in Example 2.

Genes of variable regions ($V_H$ to $V_L$) and constant regions ($C_H$ to $C_k$) in the heavy and light chains were amplified by PCR using the combinations of HC and LC primers in Table 10 and inserted into mammalian cell expression plasmids using the pcDNA™3.3-TOPO® TA cloning kit and pOpti™VEC-TOPO® TA cloning kit (Invitrogen, U.S.A.). 1 µl of each of the vectors (pcDNA™3.3-TOPO® vector and pOpti™ VEC-TOPO® vector) and fragments were added to a buffer containing 200 mM NaCl and 10 mM $MgCl_2$ to a final volume of 6 µl and reacted at room temperature for 5 min. The vectors were transformed into DH5α E. coli competent cells by heat shock. The resultant colonies were mass cultured to obtain plasmids. The plasmids prepared above were transfected into HEK293F cells (Invitrogen, U.S.A.), which were than cultured for 7 days to express the antibodies. The antibodies were purified using a protein A column (GE, U.S.A.). Cell culture supernatants were loaded onto the column to bind the antibodies (IgG) to protein A, followed by elution with 20 mM sodium citrate buffer (pH 3.0). The antibodies were confirmed by SDS-PAGE to have high purity and light chain and heavy chain molecular weights in accordance with the theoretical size.

TABLE 10

| Primer | | Sequence | SEQ ID NO |
|---|---|---|---|
| $V_H$ | Forward | GCT AGC CGC CAC CAT GGG C | 58 |
| | Reverse | AGG GGC CCT TGG TGG AGG CCT GGC CGG CCT GGC CAC T | 59 |
| $C_H$ | Forward | GCC TCC ACC AAG GGC CCC TC | 60 |
| | Reverse | CGG GAT CCC TTG CCG GCC GT | 61 |
| HC (Heavy Chain) | Forward | GCT AGC CGC CAC CAT GGG C | 62 |
| | Reverse | CGG GAT CCC TTG CCG GCC GT | 63 |
| $V_L$ | Forward | AAG CTT GCC GCC ACC ATG | 64 |
| | Reverse | AGG GGG CGG CCA CGG TCC GGG AAG ATC TAG AGG ACT G | 65 |

TABLE 10-continued

| Primer | | Sequence | SEQ ID NO |
|---|---|---|---|
| $C_k$ | Forward | CGG ACC GTG GCC GCC CCC TC | 66 |
| | Reverse | GCT CTA GAC TAG CAC TCG C | 67 |
| LC (Light Chain) | Forward | AAG CTT GCC GCC ACC ATG | 68 |
| | Reverse | GCT CTA GAC TAG CAC TCG C | 69 |

Example 6

Assay of Binding Affinity of Antibody to Human DR5

In order to measure affinity, human DR5 was coupled to carboxylated dextran biosensor chips (CM5, GE) according to the manufacturer's instruction. Association and dissociation rates were assessed by injecting IgG proteins that were 2-fold serially diluted to 5 nM, 2.5 nM, 1.25 nM, 0.625 nM, 0.313 nM, and 0.156 nM.

Association and dissociation rates were depicted in association and dissociation sensorgrams and calculated using a simple 1:1 Langmuir binding model (BIAcore X100 Evaluation Software, ver. 2.0). The equilibrium dissociation constants (KD), which is the ratio of dissociation constant (Kd) to association constant (Ka), were confirmed to be in the sub-nanomolar range. Measurements of the binding of antibody D0 and DA1 to DA35 of the present disclosure to DR5 are given in Table 11 below (antibody names are given as the names of the clones from which the antibodies were derived). A representative sensorgram for D0 is depicted in FIG. 1.

TABLE 11

| Antibody | Binding Molecule | Ka(1/Ms) | Kd(1/s) | KD(M) |
|---|---|---|---|---|
| D0 | Human DR5 | $1.49 \times 10^{6}$ | $2.26 \times 10^{-5}$ | $1.52 \times 10^{-11}$ |
| DA1 | Human DR5 | $4.90 \times 10^{6}$ | $1.80 \times 10^{-9}$ | $3.80 \times 10^{-16}$ |
| DA2 | Human DR5 | $1.90 \times 10^{6}$ | $4.90 \times 10^{-10}$ | $2.10 \times 10^{-16}$ |
| DA3 | Human DR5 | $4.90 \times 10^{6}$ | $1.80 \times 10^{-9}$ | $3.80 \times 10^{-16}$ |
| DA4 | Human DR5 | $1.20 \times 10^{6}$ | $1.20 \times 10^{-7}$ | $1.00 \times 10^{-13}$ |
| DA5 | Human DR5 | $1.20 \times 10^{6}$ | $2.60 \times 10^{-9}$ | $2.10 \times 10^{-15}$ |
| DA6 | Human DR5 | $7.80 \times 10^{6}$ | $4.20 \times 10^{-6}$ | $5.30 \times 10^{-13}$ |
| DA7 | Human DR5 | $1.40 \times 10^{6}$ | $2.90 \times 10^{-6}$ | $1.90 \times 10^{-12}$ |
| DA8 | Human DR5 | $1.60 \times 10^{6}$ | $2.20 \times 10^{-8}$ | $1.30 \times 10^{-14}$ |
| DA9 | Human DR5 | $5.60 \times 10^{6}$ | $4.00 \times 10^{-7}$ | $7.10 \times 10^{-14}$ |
| DA10 | Human DR5 | $2.30 \times 10^{6}$ | $1.60 \times 10^{-5}$ | $7.00 \times 10^{-12}$ |
| DA12 | Human DR5 | $2.37 \times 10^{06}$ | $2.99 \times 10^{-5}$ | $1.27 \times 10^{-11}$ |
| DA13 | Human DR5 | $2.62 \times 10^{06}$ | $2.94 \times 10^{-5}$ | $1.12 \times 10^{-11}$ |
| DA14 | Human DR5 | $4.27 \times 10^{06}$ | $1.00 \times 10^{-4}$ | $2.35 \times 10^{-11}$ |
| DA15 | Human DR5 | $2.56 \times 10^{06}$ | $2.78 \times 10^{-6}$ | $1.09 \times 10^{-12}$ |
| DA16 | Human DR5 | $2.11 \times 10^{06}$ | $5.53 \times 10^{-5}$ | $2.61 \times 10^{-11}$ |
| DA17 | Human DR5 | $2.54 \times 10^{06}$ | $5.97 \times 10^{-5}$ | $2.35 \times 10^{-11}$ |
| DA18 | Human DR5 | $1.33 \times 10^{06}$ | $3.67 \times 10^{-5}$ | $2.77 \times 10^{-11}$ |
| DA20 | Human DR5 | $1.00 \times 10^{06}$ | $1.21 \times 10^{-5}$ | $1.20 \times 10^{-11}$ |
| DA21 | Human DR5 | $1.11 \times 10^{06}$ | $7.17 \times 10^{-6}$ | $6.43 \times 10^{-12}$ |
| DA22 | Human DR5 | $9.32 \times 10^{05}$ | $3.19 \times 10^{-5}$ | $3.42 \times 10^{-11}$ |
| DA23 | Human DR5 | $6.96 \times 10^{05}$ | $2.80 \times 10^{-5}$ | $4.03 \times 10^{-11}$ |
| DA24 | Human DR5 | $1.20 \times 10^{06}$ | $1.23 \times 10^{-6}$ | $1.02 \times 10^{-12}$ |
| DA25 | Human DR5 | $1.05 \times 10^{06}$ | $1.71 \times 10^{-6}$ | $1.62 \times 10^{-12}$ |
| DA26 | Human DR5 | $1.09 \times 10^{06}$ | $1.10 \times 10^{-6}$ | $1.01 \times 10^{-12}$ |
| DA27 | Human DR5 | $1.17 \times 10^{06}$ | $2.24 \times 10^{-6}$ | $1.92 \times 10^{-12}$ |
| DA28 | Human DR5 | $1.16 \times 10^{06}$ | $4.52 \times 10^{-6}$ | $3.89 \times 10^{-12}$ |
| DA29 | Human DR5 | $1.21 \times 10^{06}$ | $8.47 \times 10^{-5}$ | $6.98 \times 10^{-11}$ |
| DA30 | Human DR5 | $1.03 \times 10^{06}$ | $7.97 \times 10^{-5}$ | $7.74 \times 10^{-11}$ |
| DA31 | Human DR5 | $1.24 \times 10^{06}$ | $8.79 \times 10^{-5}$ | $7.06 \times 10^{-11}$ |
| DA32 | Human DR5 | $1.14 \times 10^{06}$ | $8.59 \times 10^{-5}$ | $7.51 \times 10^{-11}$ |
| DA33 | Human DR5 | $1.24 \times 10^{06}$ | $9.77 \times 10^{-5}$ | $7.88 \times 10^{-11}$ |

TABLE 11-continued

| Antibody | Binding Molecule | Ka(1/Ms) | Kd(1/s) | KD(M) |
|---|---|---|---|---|
| DA34 | Human DR5 | 1.00 × 10^06 | 9.50 × 10^−5 | 9.42 × 10^−11 |
| DA35 | Human DR5 | 1.13 × 10^06 | 9.12 × 10^−05 | 8.01 × 10^−11 |

Example 7

Assay of Binding Activity of Antibodies for Human DR5

The binding activities of the antibodies of the present disclosure were for human DR5 were confirmed by enzyme-linked immunosorbent assay. Human DR5 protein at a concentration of 10 ng/ml was plated at a volume of 150 µl per well onto 96-well immune plates (Nunc, U.S.A.) and adsorbed at room temperature for one hour. After the plates were washed three times with a buffer solution, serial dilutions (0.1-2000 ng/ml) of the antibodies were added to the wells at 150 µl per well and incubated at room temperature for 1-2 hours. The plates were washed again with a buffer solution. Then, HRP (horseradish peroxidase)-conjugated antibody (Serotec, U.S.A.) against anti-human immunoglobulin Fc was 1:20,000 diluted and plated at a volume of 150 µl per well, followed by incubation at room temperature for 1 hour. After washing, a 3,3',5,5'-tetramethylbenzidine (TMB; Sigma, U.S.A.) solution was added at an amount of 100 µl per well and incubated for 3 to 10 min for color development. When the color development reached a certain level, the reaction was terminated with 1 N sulfuric acid ($H_2SO_4$). Absorbance at 450 nm was read using a spectrophotometer (Molecular Device, U.S.A.) and the results are depicted in FIGS. 2a to 2f. In this assay, the antibody AP was synthesized according to the anti-DR5 antibody sequence disclosed in PCT/US2006/03577 (WO 2006/083971) and used as a control antibody. As can be seen in FIGS. 2a to 2f, antibodies D0 and DA1 to DA35 were observed to have higher antigen binding activity compared to the control antibody AP.

Example 8

Analysis of Physicochemical Properties

[8-1] Confirmation of Antibody Size

Figure 3A:
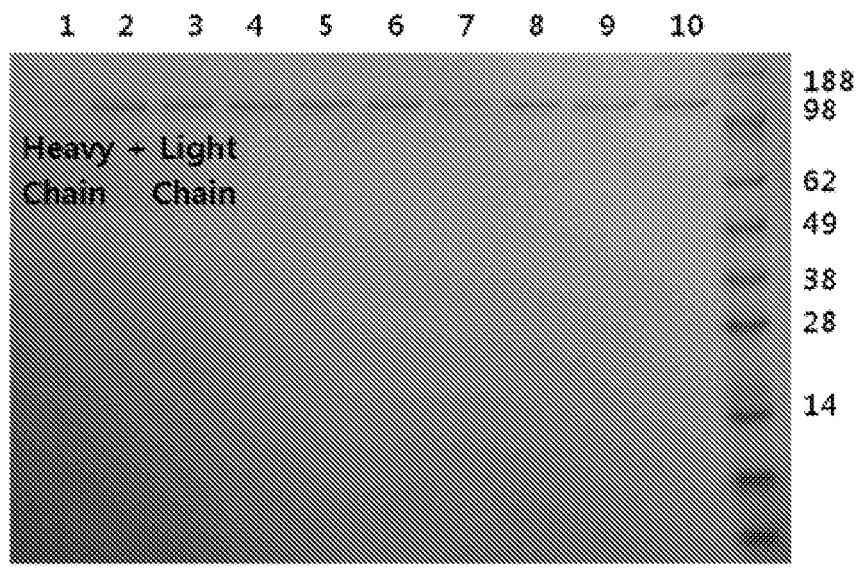
FIGS. 3a and 3b exhibit SDS-polyacrylamide gel electrophoresis (SDS-PAGE) results of representative antibodies according to the present disclosure.
Figure 3B:
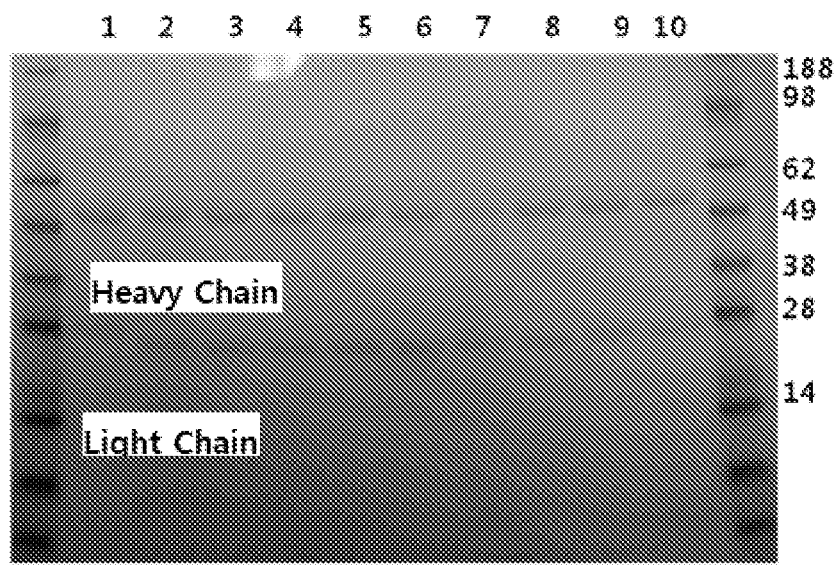

The sizes of the antibodies according to the present disclosure were analyzed by SDS-PAGE using NuPAGE 4-12% Bis-Tris gel (Invitrogen, U.S.A.). The prepared anti-DR5 antibodies (D0, DA1, DA4, DA16, DA18, DA20, DA23, DA26, and DA29) were subjected to SDS-polyacrylamide gel electrophoresis (SDS-PAGE) at reduced conditions after treatment with DTT (Invitrogen, U.S.A.) to remove disulfide bonds, and at non-reduced conditions without DTT treatment, to identify the presence of light and heavy chains of the complete antibody. The results are depicted in FIGS. 3a (non-reduced condition) and 3b (reduced condition). As shown in FIG. 3a, for samples analyzed at non-reduced conditions, a band was detected at a position between a 98 kDa size marker and a 188 kDa size marker, which corresponds to the size of the complete antibody. As shown in FIG. 3b, for samples analyzed at reduced conditions, two bands were detected at vicinities of a 49 kDa size marker and a 28 kDa size marker, which correspond to the heavy and light chain of the antibodies, respectively. Thus, bands corresponding to the entire antibody, the heavy chain, and the light chain were each detected by SDS-polyacrylamide gel electrophoresis.

[8-2] Confirmation of Antibody Purity

Figure 4A:
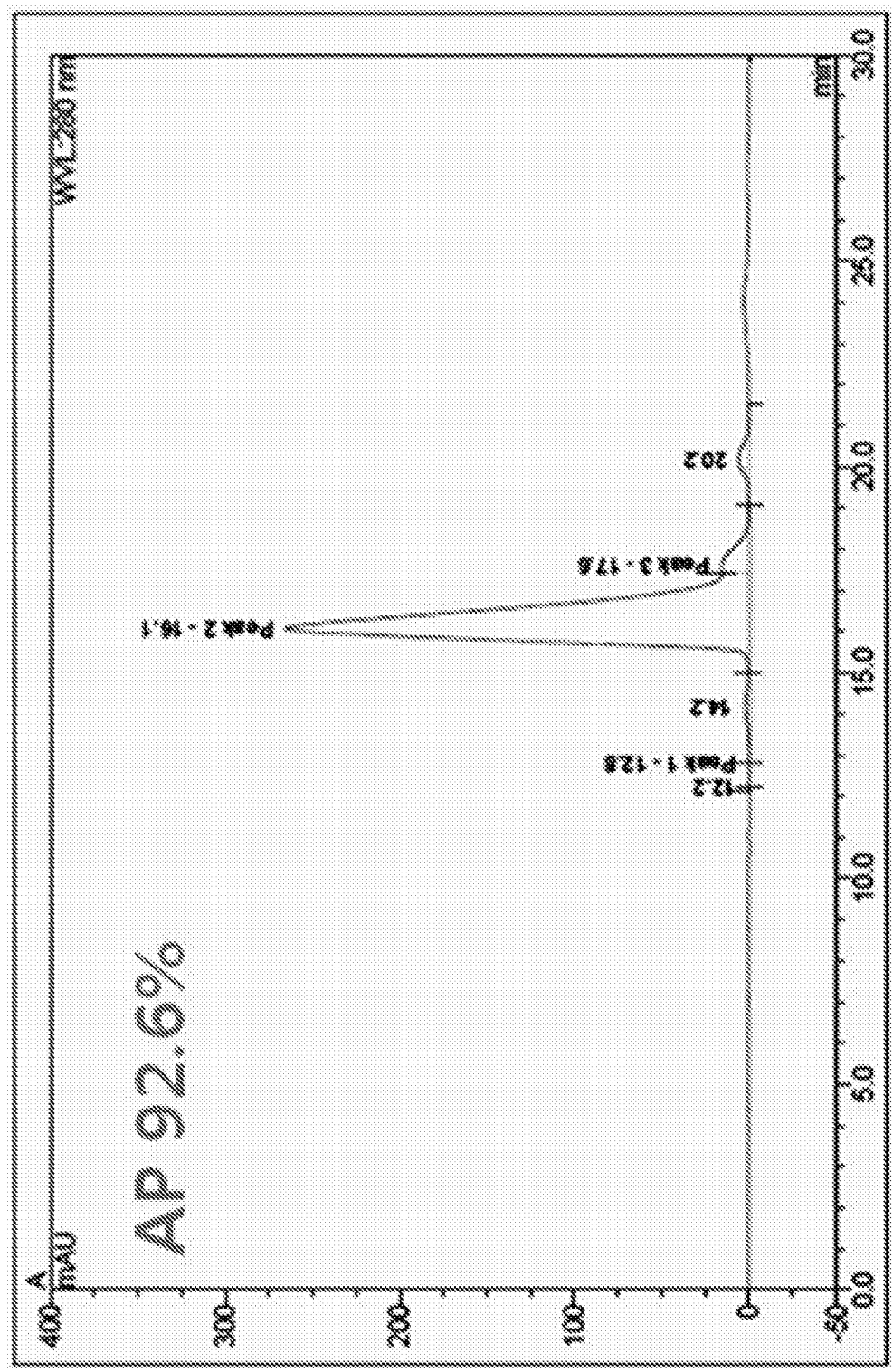
FIGS. 4a to 4h are size exclusion chromatograms (SEC) of representative antibodies according to the present disclosure.
Figure 4B:
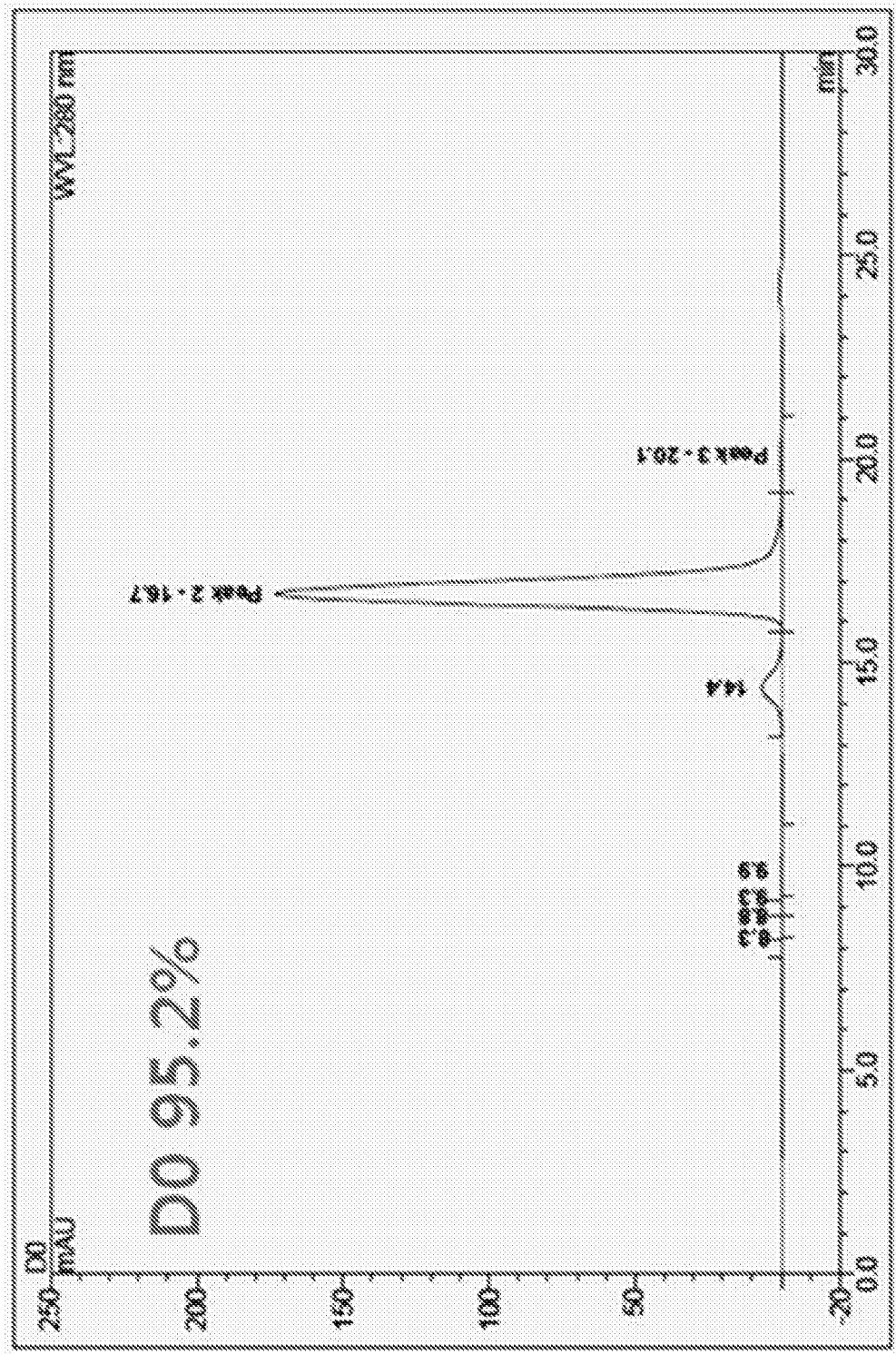
Figure 4C:
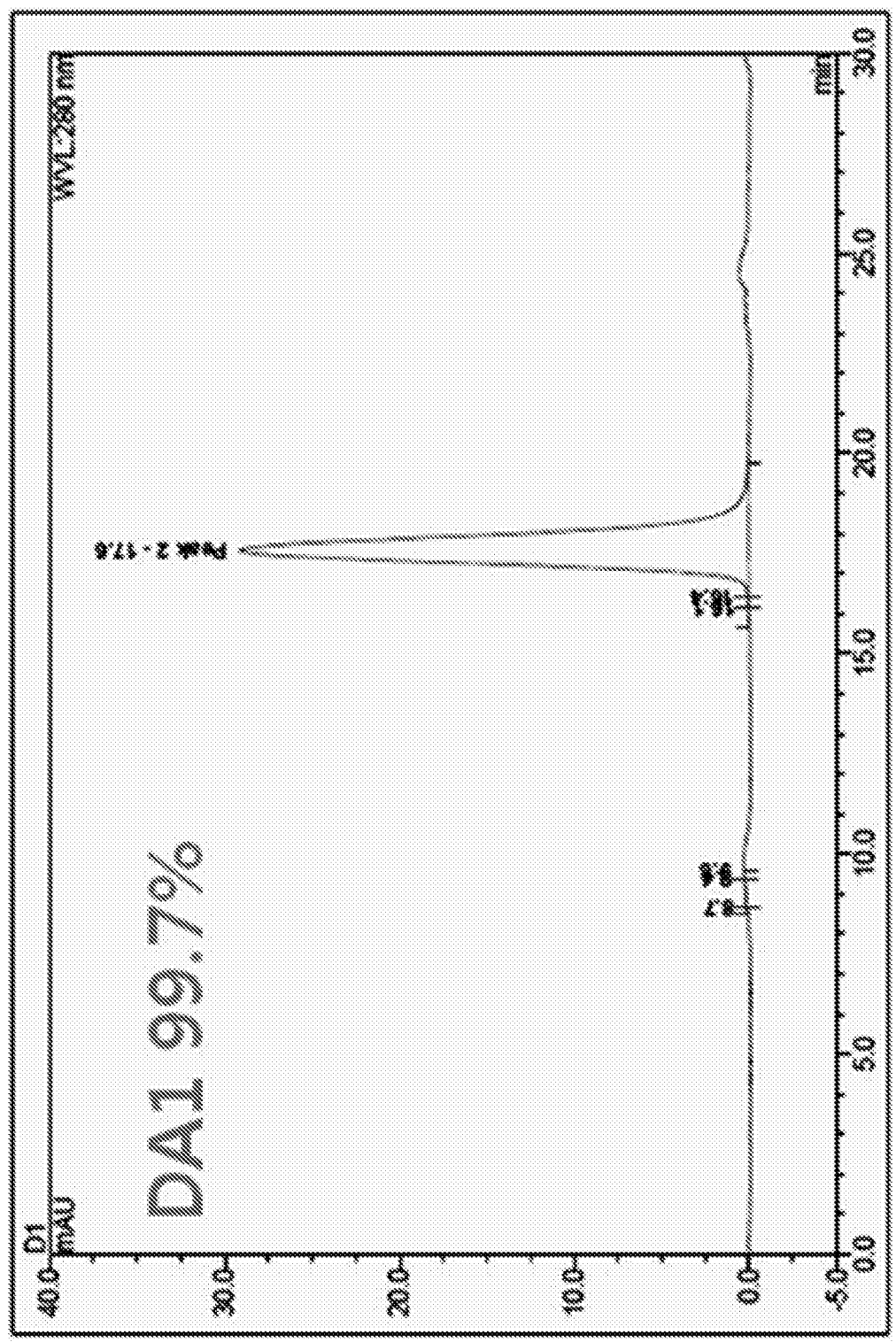
Figure 4D:
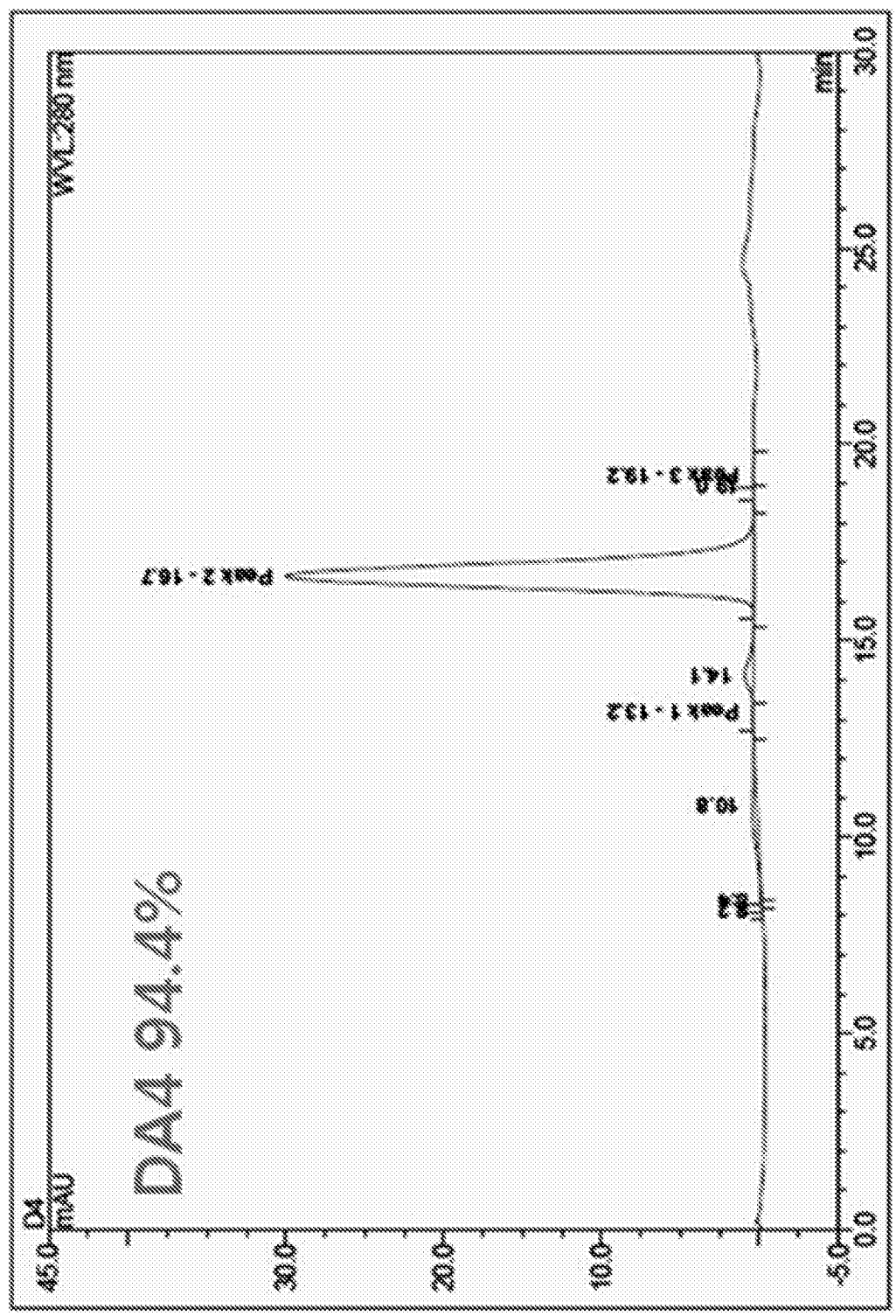
Figure 4E:
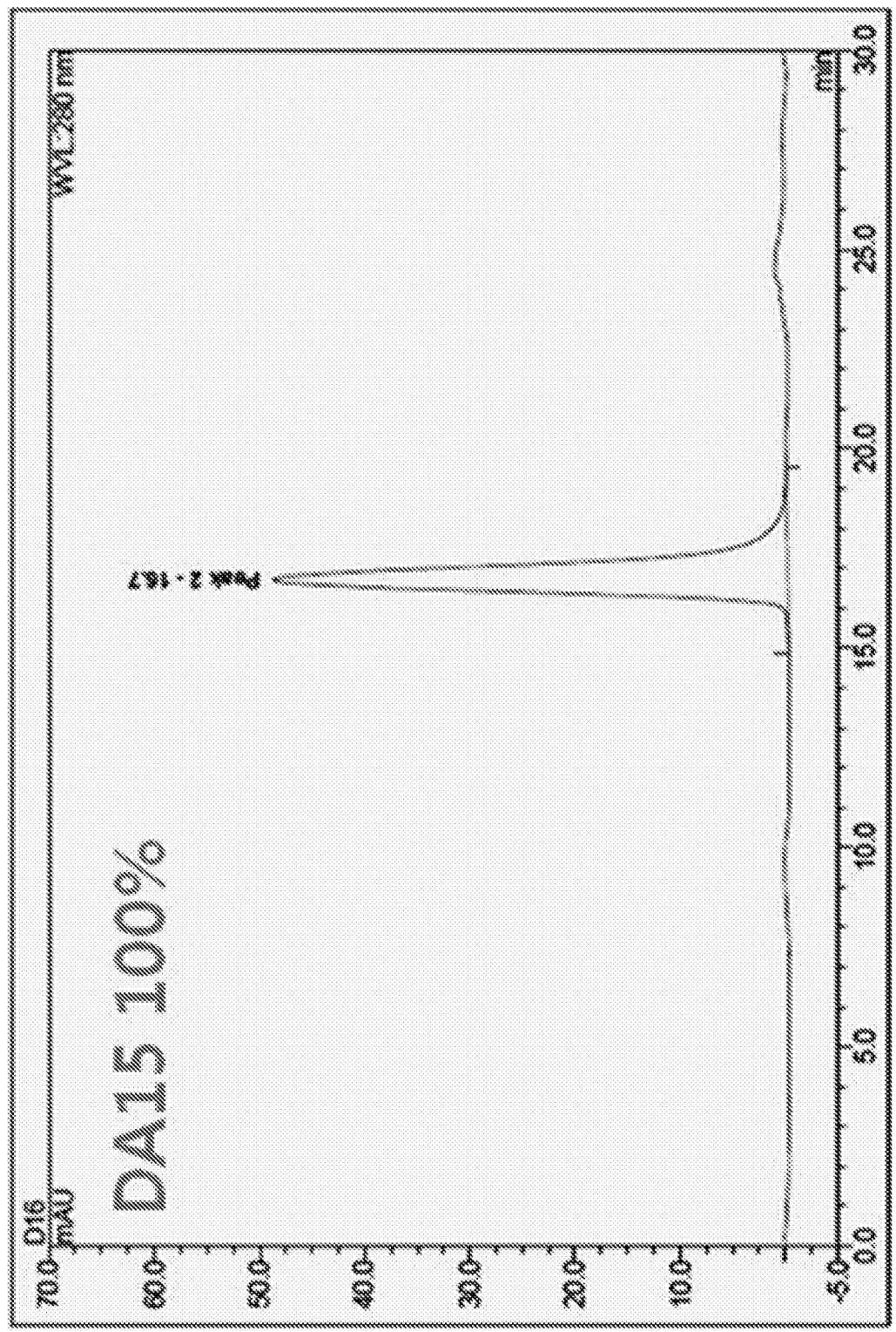
Figure 4F:
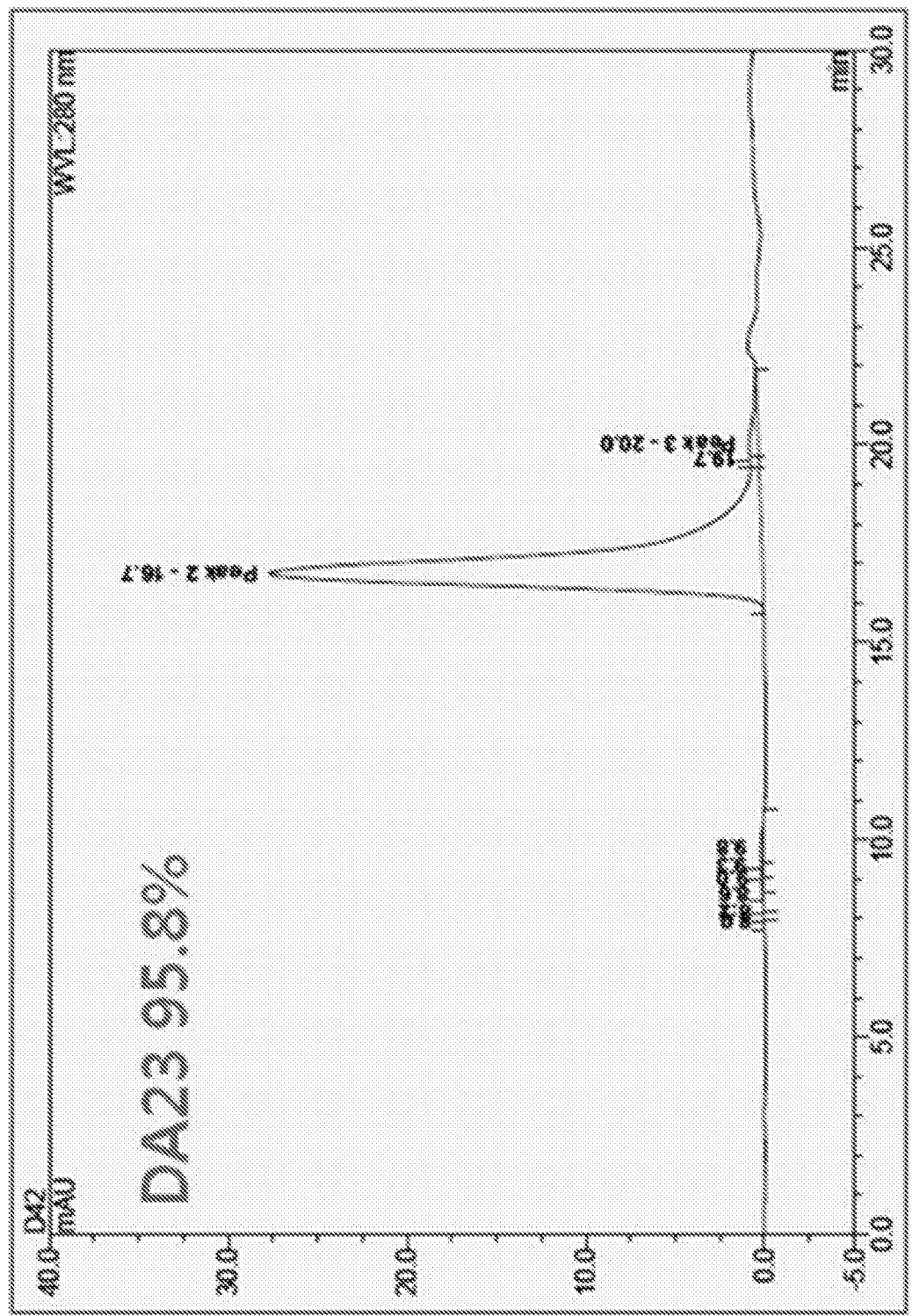
Figure 4G:
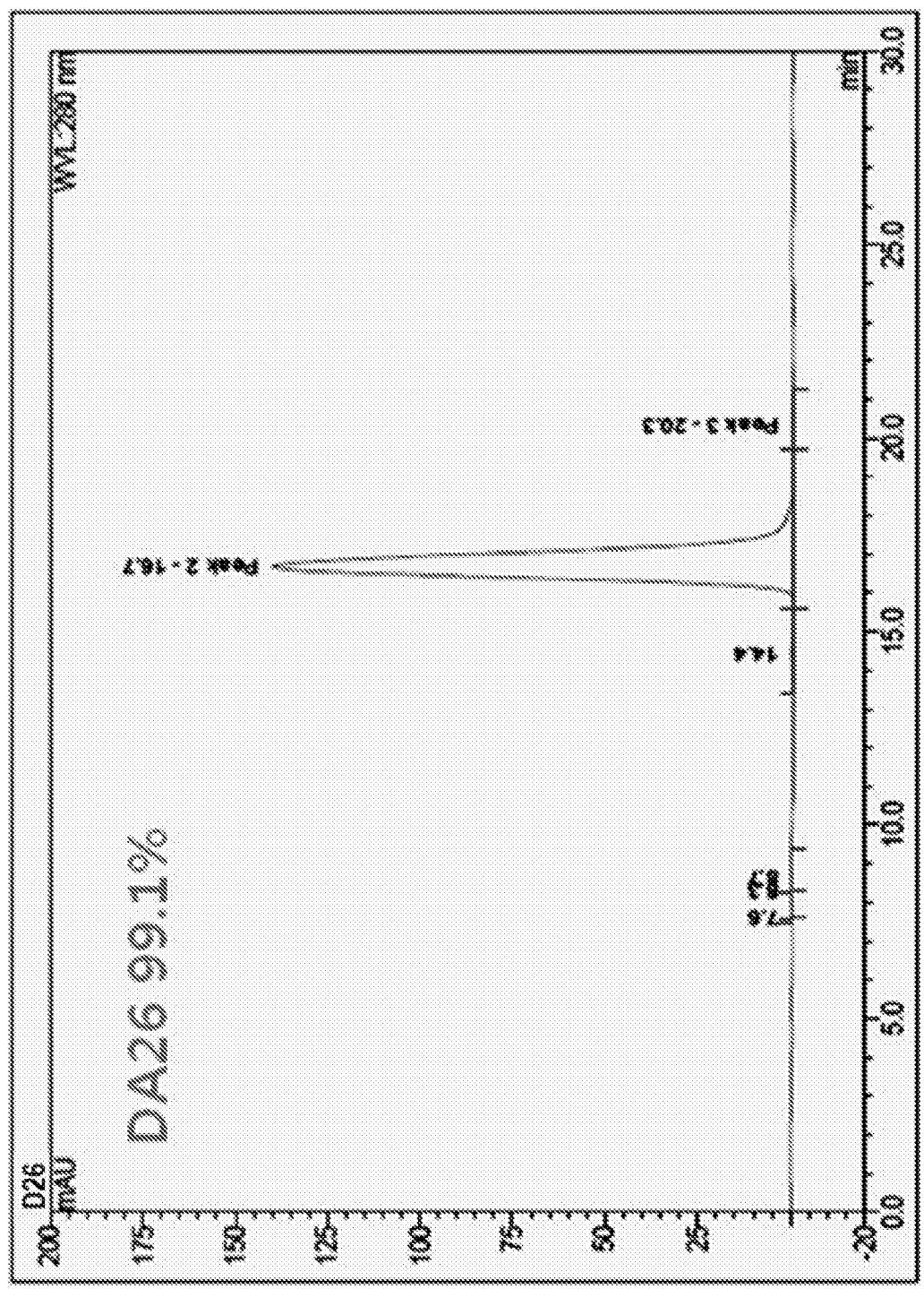
Figure 4H:
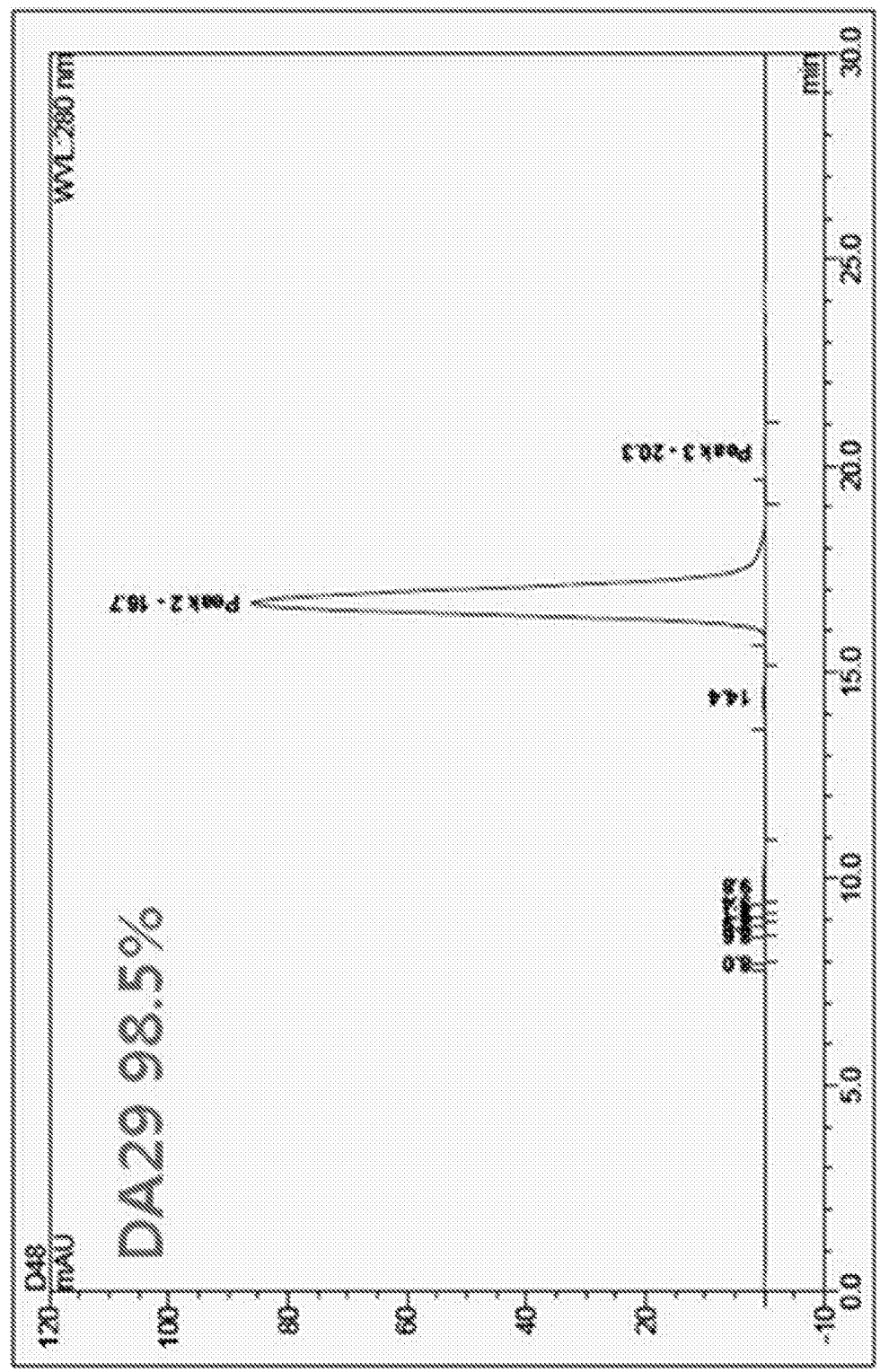

Antibody purity and (soluble) aggregates were analyzed by size exclusion chromatography (SEC) using a TSKgel G3000SWx1 column (Tosoh, Japan). The results are depicted in FIGS. 4a (control antibody AP), 4b (D0), 4c (DA1), 4d (DA4), 4e (DA15), 4f (DA23), 4g (DA26), and 4h (DA29). SEC was operated with isocratic elution using 100 mM phosphate buffer (pH 6.6) as the mobile phase and measurement of absorbance at 280 nm. In general, a high purity of over 94% was observed, with monomers accounting for 94% or more of the total peak area and aggregate peaks accounting for less than 6%.

Example 9

Pharmacokinetics of Antibody

In order to examine in vivo kinetics of the antibodies constructed above, blood half-life was evaluated in mice. Antibodies were intravenously injected at doses of 1-10 mg/kg into nude mice. Blood was sampled from the orbital vein from 5 min to 14 days after injection. The blood collection was conducted using heparinized capillary tubes. Plasma obtained by centrifugation of the blood samples was diluted at certain ratios and used as samples for ELISA evaluation. Human DR5 diluted to a concentration of 10 ng/ml was plated at 100 µl per well onto 96-well immune plates (Nunc, U.S.A.) and adsorbed to the wells for 12-14 hours. The plates were washed three times with buffer solution containing 0.1% Tween 20 and blocked with buffer solution containing bovine serum albumin (Sigma, U.S.A.) at room temperature for 1 hour. After three rounds of washing with buffer solution, the plates were incubated with each of the mouse plasma dilutions and a serial dilution of standard substance at room temperature for 2 to 3 hours. After three washes with buffer solution, a 1:20000 dilution of an HRP-conjugated anti-human immunoglobulin Fc (Fc-HRP) antibody (Bethyl, U.S.A.) was added at a volume of 100 µl per well and incubated at room temperature for 1 hour. After washing three times, 100 µl of a TMB solution (Sigma, U.S.A.) was added to each well and allowed to react. When the color development reached a certain level, the reaction was terminated with 0.2 N sulfuric acid solution. Absorbance at 450 nm was measured using a spectrophotometer (Molecular Device, U.S.A.). The antibody concentration in each plasma sample was calculated from the optical density (OD) measurements, and pharmacokinetic parameters were estimated using WinNonLin ver. 6.2.0.495. The results are shown in FIG. 5 and Table 12 below.

TABLE 12

| | | Unit | D0 10 mg/kg | DA22 10 mg/kg | DA23 10 mg/kg |
|---|---|---|---|---|---|
| Cmax | | ug/ml | 286.9 | 227.9 | 195.8 |
| AUCinf | | hr*ug/ml | 914.1 | 1025.3 | 685.3 |
| t½ | initial (−1 d) | day | 0.57 | 0.70 | 0.58 |
| | Terminal (2 d∼14 d) | day | 6.68 | 8.37 | 7.97 |
| Rsq | initial (−1 d) | | 1.000 | 1.000 | 1.000 |
| | Terminal (2 d∼14 d) | | 1.000 | 0.988 | 0.990 |

Figure 5:
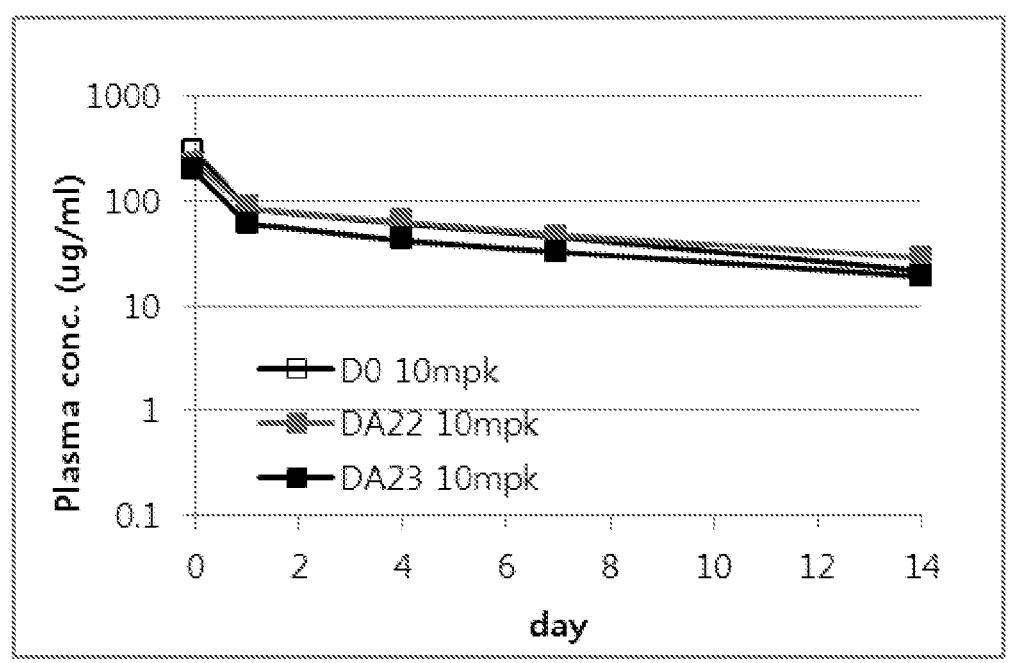
FIG. 5 is shows the pharmacokinetic profile of the antibodies according to the present disclosure.

As shown in FIG. 5 and Table 12, the antibodies (D0, DA22, and DA23) showed blood half-lifes of 6.68 to 8.37 days in the mice employed.

Example 10

Confirmation of Cytotoxicity of Antibody in Tumor Cells

The biological activity of the prepared antibodies was determined using in vitro cell death assays. For this assays, the human colorectal cancer cell line Colo205 (ATCC, U.S.A.), the human pancreatic cancer cell line Miapaca-2 (ATCC, U.S.A.), and the human lung cancer cell line H2122 (ATCC, U.S.A.) were employed.

Figure 6A:
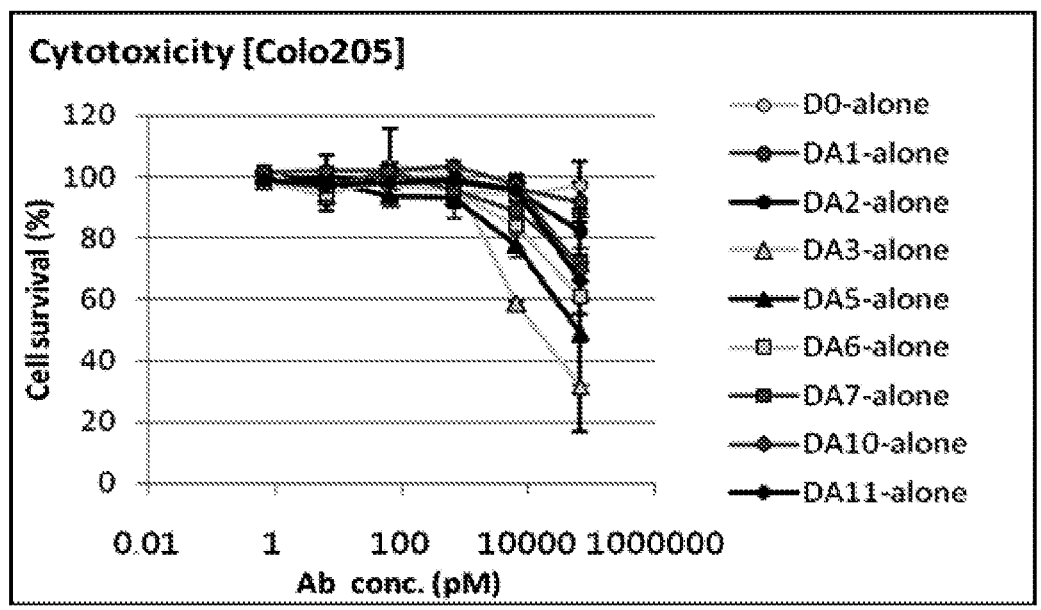
FIGS. 6a to 6r demonstrate that the antibodies according to the present disclosure have cytotoxic activity in tumor cells.
Figure 6B:
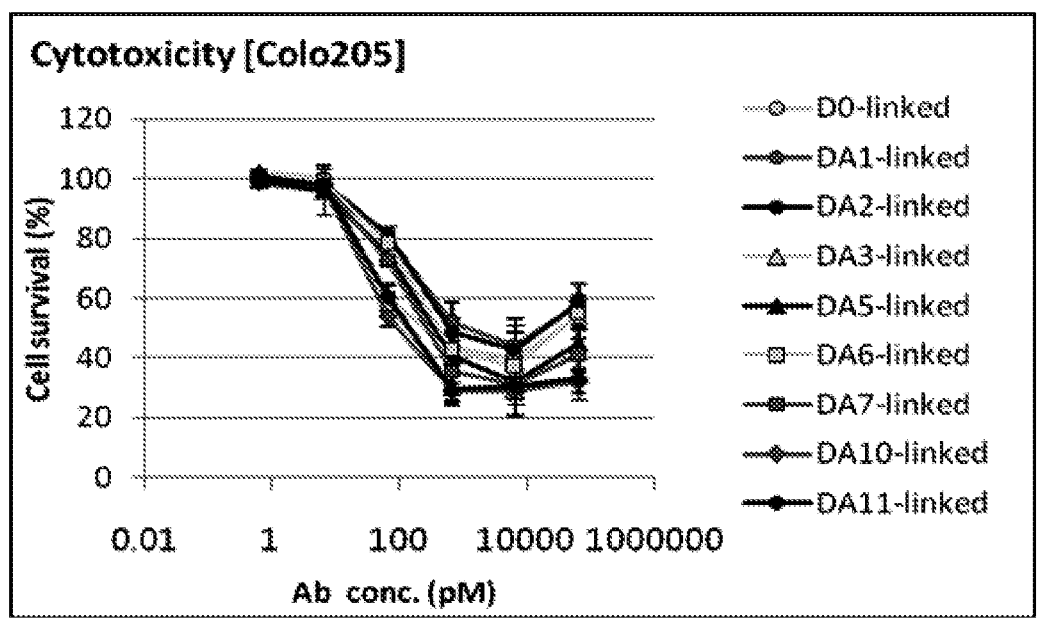
Figure 6C:
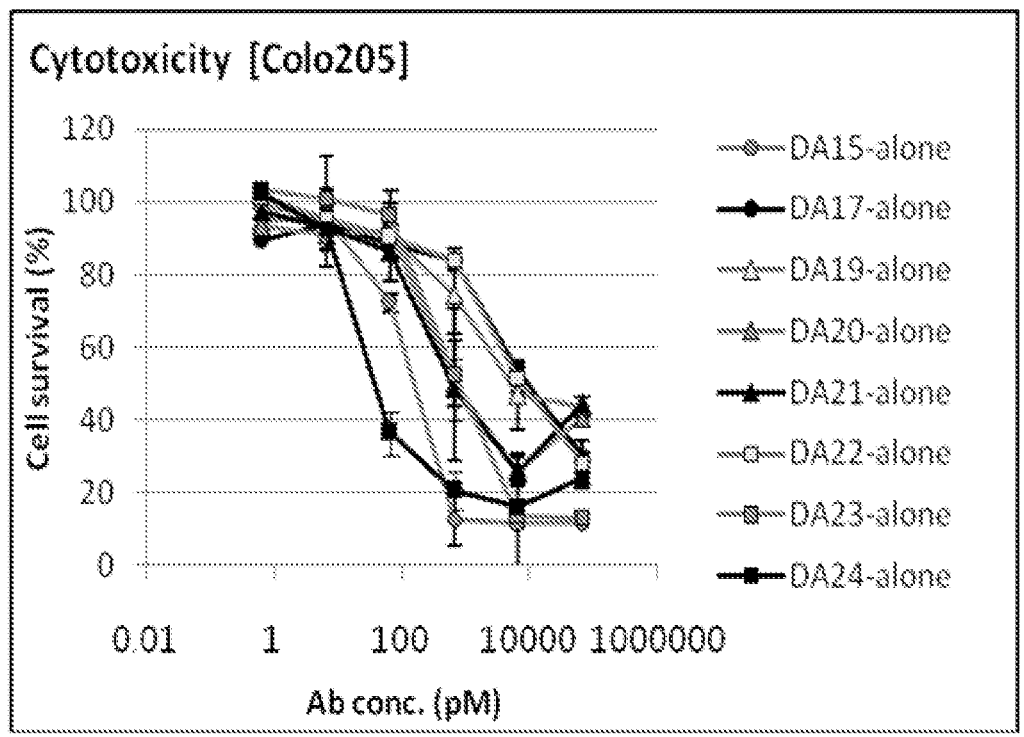
Figure 6D:
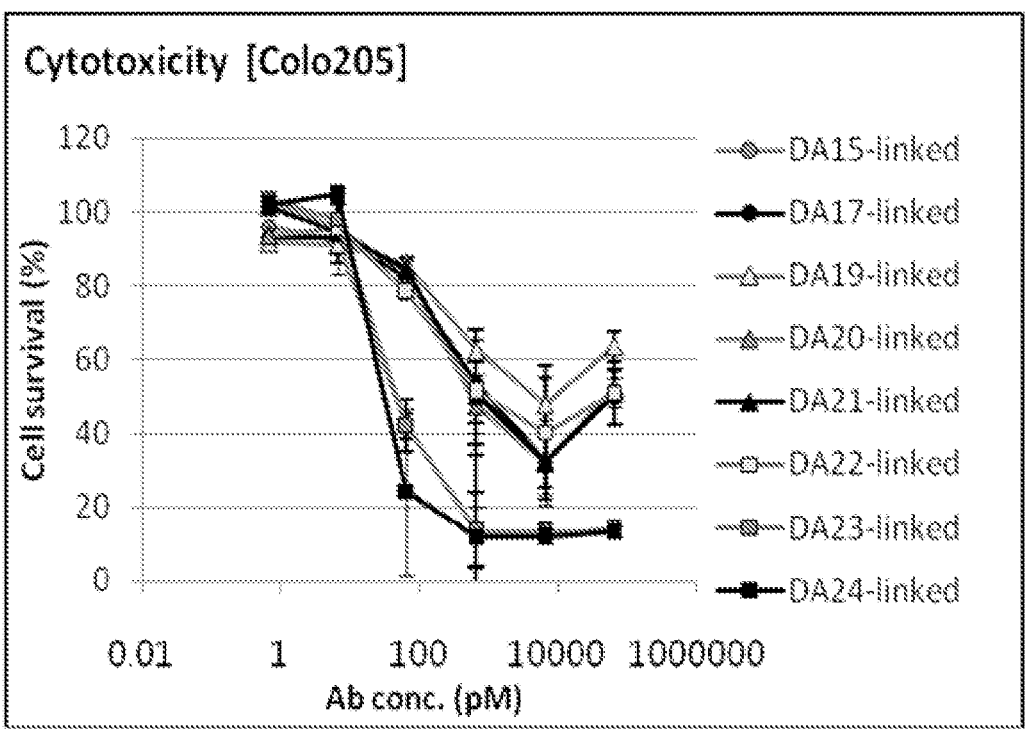
Figure 6E:
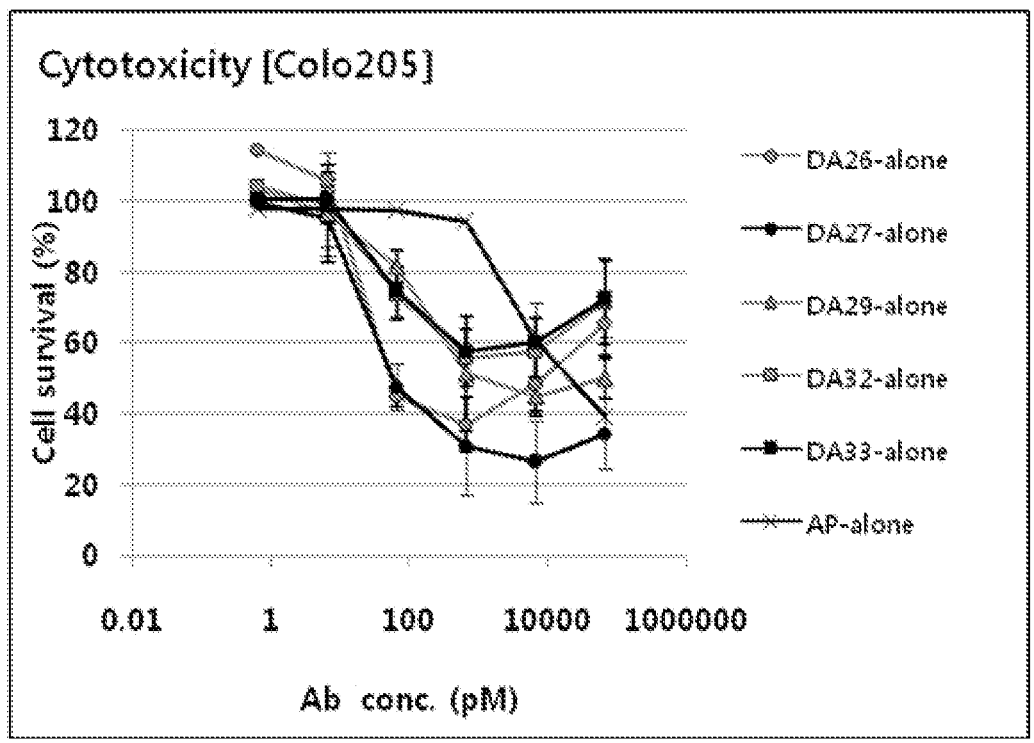
Figure 6F:
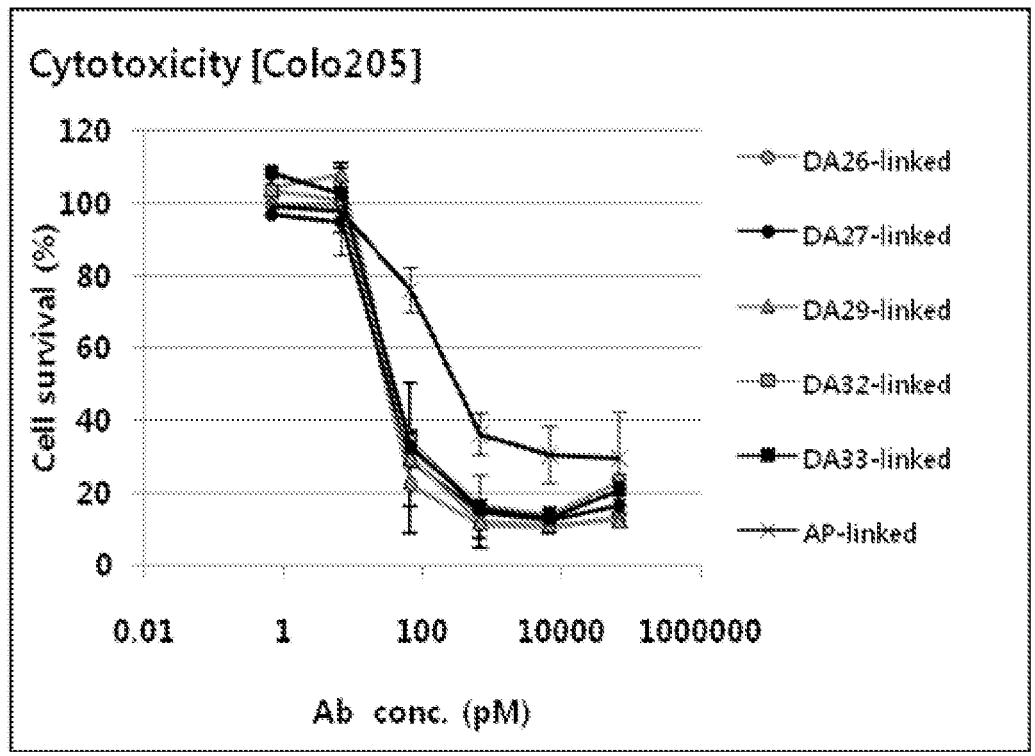
Figure 6G:
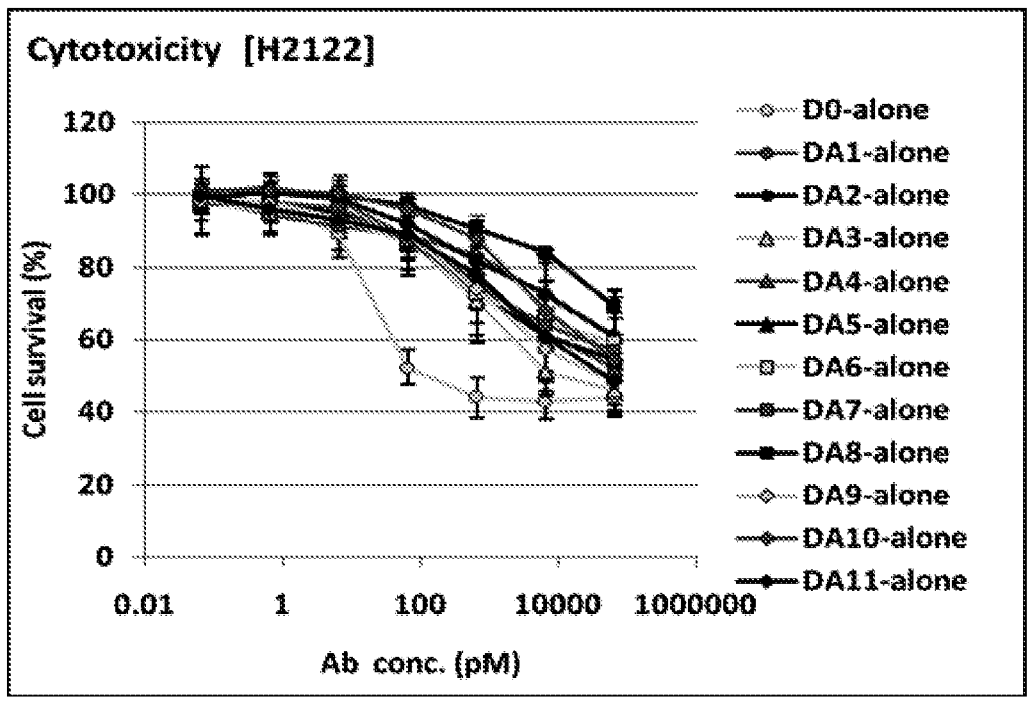
Figure 6H:
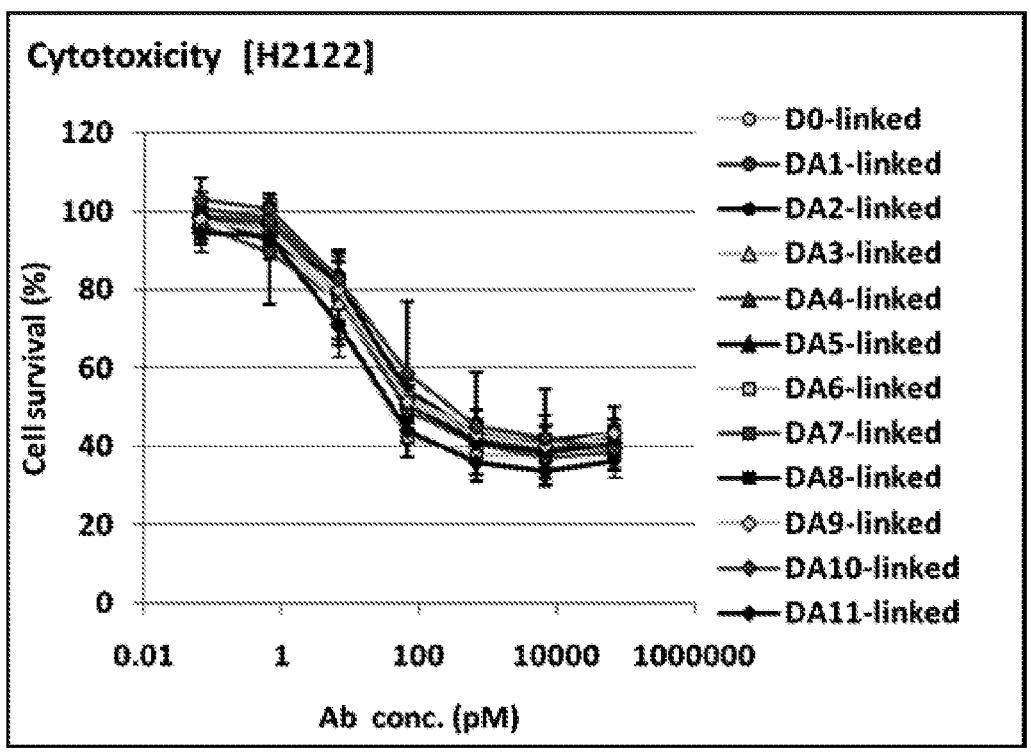
Figure 6I:
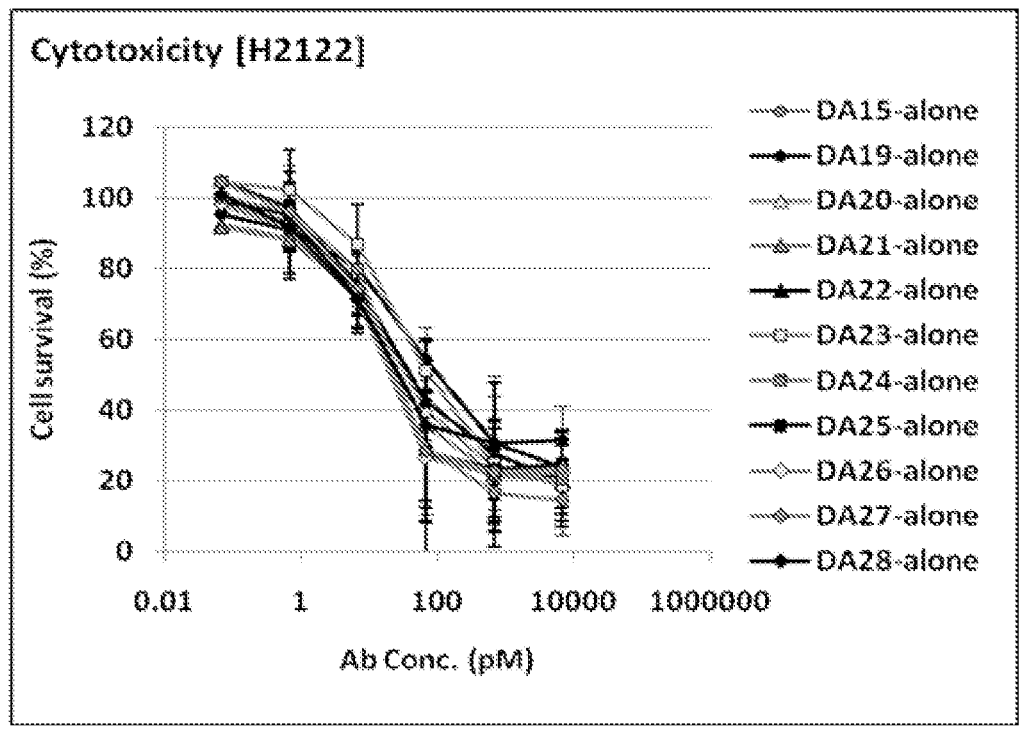
Figure 6J:
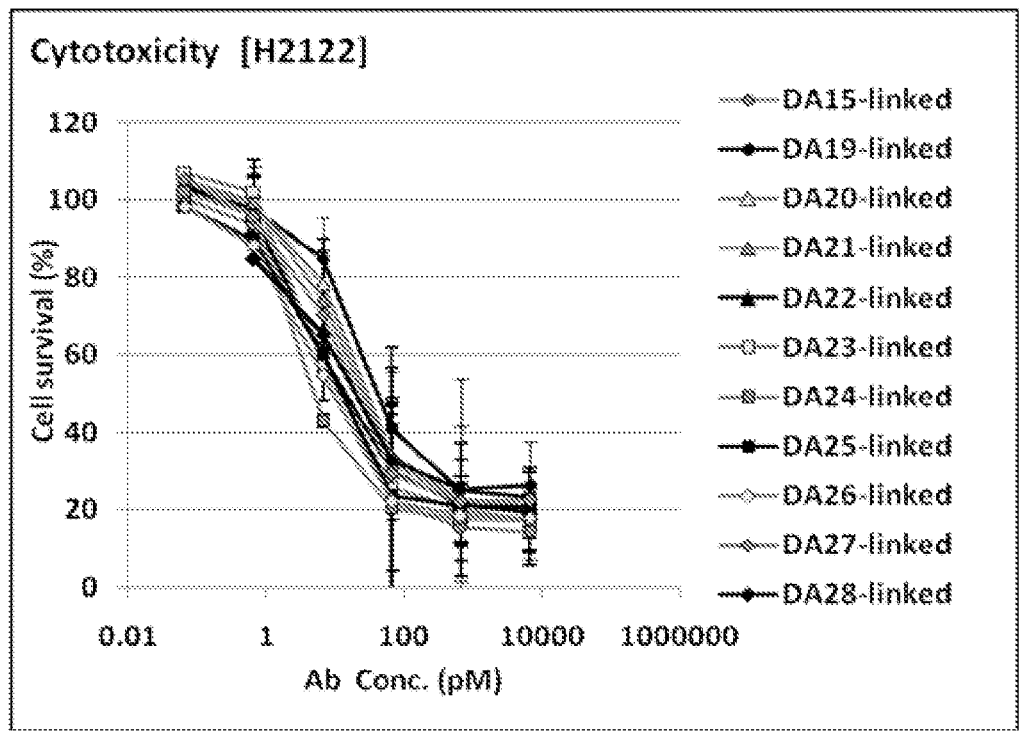
Figure 6K:
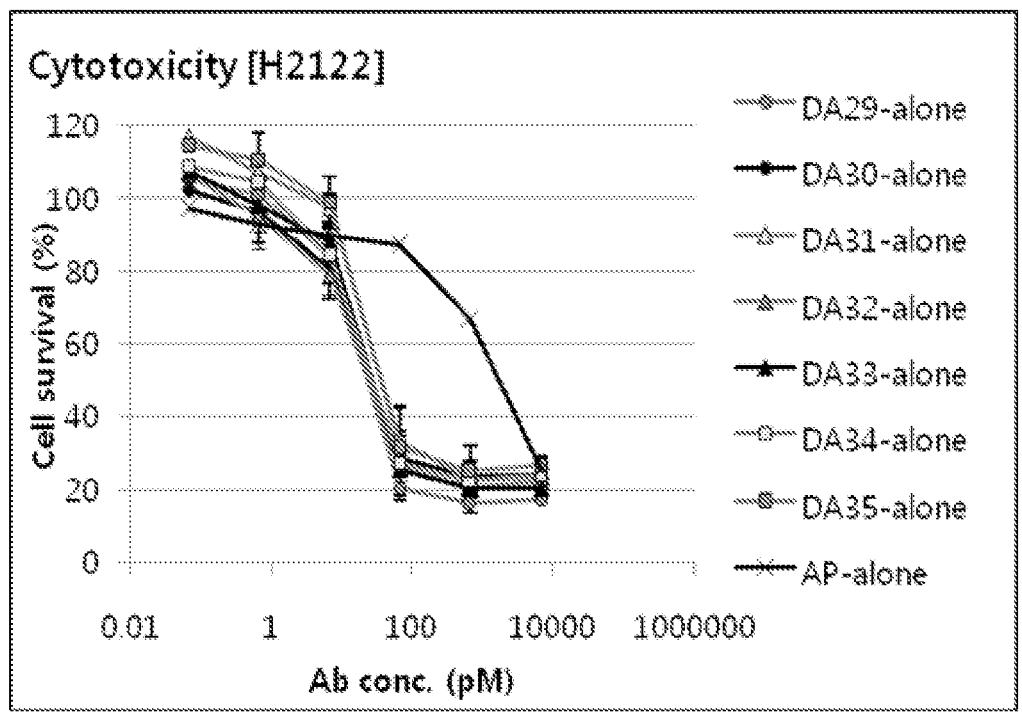
Figure 6L:
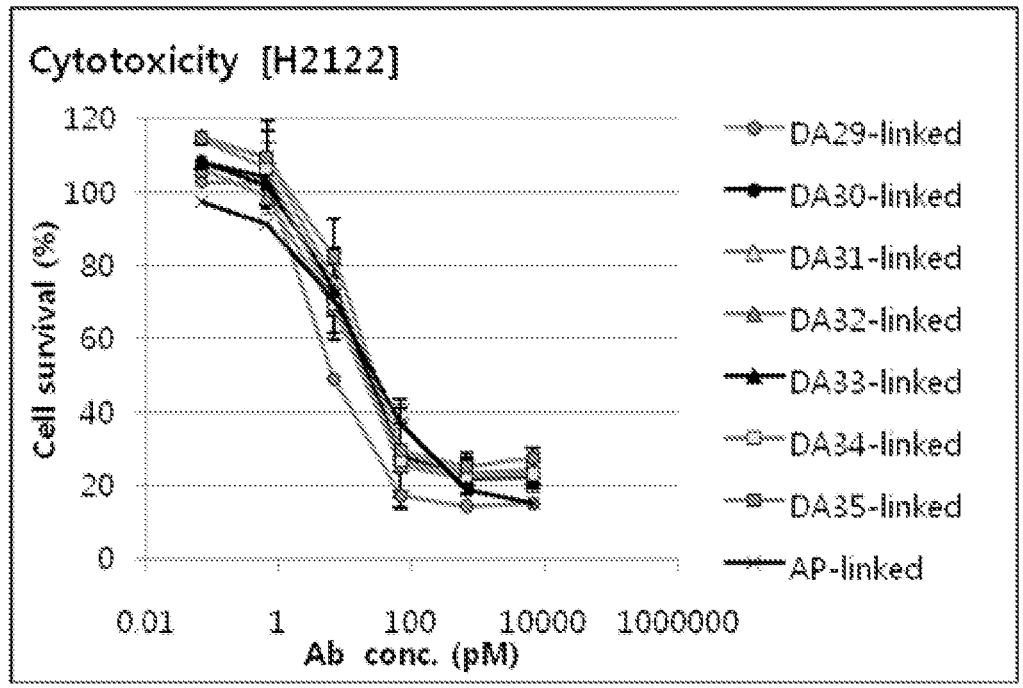
Figure 6M:
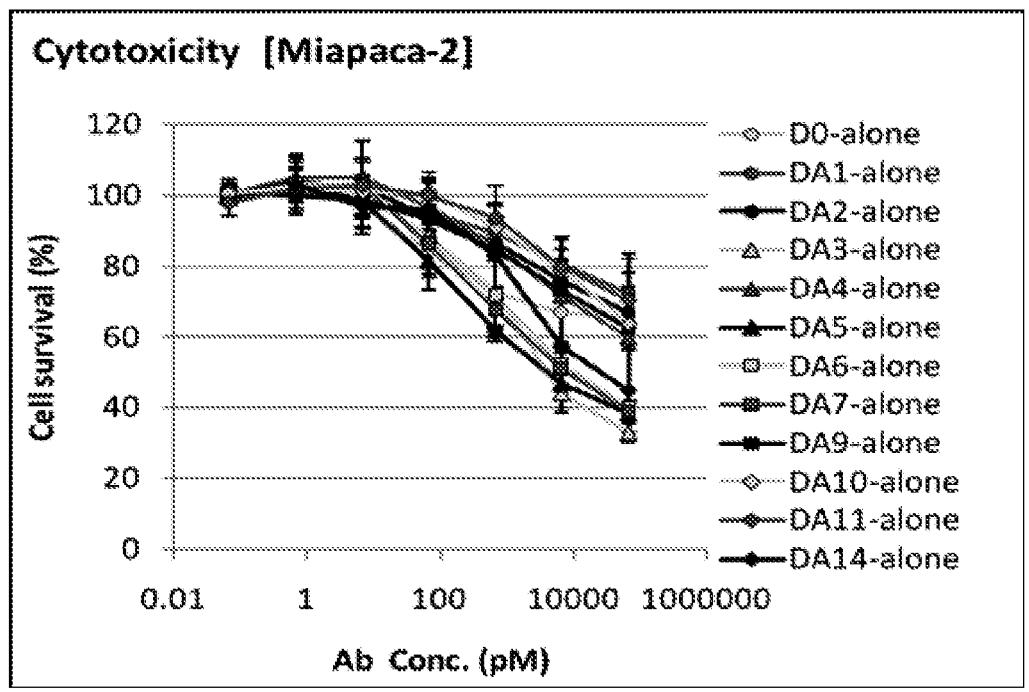
Figure 6N:
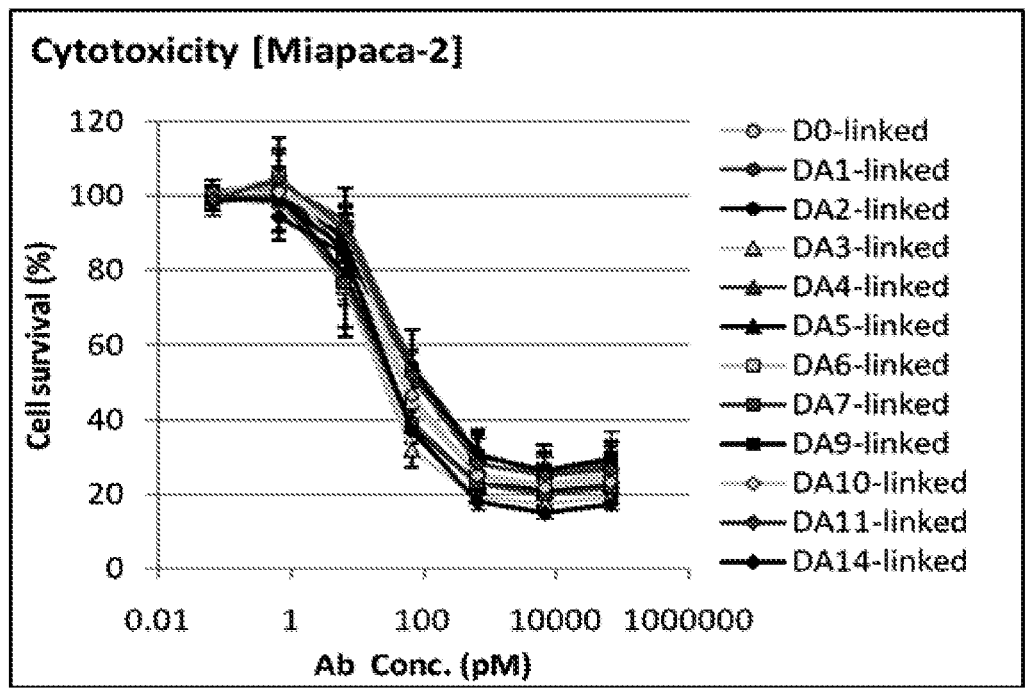
Figure 6O:
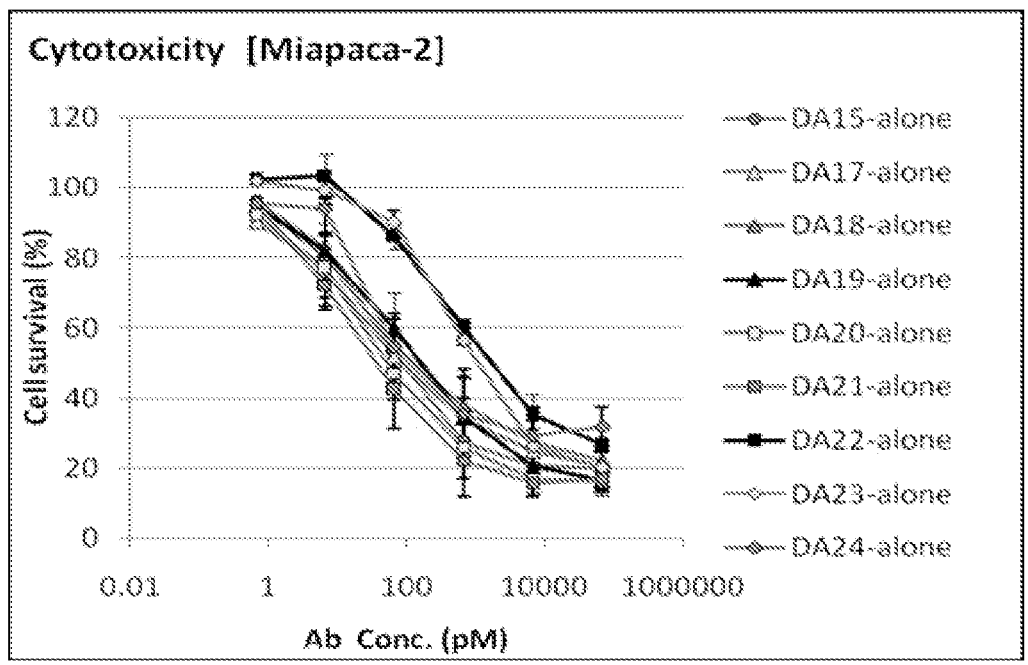
Figure 6P:
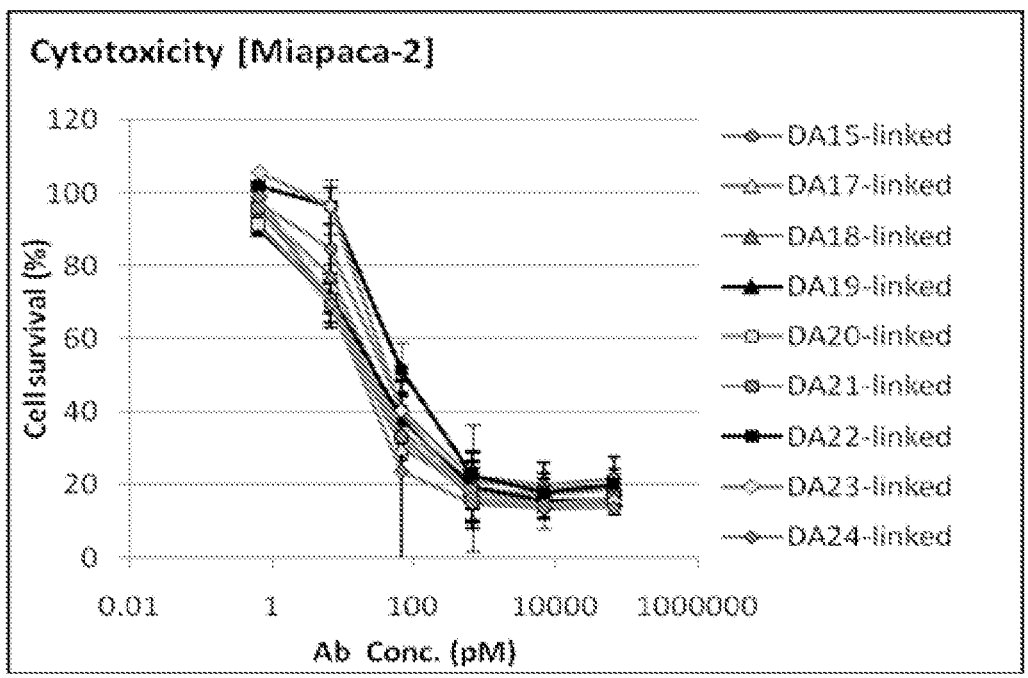
Figure 6Q:
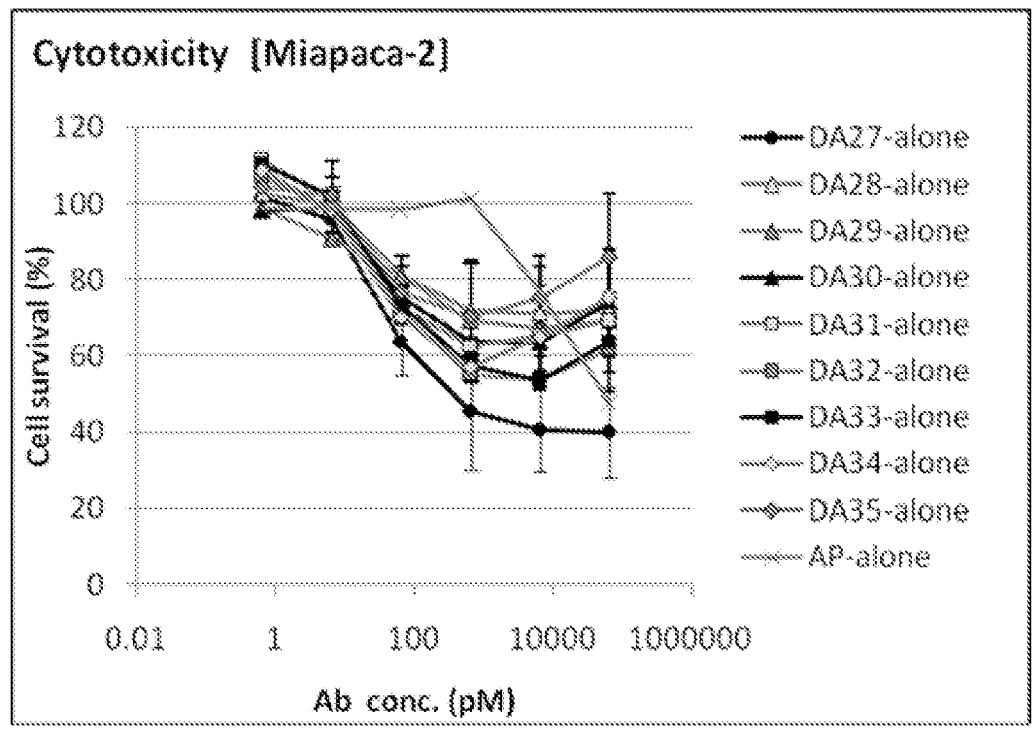
Figure 6R:
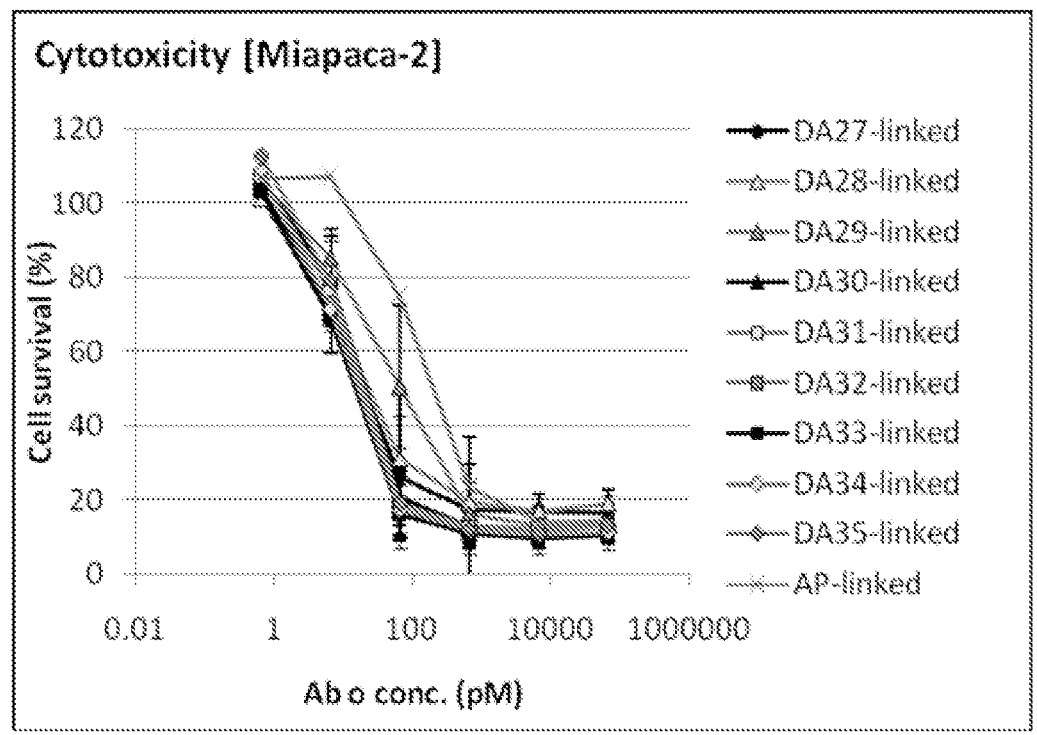

Each tumor cell line was suspended at a density of $1 \times 10^5$ cells/ml, plated at 50 μl per well into 96-well cell culture plates, and cultured for 16-24 hours in a constant temperature and humidity chamber. The antibodies having certain concentrations (0.06-66,000 μM) were applied alone (Ab alone) or in combination with a crosslinking antibody (anti-human Fc) (Serotec, U.S.A.) (Ab linked) and then incubated for 48 hours. 10 μl of resazurin solution (Invitrogen, U.S.A.) was added to each well and incubated for 1 to 2 hours in a constant temperature and humidity chamber. Thereafter, fluorescence was read at 590 nm using a spectrophotometer (Molecular Device). Cell viability was calculated as the percentage of relative fluorescence units (RFU) of test substance-treated group (treated RFU) to relative fluorescence units of a medium-treated group (untreated RFU) (Cell viability (%)=treated RFU/Untreated RFU×100). The results are depicted in FIGS. 6a to 6r. For comparison, the same assay as described above was performed on the control antibody AP.

As can be seen in FIGS. 6a to 6r, the antibodies constructed above showed excellent cell death activity in all the three human cancer cell lines.

Example 11

Evaluation of Anti-Tumor Activity in Xenograft Models

Anti-tumor activity was evaluated by injecting the antibodies i nude mice to which human cancer cell lines had been implanted. For human DR5-expressing cancer cell lines, the human lung cancer cell line H2122 (ATCC, U.S.A.) and the human pancreatic cancer cell line Miapaca-2 (ATCC, U.S.A.) were employed. Two to five million tumor cells were implanted to lateral subcutaneous sites of female BALB/c nude mice 6-8 weeks old (OrientBio), and then tumor volumes were measured using calipers. When the tumors grew to an average volume of 100 to 300 mm³, the mice were separated into groups, and the above constructed antibodies (control antibody AP and antibody D0) were injected to the assigned groups. The antibodies were given as three weekly intraperitoneal injections (on the day of group separation, on day 7 and on day 14) at doses of 0.05-2 mg/kg. Tumor volumes were measured twice a week over a period of 28 days to 50 days following initial injection. Buffer solution (PBS) was injected as the negative control.

Figure 7A:
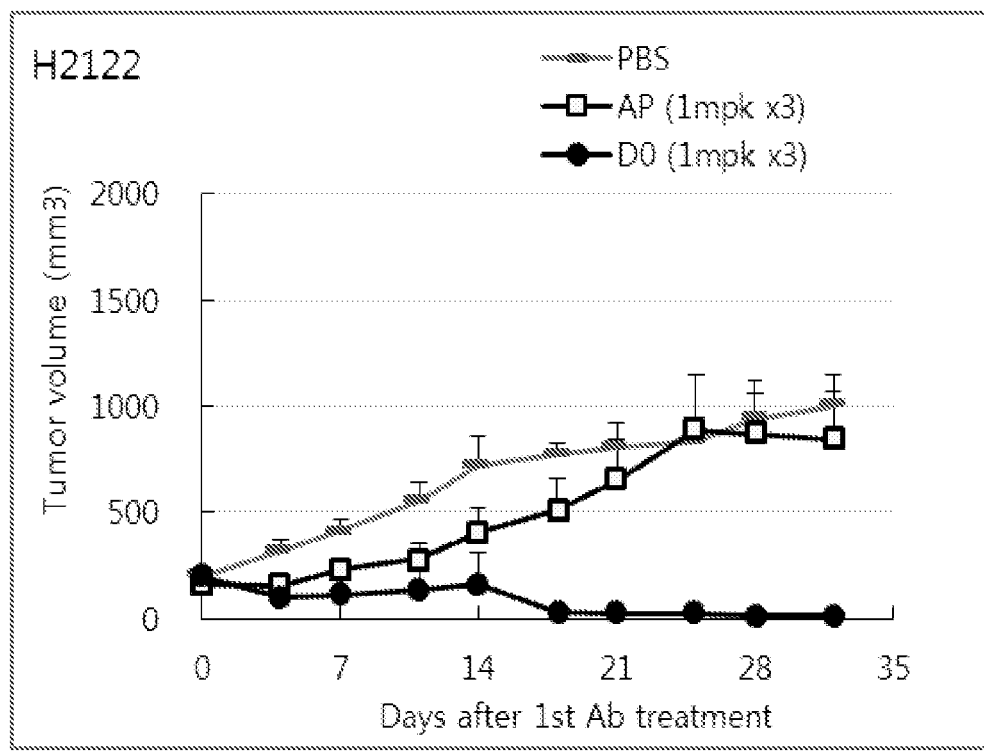
FIGS. 7a and 7b show the results of tumor growth inhibition of the antibodies according to the present disclosure in xenograft animal models.
Figure 7B:
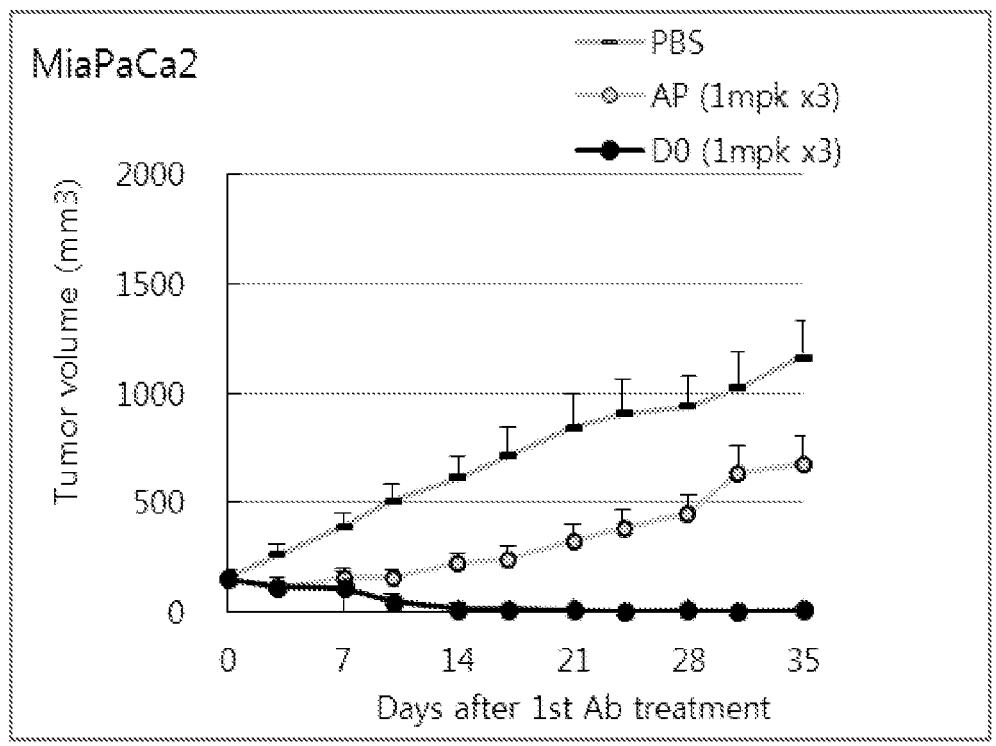

The results are depicted in FIGS. 7a (H2122 implanted mice) and 7b (Miapaca-2-implanted mice). As shown in FIGS. 7a and 7b, the antibody D0 showed anti-tumoral activity superior to the control antibody AP.

Example 12

TRAIL-Uncompetitive Binding

Figure 8A:
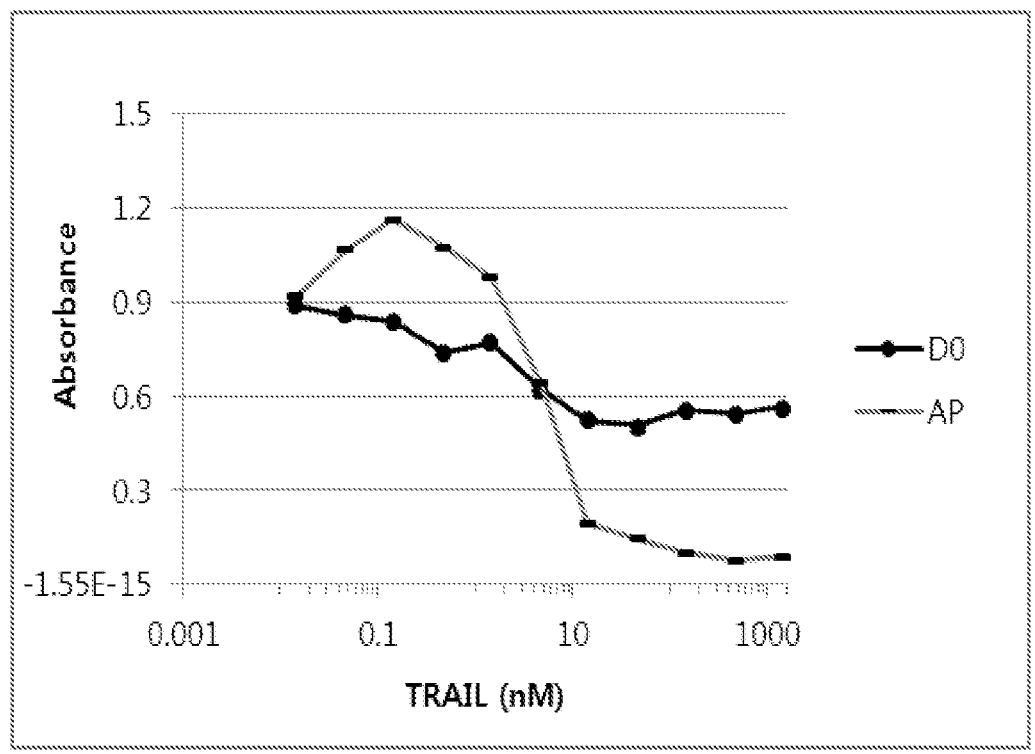
FIGS. 8a and 8b demonstrate that the antibodies according to the present disclosure do not compete with TRAIL for binding to DR5.
Figure 8B:
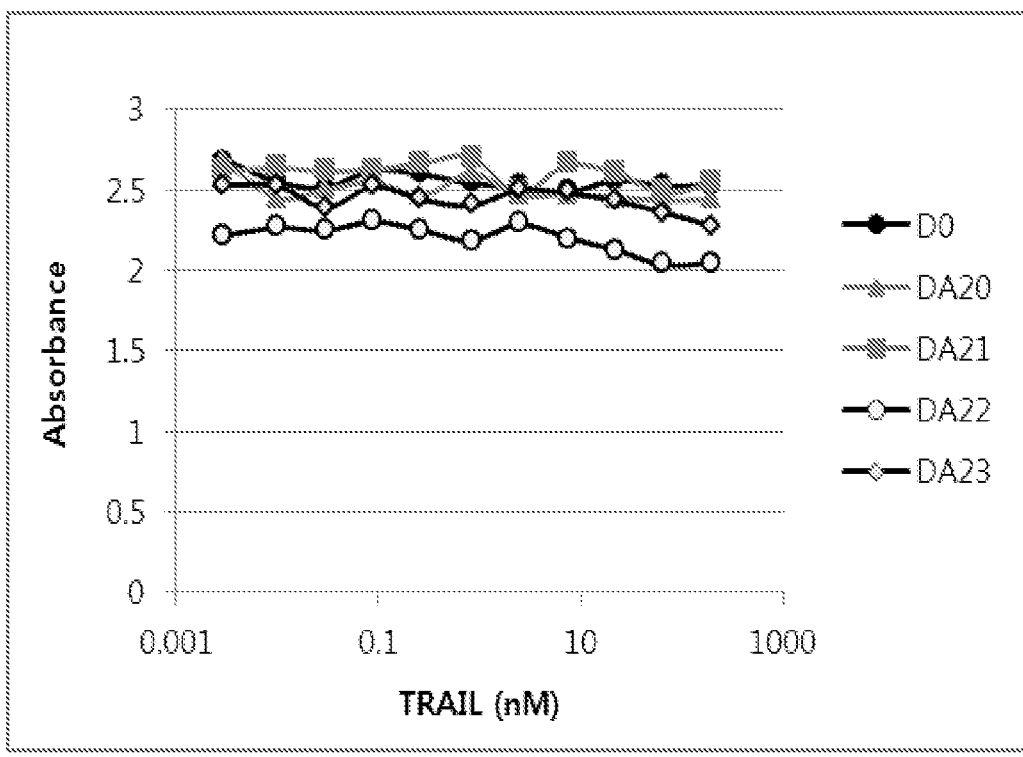

In order to examine antigen-binding characteristics of the antibodies selected in Example 3, a TRAIL competitive enzyme-linked immunosorbent assay was conducted. ELISA plates were coated with 0.1 μg/ml human DR5 (R&D systems, U.S.A.) at 4° C. Thereafter, the plates were incubated with 0.01 nM-1440 nM of antibodies (D0, DA20, DA21, DA21, DA22, and DA23) together with 0.01-400 nM of TRAIL protein for 2 hours. After the plates were washed three times with PBST (0.1% bovine serum albumin and Tween-20 in PBS), HRP (horse radish peroxidase)-conjugated anti-human immunoglobulin Fc was added to each well and incubated for 1 hour. After three washes with PBST, color development was performed for 20 min with ABTS (Thermo, U.S.A.). When the color development reached to a certain level, the reaction was terminated with 1 N sulfuric acid. Absorbance at 405 nm was measured using a spectrophotometer (Molecular Device, U.S.A.) and is depicted in FIGS. 8a and 8b. The antibody AP disclosed in Example (7-1) was used as a control.

In FIGS. 8a and 8b, antigen binding of the control antibody AP decreased in a TRAIL dose-dependent manner whereas the antibodies D0, DA20, DA21, DA21, DA22, and DA23 maintained a certain level of antigen binding irrespective of TRAIL concentrations, implying that the antibodies of the present invention do not compete with TRAIL for binding to DR5.

Example 13

Effect of Antibody in Combination with TRAIL

Antibody properties according to epitopes were analyzed in terms of cell death activity upon co-treatment with the constructed antibodies and TRAIL. In this test, the human colorectal cancer cell line Colo205 (ATCC, U.S.A.) and the human pancreatic cell line Miapaca-2 (ATCC, U.S.A.) were employed. The tumor cells were suspended at a concentration of $1 \times 10^5$ cells/ml and the suspensions were plated at 50 μl per well into 96-well culture plates, followed by incubation for 16-24 hours in a constant temperature and humidity chamber. Serial dilutions of the antibodies (0.1-10000 ng/ml) and TRAIL protein at determined concentrations (0.5, 1, 10 ng/ml) were applied in combination to the 96-well plates. After incubation for 48 to 72 hours at a constant temperature in a humidified condition, a resazurin solution (Invitrogen, U.S.A.) was added at an amount of 10 μl to per well. When the reaction reached a certain level after 1 to 2 hours, fluorescence was read at 590 nm using a spectrophotometer (Molecular Device). Cell viability was calculated as the percentage of relative fluorescence units (RFU) of a test substance-treated group (treated RFU) to the relative fluorescence units of a culture medium-treated group (untreated RFU) (Cell viability (%)=treated RFU/Untreated RFU× 100).

Figure 9A:
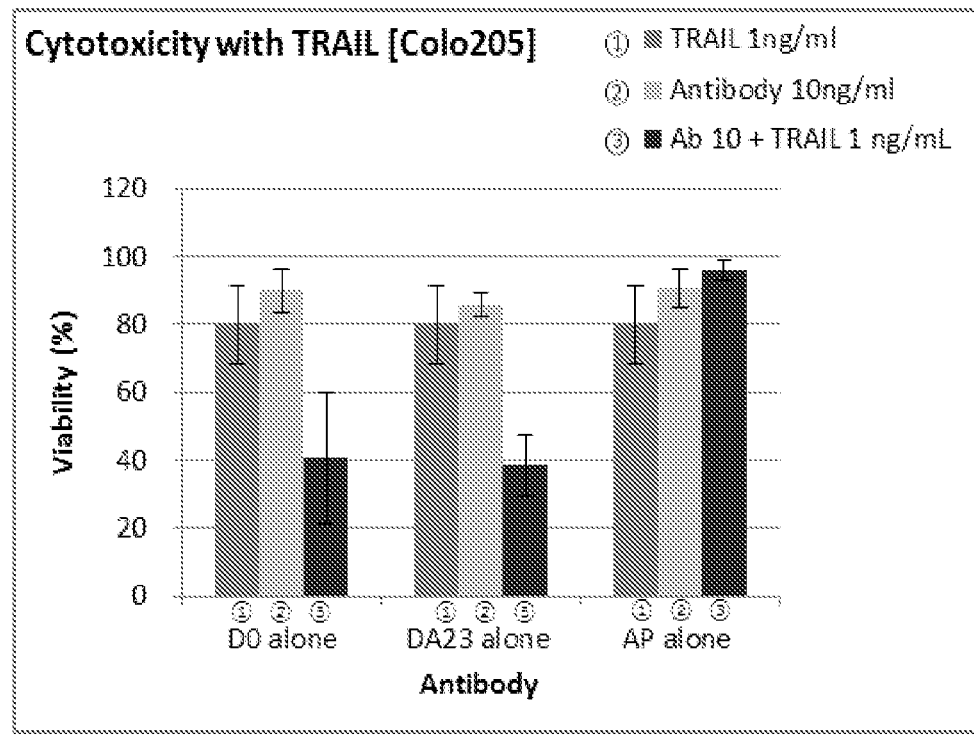
FIGS. 9a and 9b are graphs delineating synergistic effects of the antibodies according to the present disclosure and TRAIL in assays for inducing cell death.

Representative results are depicted in FIGS. 9a (Colo205) and 9b (Miapaca-2). For comparison, the above described antibody AP was used as a control, based on the observation in literature (Cell Death and Differentiation, 15, 751-761, 2008) that this antibody AP has a similar binding site to that of TRAIL.

Figure 9B:
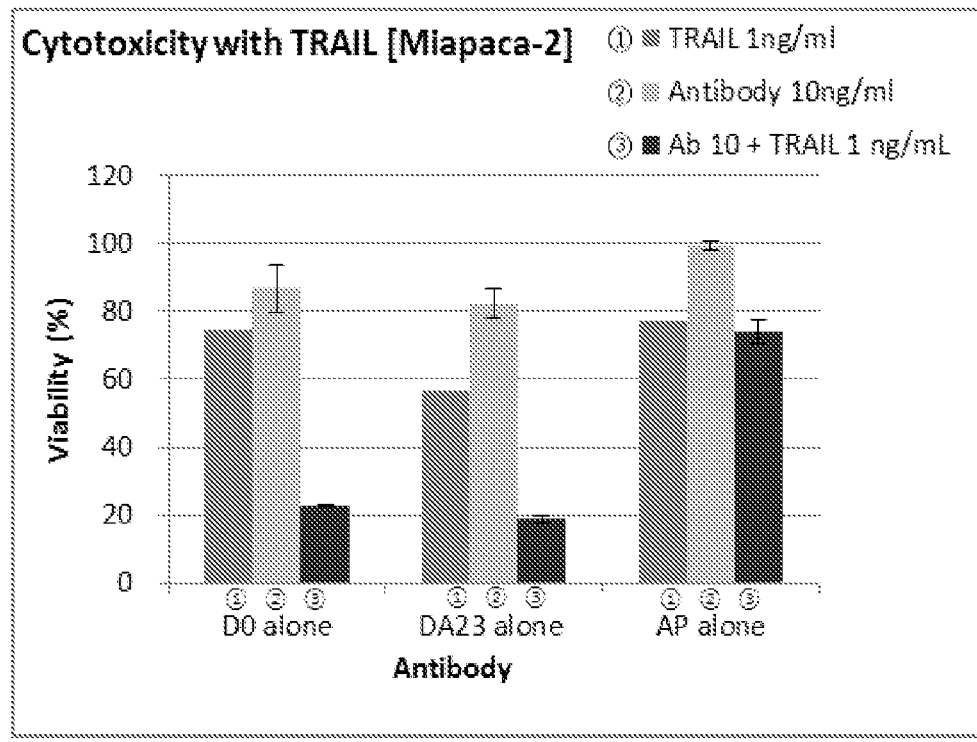

As can be seen in FIGS. 9a and 9b, higher cell death activity was detected when the antibody D0 or DA23 at concentrations as low as 10 ng/ml were used in combination with TRAIL at certain concentrations, compared to antibody alone, whereas no such increase in activity was observed for the control antibody AP.

Example 14

Assay for Intracellular Caspase Activity

In order to investigate the cell death mechanism thereof, the constructed antibodies were assayed for caspase activity. The activity of caspase-3/7 was measured using Apo-ONE® Homogeneous Caspase-3/7 Assay kit (Promega, U.S.A.). In this assay, the human colorectal cancer cell line Colo205 (ATCC, U.S.A.), the human pancreatic cancer cell line Miapaca-2 (ATCC, U.S.A.), and the lung cancer cell line H2122 (ATCC, U.S.A.) were employed. A suspension of each tumor cell line having a concentration of $1 \times 10^5$ cells/ml was plated at a volume of 50 µl per well into 96-well cell culture plates and cultured for 16-24 hours in a constant temperature and humidity chamber. The cells were treated with predetermined concentrations (0.01-10000 ng/ml) of the antibody alone (Ab alone) or in combination with a crosslinking antibody (anti-human Fc) (Serotec, U.S.A.) (Ab linked) and then cultured for 4 hours. Subsequently, the cells were incubated for 3 to 16 hours with 100 µl of Apo-ONE® Caspase-3/7 Reagent (Promega, U.S.A.) per well in a constant temperature and humidity chamber. When the reaction reached a predetermined level, fluorescence was read at 520 nm using a spectrophotometer (Molecular Device). Caspase activity was calculated as a fold increase of relative fluorescence units (RFU) of a test substance-treated group (treated RFU) to over the relative fluorescence units of a culture medium-treated group (untreated RFU) (Caspase activity=treated RFU/Untreated RFU).

Figure 10A:
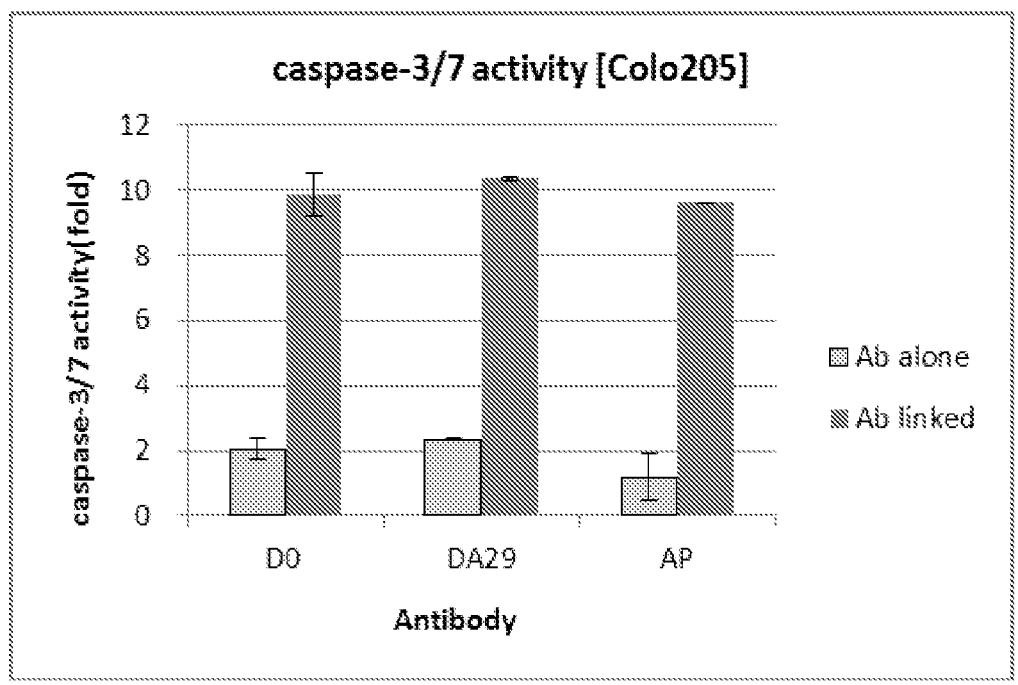
FIGS. 10a to 10c are graphs demonstrating that the antibodies according to the present disclosure induce cell death via apoptosis.
Figure 10B:
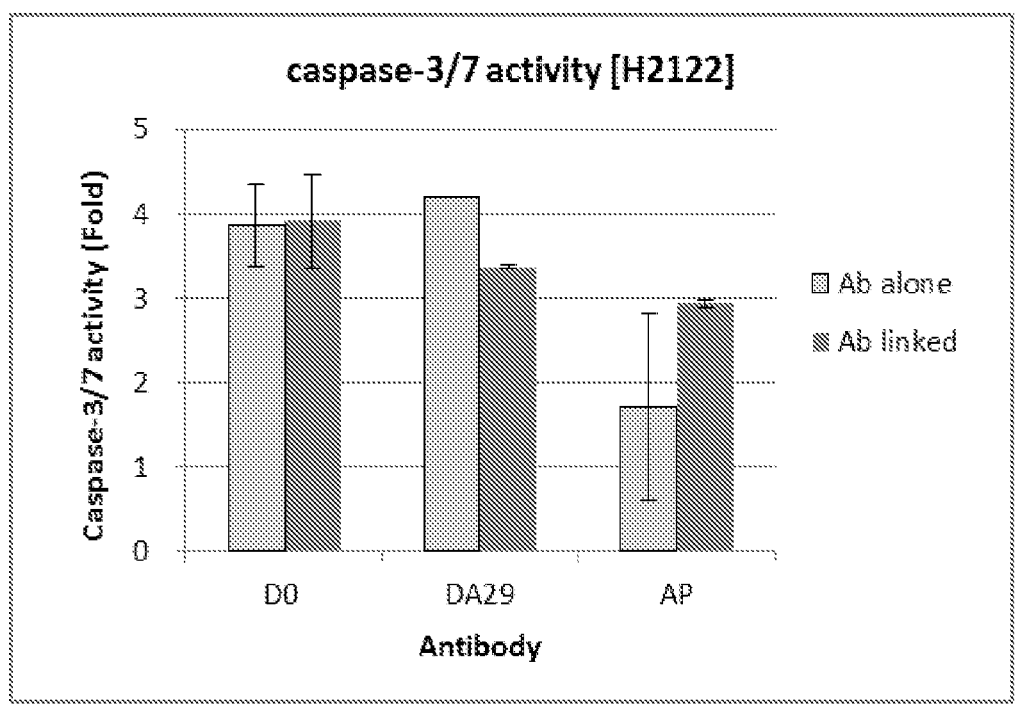
Figure 10C:
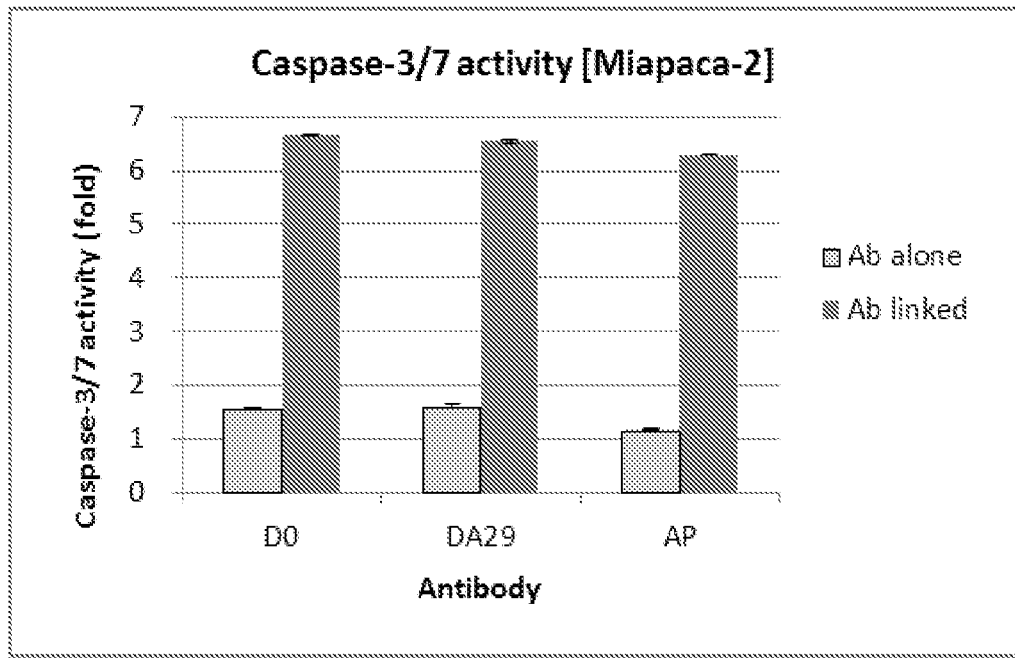

Representative results are depicted in FIGS. 10a (Colo205), 10b (H2122), and 10c (Miapaca-2). For comparison, the antibody AP was treated in the same manner As can be seen in FIGS. 10a and 10c, the application of the antibody D0 or DA29 to the cancer cell lines elicited an increase in the activity of casapse-3/7, implying that the cell death mechanism of the antibody of the present disclosure involves the apoptosic pathway.

Example 15

Combination Effect of Antibody and Drug

Effects obtained from co-treatment with the above constructed antibody and gemcitabine were evaluated using in vitro tumor cell death assay. This assay was based on the observation in the literature (J Gastrointest Surg. 2006 November; 10(9):1291-300) wherein the co-treatment of pancreatic cancer cells with gemcitabine and an anti-DR5 antibody resulted in greater tumor cell death and caspase activity.

Figure 11A:
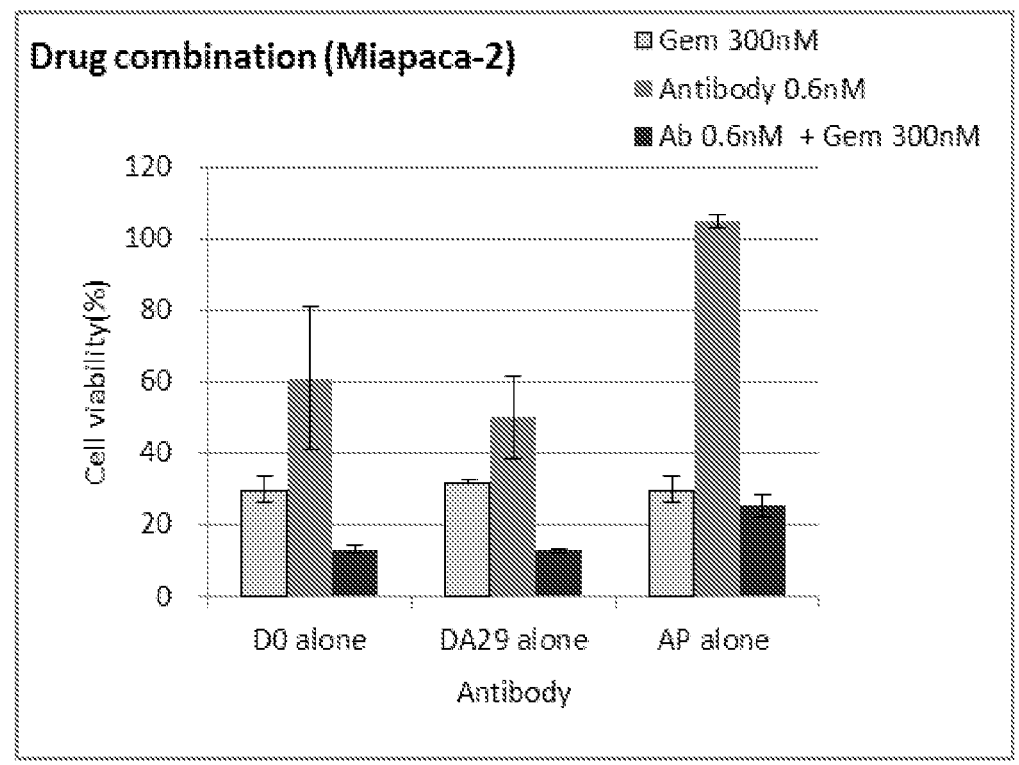
FIGS. 11a and 11b show the cytotoxic activity of the antibodies according to the present disclosure when used in combination with certain concentrations of gemcitabine.
Figure 11B:
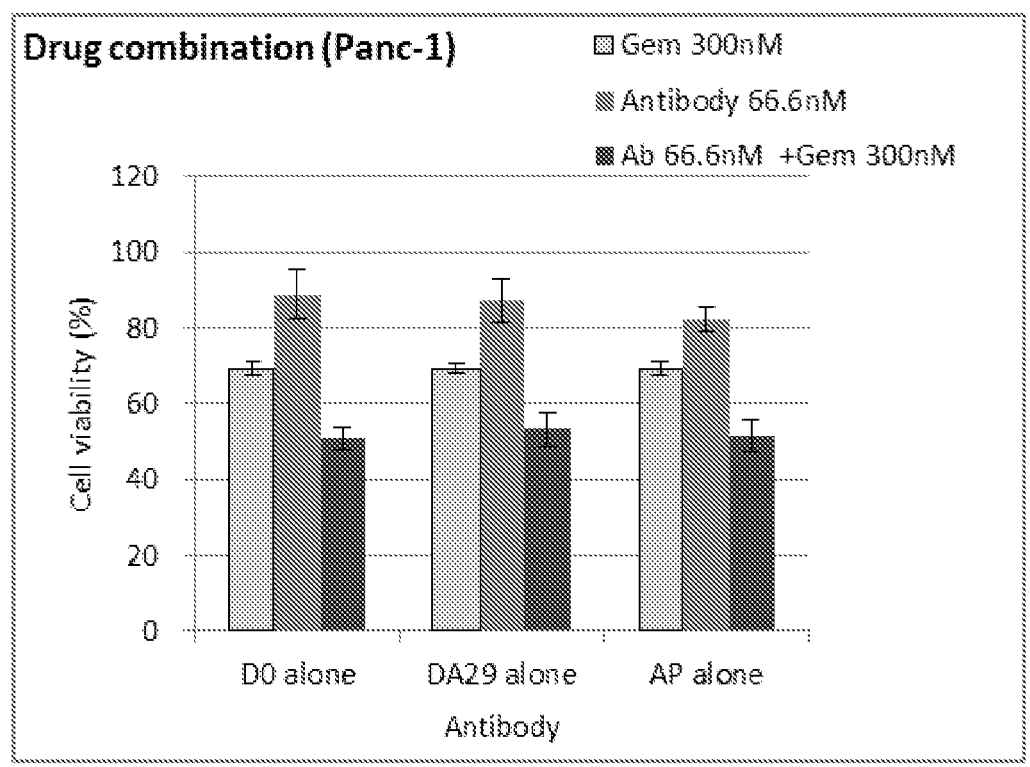

The human pancreatic cancer cell lines Miapaca-2 (ATCC, U.S.A.) and Panc-1 (ATCC, U.S.A.) were each suspended at a density of $1 \times 10^5$ cells/ml. The suspensions were added in an amount of 50 µl to each well of 96-well cell culture plates and incubated for 16-24 hours in a constant temperature and humidity chamber. The cancer cell lines were treated with the anti-DR5 antibodies of the present disclosure including D0 in combination with certain concentrations (3 nM-300 nM) of gemcitabine and cultured for 48 to 72 hours. The cells were further incubated for 1 to 3 hours after addition of 10 µl of a resazurin solution (Invitrogen, U.S.A.) per well. When the reaction proceeded to a predetermined level, fluorescence was read at 590 nm using a spectrophotometer (Molecular Device). Cell viability was calculated as the percentage of relative fluorescence units (RFU) of a test substance-treated group (treated RFU) to relative fluorescence units of a culture medium-treated group (untreated RFU) (Cell viability (%)=treated RFU/Untreated RFU×100). The results are depicted in FIGS. 6a to 6r. Representative results are depicted in FIGS. 11a (Miapaca-2) and 11b (Panc-1). For comparison, the control antibody AP was treated in the same manner As can be seen in FIGS. 11a and 11b, increased apoptotic activity was detected upon co-treatment with the antibody D0 or DA29 and gemcitabine relative to treatment with each individual substance.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An anti-death receptor 5 (DR5) antibody or an antigen-binding fragment thereof, the antibody comprising:
   a polypeptide having the amino acid sequence of SEQ ID NO: 1 ($V_H$-CDR1),
   a polypeptide having the amino acid sequence of SEQ ID NO: 2 ($V_H$-CDR2),
   a polypeptide having the amino acid sequence of SEQ ID NO: 3 ($V_H$-CDR3),
   a polypeptide having the amino acid sequence of SEQ ID NO: 4 ($V_L$-CDR1), a polypeptide having the amino acid sequence of SEQ ID NO: 5 ($V_L$-CDR2), and a polypeptide having the amino acid sequence of SEQ ID NO: 6 ($V_L$-CDR3).

2. The anti-DR5 antibody or the antigen-binding fragment thereof according to claim 1, wherein the polypeptide $V_H$-CDR3 has an amino acid sequence selected from the group consisting of SEQ ID NOS: 7, 8, and 9.

3. The anti-DR5 antibody or the antigen-binding fragment thereof according to claim 1, wherein the polypeptide $V_L$-CDR2 has an amino acid sequence selected from the group consisting of SEQ ID NOS: 10, 11, and 12.

4. The anti-DR5 antibody or the antigen-binding fragment thereof according to claim 1, wherein the polypeptide $V_L$-CDR3 has an amino acid sequence selected from the group consisting of SEQ ID NOS: 13, 14, 15, and 16.

5. The anti-DR5 antibody or the antigen-binding fragment thereof according to claim 1, wherein the anti-DR5 antibody or the antigen-binding fragment thereof comprises:
 a heavy-chain variable region having an amino acid sequence selected from the group consisting of SEQ ID NO: 17 to SEQ ID NO: 37; and
 a light-chain variable region having an amino acid sequence selected from the group consisting of SEQ ID NO: 38 to SEQ ID NO: 49.

6. The anti-DR5 antibody or the antigen-binding fragment thereof according to claim 1, wherein the anti-DR5 antibody or the antigen-binding fragment thereof has activity of inducing apoptosis in TRAIL (TNF-related apoptosis inducing ligand)-sensitive cancer cells that express DR5 or TRAIL-resistant cancer cells that express DR5.

7. The anti-DR5 antibody or the antigen-binding fragment thereof according to claim 1, wherein the anti-DR5 antibody is a monoclonal antibody.

8. The anti-DR5 antibody or the antigen-binding fragment thereof according to claim 1, wherein the antigen-binding fragment is selected from the group consisting of scFv, (scFv)2, Fab, Fab', and F(ab')2 of the anti-DR5 antibody.

9. The anti-DR5 antibody or the antigen-binding fragment thereof according to claim 1, wherein the anti-DR5 antibody is a chicken derived antibody, a chicken-human chimeric antibody or a humanized antibody.

10. A polynucleotide molecule coding for the anti-DR5 antibody or the antigen-binding fragment according to claim 1.

11. A recombinant vector carrying the polynucleotide molecule of claim 10.

12. A recombinant cell harboring the recombinant vector of claim 11.

13. A method of producing an anti-DR5 antibody or an antigen-binding fragment thereof, the method comprising a step of expressing the polynucleotide molecule of claim 10.

14. A pharmaceutical composition comprising the anti-DR5 antibody or the antigen-binding fragment thereof according to claim 1.

15. A method for treatment of cancer, the method comprising a step of administering the anti-DR5 antibody or the antigen-binding fragment thereof according to claim 1 to a subject in need thereof.

16. The method according to claim 15, wherein the cancer is selected from the group consisting of blood cancer, lung cancer, stomach cancer, liver cancer, bone cancer, pancreatic cancer, skin cancer, head and neck cancer, skin melanoma, uterine cancer, ovarian cancer, rectal cancer, colorectal cancer, colon cancer, breast cancer, uterine sarcoma, fallopian tube carcinoma, endometrial carcinoma, uterine cervical carcinoma, vaginal carcinoma, vulva carcinoma, esophageal cancer, laryngeal cancer, small-intestine cancer, thyroid cancer, parathyroid cancer, soft-tissue sarcoma, urethral cancer, penile cancer, prostate cancer, chronic or acute leukemia, solid tumors in juvenile stage, differentiated lymphoma, bladder cancer, renal cancer, renal cell carcinoma, renal pelvic carcinoma, primary central nervous system lymphoma, spinal axis tumors, brain stem glioma, and pituitary adenoma.

17. The method according to claim 15, further comprising a step of administering TNF-related apoptosis-inducing ligand (TRAIL) to the subject.

18. The method according to claim 15, further comprising a step of administering at least one anticancer agent selected from the group consisting of an alkylating anticancer agent, a metabolism antagonist-based anticancer agent, an anthracycline-based anticancer agent; and a proteasome inhibitor-based anticancer agent to the subject.

19. The method according to claim 18, wherein the anticancer agent is at least one selected from the group consisting of carboplatin, paclitaxel, gemcitabine, doxorubicin and bortezomib.

20. The method according to claim 17, further comprising a step of administering at least one anticancer agent selected from the group consisting of an alkylating anticancer agent, a metabolism antagonist-based anticancer agent, an anthracycline-based anticancer agent; and a proteasome inhibitor-based anticancer agent to the subject.

21. The method according to claim 20, wherein the anticancer agent is selected from the group consisting of carboplatin, paclitaxel, gemcitabine, doxorubicin, and bortezomib.

* * * * *